United States Patent
Melis et al.

(10) Patent No.: US 10,889,835 B2
(45) Date of Patent: Jan. 12, 2021

(54) PRODUCTION OF MONOTERPENE BLENDS BY UNICELLULAR PHOTOSYNTHETIC MICROORGANISMS

(71) Applicant: The Regents of the University of Californioa, Oakland, CA (US)

(72) Inventors: Anastasios Melis, El Cerrito, CA (US); Cinzia Formighieri, Saugus, MA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/304,674

(22) PCT Filed: May 26, 2017

(86) PCT No.: PCT/US2017/034754
§ 371 (c)(1),
(2) Date: Nov. 26, 2018

(87) PCT Pub. No.: WO2017/205788
PCT Pub. Date: Nov. 30, 2017

(65) Prior Publication Data
US 2019/0203232 A1    Jul. 4, 2019

Related U.S. Application Data

(60) Provisional application No. 62/342,737, filed on May 27, 2016.

(51) Int. Cl.
| | |
|---|---|
| *C12P 5/00* | (2006.01) |
| *C12N 1/12* | (2006.01) |
| *C12N 9/10* | (2006.01) |
| *C12N 9/88* | (2006.01) |
| *C07C 13/20* | (2006.01) |
| *C07C 13/23* | (2006.01) |

(52) U.S. Cl.
CPC .............. *C12P 5/007* (2013.01); *C12N 1/12* (2013.01); *C12N 9/1085* (2013.01); *C12N 9/88* (2013.01); *C07C 13/20* (2013.01); *C07C 13/23* (2013.01); *C12Y 402/03051* (2013.01)

(58) Field of Classification Search
None
See application file for complete search history.

(56) References Cited

U.S. PATENT DOCUMENTS

| | | | | |
|---|---|---|---|---|
| 5,518,897 | A * | 5/1996 | Stevens, Jr. ............ | A01N 63/00 435/69.1 |
| 2014/0370562 | A1 | 12/2014 | Melis et al. | |
| 2015/0010978 | A1 | 1/2015 | Heaps et al. | |

FOREIGN PATENT DOCUMENTS

| | | |
|---|---|---|
| WO | 2013119644 A1 | 8/2013 |
| WO | 2016210154 A1 | 12/2016 |

OTHER PUBLICATIONS

F.K. Bentley et al. "Paradigm of Monoterpene (β-phellandrene) Hydrocarbons Production via Photosynthesis in Cyanobacteria", Bioenerg. Res. 6:917-929. (Year: 2013).*
M. Muto et al. "Accumulation and processing of a recombinant protein designed as a cleavable fusion to the endogenous Rubisco LSU protein in Chlamydomonas chloroplast", BMC Biotechnology 9:26 1-11 (Year: 2009).*
A.L. Schilmiller et al. "Monoterpenes in the glandular trichomes of tomato are synthesized from a neryl diphosphate precursor rather than geranyl diphosphate", PNAS 106(26): 10865-10870. (Year: 2009).*
D.E. Hall et al. "Transcriptonne resources and functional characterization of monoterpene synthases for two host species of the mountain pine beetle, lodgepole pine (*Pinus contorta*) and jack pine", BMC Plant Biology 13:80 1-14. (Year: 2013).*
International Search Report and Written Opinion from PCT/US2017/34754, dated Sep. 13, 2017, 10 pages.
Formighieri, et al., "A phycocyanin phellandrene synthase fusion enhances recombinant protein expression and beta-phellandrene (monoterpene) hydrocarbons production in *Synechocystis* (cyanobacteria)," Metabolic Engineering, 2015, vol. 32, pp. 116-124.
Formighieri, et al., "Sustainable heterologous production of terpene hydrocarbons in cyanobacteria," Photosynth Res, 2016, 13 pages.
European Application No. 17803696.8, Supplementary Partial European Search Report dated Feb. 25, 2020, 17 pages.
Formighieri, C & Melis, A., "Cyanobacterial production of plant essential oils," Planta, vol. 248, No. 4, Jul. 4, 2018, pp. 933-946.
European Application No. 17803696.8, Supplementary European Search Report dated Jun. 25, 2020, 15 pages.
Bentley, et al., "Paradigm of Monoterpene (beta-phellandrene) Hydrocarbons Production via Photosynthesis in Cyanobacteria," Bioenergy Research, vol. 6, No. 3, Mar. 2013, pp. 917-929.

* cited by examiner

*Primary Examiner* — Rebecca E Prouty
(74) *Attorney, Agent, or Firm* — Kilpatrick Townsend & Stockton LLP

(57) ABSTRACT

This invention provides compositions and methods for providing high product yield of transgenes expressed in cyanobacteria and microalgae.

8 Claims, 14 Drawing Sheets

Specification includes a Sequence Listing.

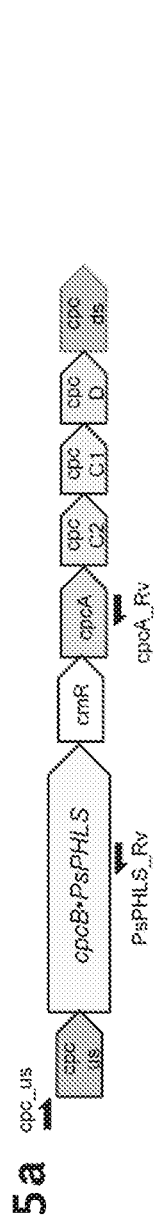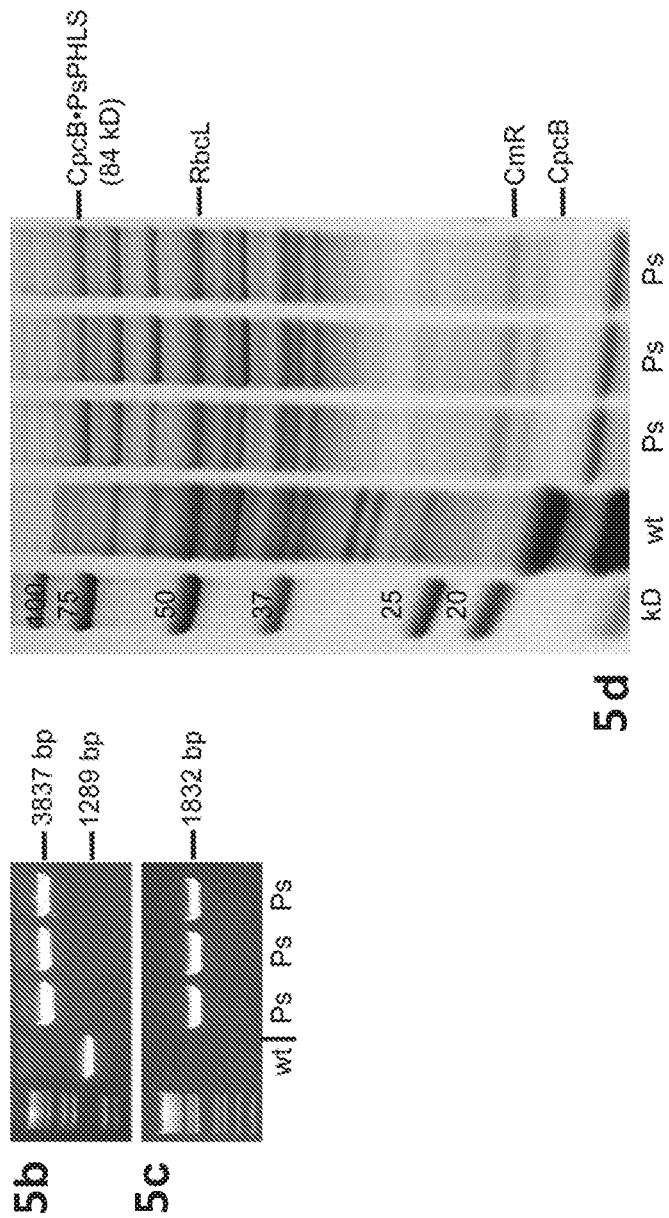
Fig. 5a-5d

Fig. 9a

| | | |
|---|---|---|
| L.angustifoliaADQ73631.1 | -------------------------------------------------- | |
| P.sitchensisADZ45506.1 | -------------------------------------------------- | |
| A.grandisAAF61453.1 | -------------------------------------------------- | |
| P.banksianaAFU73854.1 | -------------------------------------------------- | |
| S.lycopersicumACO56896.1 | CSHSTTSSMNGFEDARDRIRRSPGKLELSPSSYDTAWVAMVPSRHSLNEP | 50 |

| | | |
|---|---|---|
| L.angustifoliaADQ73631.1 | --------------------------------------CSLQVSDPI | 9 |
| P.sitchensisADZ45506.1 | ---------------------------------------SSPVS-D | 5 |
| A.grandisAAF61453.1 | ---------------------------------------SITTAVS-D | 8 |
| P.banksianaAFU73854.1 | ------------------------------------VSSTASVSND | 10 |
| S.lycopersicumACO56896.1 | CFPQCLDWIIENQREDGSWGLNPTHPLLIKDSLSSTLACLLALTKWRVGD | 100 |

| | | |
|---|---|---|
| L.angustifoliaADQ73631.1 | P-TGRRSGGYPPALWDFDTIQSLN--------------------- | 32 |
| P.sitchensisADZ45506.1 | DGVQRRTGGYHSNLWNDDIIQFLS--------------------- | 30 |
| A.grandisAAF61453.1 | DGLQRRTGDYREWLWDDDFIQSLS--------------------- | 32 |
| P.banksianaAFU73854.1 | DGVRREVGDYKYMHWDEDLIDSLA--------------------- | 34 |
| S.lycopersicumACO56896.1 | EQIKKGLGFIETYGWAVDNKDQISPLGFEVIFSSMIKSAEKLDLNLPLNL | 150 |
| | *   *   :   :   :: | |

| | | |
|---|---|---|
| L.angustifoliaADQ73631.1 | ------TEYKGERHMRREEDLIGQVREMLVHEVE---------- | 60 |
| P.sitchensisADZ45506.1 | ------TTYGEPAYRERGERLIDEVKNMFNSISMEDVE-FSP-- | 65 |
| A.grandisAAF61453.1 | ------TPYGEPSYRERAEKLIGEVKEMFNSMPSEDGESMSP-- | 68 |
| P.banksianaAFU73854.1 | ------TSYEAPSYLKRADTIVEAIKDRFNSMGVDDGERMSP-- | 70 |
| S.lycopersicumACO56896.1 | HLVNLVKCKRDSTIKRNVEYMGEGVGELCDWKEMIKLHQRQNGSLFDSPA | 200 |
| | .   :   :  .   : | |

Fig. 9b

```
L.angustifoliaADQ73631.1    ------------------------------------------------------------
P.sitchensisADZ45506.1      ------------------------------------------------------------
A.grandisAAF61453.1         ------------------------------------------------------------
P.banksianaAFU73854.1       ------------------------------------------------------------
S.lycopersicumACO56896.1    TTAAALIYHQHDQKCYQYLNSIFQQHKNWVPTMYPTKVHSLLCLVDTLQN L.angustifoliaADQ73631.1    LGISCHFENEILQIIKSYILNQNYKR------DLYSTSLAFRLLRQ
P.sitchensisADZ45506.1      LGIDRHFKNEIKSTILDYVYSYWTQKGIGCGIESVVPDLNSTALGLRTLRL
A.grandisAAF61453.1         LGIDRHFKKEIKSALDYVYSYWNEKGIGCGRDSVFPDVNSTASGFRTLRL
P.banksianaAFU73854.1       LGIDREHFQNEIKSALDYVFSYWKEKGIGRGRQSAVTDLNSTALGLRTLRL
S.lycopersicumACO56896.1    LGVHRHFKSEIKKALDEIYRLMQQKNE----QIFSNVTHCAMAFRLLRM L.angustifoliaADQ73631.1    YGFILPQEVFDCFKNEEGTDFKPSFGR--DIKGLLQLYEASFLSRKGEET
P.sitchensisADZ45506.1      HGYPVSAEVLKHFQNQNGQFACSPSETEGEMRSIVNLYRASLIAFPGEKV
A.grandisAAF61453.1         HGYSVSSEVLKVFQDQNGQFAFSPSTKERDIRTVLNLYRASFIAFPGEKV
P.banksianaAFU73854.1       HGYPVSSDVLENFKDHNGQFTCSGIQTEGEIRGVLNLFRASLIAFPGEKV
S.lycopersicumACO56896.1    SYYDVSSDELAEFVDEEHFFATNGKYK--SHVEILELHKASQLAIDHEKD L.angustifoliaADQ73631.1    LQLAREPATK------ILQKEVDERE------FATKMEFPSHWTVQMPNARP
P.sitchensisADZ45506.1      MEEAEIFSTK---YIKEALQKIPVSSLSREIGDVLEQDWHTNLPRLEARN
A.grandisAAF61453.1         MEEAEIFSSR---YIKEAVQKIPVSSLSQEIDYTLEYGWHTNMPRLETRN
P.banksianaAFU73854.1       MEEAEIFSTM---YIKHALQKIAVSSLSQEIEYLLEYGWHTNPPRLEARM
S.lycopersicumACO56896.1    DILDKINNWTRAFMEQKLLNNGFIDRMSKKEVRLALRKFYTTSHLAENRR
```

Fig. 9c

```
L.angustifoliaADQ73631.1   FIDAYRRRP--------------DMNPVVLELAILDTNIVQAQFQEELKETS 240
P.sitchensisADZ45506.1     YIDVFGQDT------KDTKL-YMKTEKLLELAKLEFNIFQSLQKTELDSLL 272
A.grandisAAF61453.1        YLDVFGHPTSPWLKKKRTQ-YLDSEKLLELAKLEFNIFHSLQQKELQYLS 280
P.banksianaAFU73854.1      YMEVFPQDT---------IYEQKIVELAKVEFNIFHSLQKRELQSLT 271
S.lycopersicumACO56896.1   YIKSYEENNFKILKAAYRSPNINNKDLLAPSIHDFELCQAQHREELQQLK 443
                            :*.:     .   :     :.    :  ::   :  :   ::

L.angustifoliaADQ73631.1   RWWESTGIVQELPFVRDEIVEGYFWTIGVTQRREHGYERIMTAKVIALVT 290
P.sitchensisADZ45506.1     RWWKDSGFH-HITFSRHLHVEYTTLASCIATEPQHSRFRLGFAKACHVIT 321
A.grandisAAF61453.1        RWWIHSGLP-ELITFGRRRHVEYTTLSSCIATEPKHSAFRLGFAKTCHLIT 329
P.banksianaAFU73854.1      RWWKHYGFP-QLSFTRHIHVEYTTFGSCIATDPKQSAFRLCFAKMSYFVT 320
S.lycopersicumACO56896.1   RWFEDYRLD-QLGLAERYIHASYLFGVTVIPEPELSDARLMYAKYVMLLT 492
                           **.    :     : :.*::  .  :  *  .   *  *   : .:

L.angustifoliaADQ73631.1   CLDDIYDVYGTIEELQLFTSTIQRWDLES-MKQLPTYMQVSFLALHNFVT 339
P.sitchensisADZ45506.1     ILDDMYDVYFGTIDELELFTAQIKRWDPSA-TDCLPKYMKRMYMILYDMVN 370
A.grandisAAF61453.1        VLDDIYDTFGTMDEIELFNEAVRRWNPSE-KERLPEYMKEIYMALYEALT 378
P.banksianaAFU73854.1      VLDDIYDTYGTMEELELFTAAIKRWDPSV-VDCLPEYMKGVYMAVYDTVN 369
S.lycopersicumACO56896.1   IVDDHFESFASKDECFNIIELVERWDDYASVGYKSEKVKVFFSVFYKSIE 542
                            :** :: :::..  . :*   :   .     *         :  .

L.angustifoliaADQ73631.1   EVAVDTLKKKGYNSTPYLEKTWDLVESYIKE-ATWYYNGIYKPSMQEYILN 388
P.sitchensisADZ45506.1     EMSREAETAQGRDTLNYARQAWEDFIDSYMQE-AKWIATGYLPTFDEYFFE 419
A.grandisAAF61453.1        DMAREARKTQGRDTLNYARKAWEVYLDSYTQE-AKWIASGYLPTFEERYLE 427
P.banksianaAFU73854.1      EMAKEAEKVQGRDTLNYVRQAWELYIDAYMPE-AKWISSGYLPTFQEYLD 418
S.lycopersicumACO56896.1   ELATIAEIKQGRSVKNHLINLWLELMKLMLMERVEWCSGKTIPSIEEYLY 592
                           :                        .            :::**:
```

Fig. 9d

| | | |
|---|---|---|
| L.angustifoliaADQ73631.1 | NAWISVGSMAILNHLFFRFTN-----ERMHKYRDMWKYSNIVRLADD | 431 |
| P.sitchensisADZ45506.1 | NGKVSSGHRVAALQPILTMDIPFPHDILKEVDFPSKLMDLASAILRLRGD | 469 |
| A.grandisAAF61453.1 | NAKVSSGHRAAALTPLLTLDVPLPDDVLKGIDFPSRFMDLASSFLRLRGD | 477 |
| P.banksianaAFU73854.1 | NSKISPGTRITILQPILTLGEPLPHEILQEIDFPAKFWDLISVILRKGD | 468 |
| S.lycopersicumACO56896.1 | VTSITFCAKLIPLSTQYFLGIKISKDLLESDEICG-LWNCSGRVMPLLMD | 641 |
| | :  : | |
| L.angustifoliaADQ73631.1 | MGTSLAEVERGDVPKAIQCYMNET-NASEEEAREYVRRVIQEEWEKLNTE | 480 |
| P.sitchensisADZ45506.1 | TRCYRADRARGEEASCISCYMKDNPGATEEDALSHINAVISDVIKGLNWE | 519 |
| A.grandisAAF61453.1 | TRCYKADRDRGEEASSISCYMKDNPGLTEEDALNHINAMINDIIKELNWE | 527 |
| P.banksianaAFU73854.1 | TRCYEADRARGEEASSVSCYMKDNAGITEEDAIHCINDMVNNLLKELNWE | 518 |
| S.lycopersicumACO56896.1 | LQDSK----RRQKEVSINLVTLLMKSMSEEEAIMKIKEILEMNRRELLKM | 687 |
| | *    :.:**.*  .::::. ::*:   * | |
| L.angustifoliaADQ73631.1 | LMRDDDDDDFTLSKYYCEVVANLTRMAQFIYQDGSDGFGMKDSKVNRLL | 530 |
| P.sitchensisADZ45506.1 | LLNPNS-----SVPISSKKHVFPDVSRALHYGYKYR-DGYSVSNIETKSLV | 563 |
| A.grandisAAF61453.1 | LLKPDS----NIPMTARKHAYEITRAPHQLYKYR-DGFSVATQETKSLV | 571 |
| P.banksianaAFU73854.1 | LLKPDS----NVPISCRKAAFDICRIFHHGYKYR-DGYGDATIEVKNLV | 562 |
| S.lycopersicumACO56896.1 | VLVQKKGS---QLFQLCKDIFWRTSKWAHFTYSQT-DGYRIA-EEMKNHI | 732 |
| | . .       .    . * . *.. .  .   : | |
| L.angustifoliaADQ73631.1 | KETLIERYE- | 539 |
| P.sitchensisADZ45506.1 | MRTILLESVPF | 573 |
| A.grandisAAF61453.1 | RRTVLEPVPL | 581 |
| P.banksianaAFU73854.1 | KRTVLEPVPL | 572 |
| S.lycopersicumACO56896.1 | DEVFYKPLNH | 742 |
| | . | |

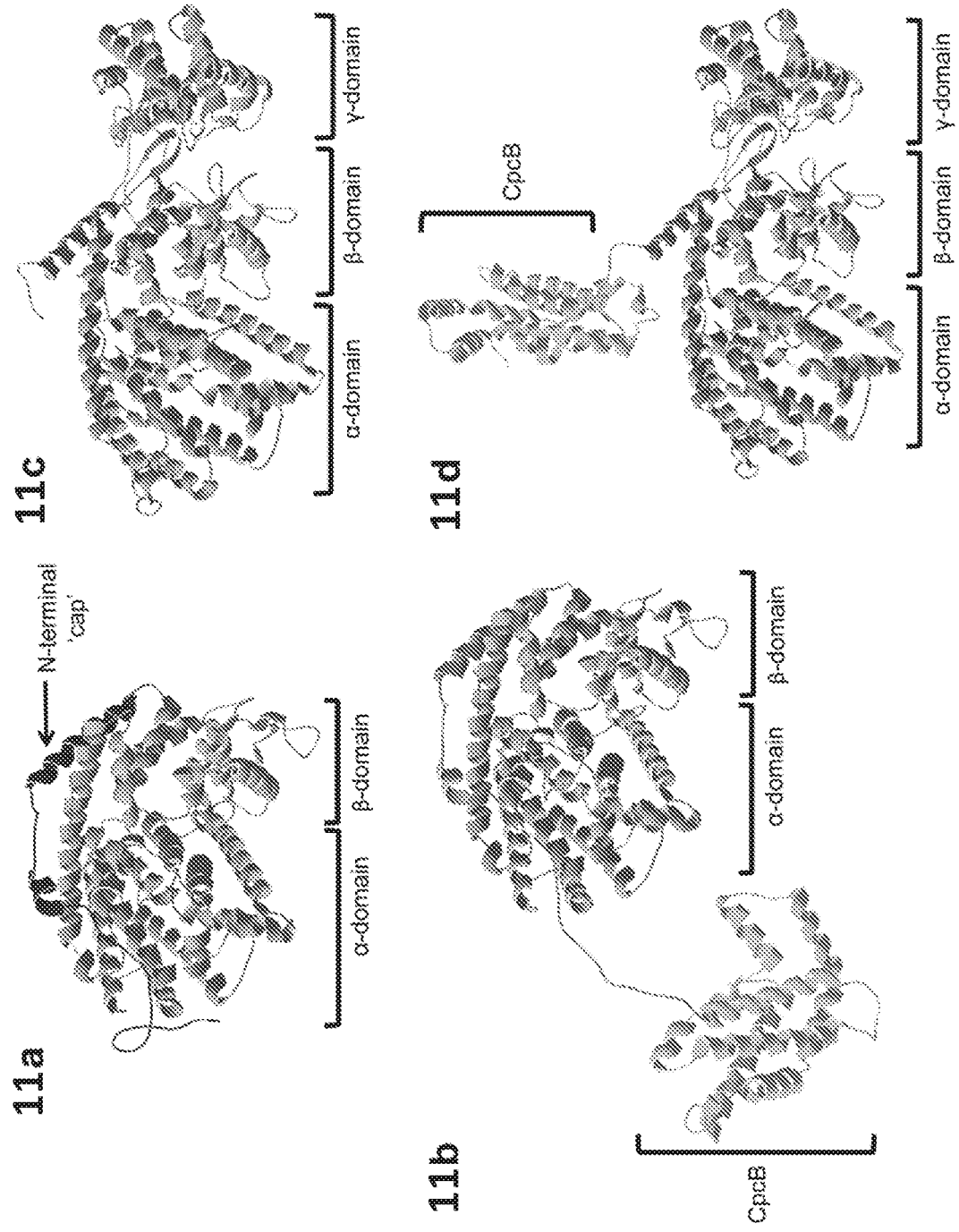

SEQUENCE LISTING

<160> NUMBER OF SEQ ID NOS: 48

<210> SEQ ID NO 1
<211> LENGTH: 1632
<212> TYPE: DNA
<213> ORGANISM: Lavandula angustifolia

<400> SEQUENCE: 1

```
catatgtgta gtttgcaagt ttctgatcct attcctaccg gacgccgttc cggtggttat      60
cccccggcct tatgggattt cgatactatt caatccctga ataccgaata taagggcgaa     120
cgtcacatgc gtcgggaaga agacttaatt ggtcaagttc gggaaatgtt ggtgcacgaa     180
gtagaagatc ccactcccca gttggaattc attgacgatc tgcataaatt gggcatttcc     240
tgccattttg aaaacgagat tctgcaaatt ctcaaatcca tttatctcaa ccaaaactat     300
aaacgggacc tctattctac cagtttagcc ttccgtctct tgcgtcaata cgggtttatc     360
ttgccgcagg aagttttga ctgctttaaa aacgaagaag gtacggattt taaacccagc     420
ttcggccggg atattaaggg tctgttacag ttgtacgaag cctccttttt gtcccggaag     480
ggggaagaaa ctttacaact cgcccgcgaa tttgctacca aaatcttgca aaaggaagtc     540
gatgaacggg aatttgctac taaaatggaa tttcccagtc actggaccgt acaaatgcct     600
aacgctcggc cttttatcga tgcctatcgt cggcgtcccg acatgaaccc cgtggttctg     660
gaactcgcca ttctcgatac caatatcgtg caagctcagt ttcaagaaga attgaaggag     720
acctcccgtt ggtgggaaag cacggggatt gttcaagaac tgccgtttgt tcggaccgg     780 attgtggaag gttattttg gaccattggt gttactcaac gccgtgaaca cggttacgaa     840
```

```
cgtattatga cggccaaagt catcgctttg gtgacctgtt tggatgatat ttatgacgta      900
tatggcacta ttgaagaatt gcaactcttc acctctacga ttcagcgttg ggatttggag      960
tctatgaagc agttaccgac ttatatgcag gtaagcttcc tggccttgca caattttgta     1020
accgaagtgg cctatgatac gctgaagaaa aagggctaca actctacccc ctatttgcgg     1080
aagacttggg tggatttggt cgaaagttac attaaggaag ccacttggta ctataatggg     1140
tacaaaccct ctatgcagga atacctcaac aacgcctgga tctctgtggg cagcatggct     1200
attttgaatc atttgttttt tcgctttact aatgaacgca tgcataagta ccgggacatg     1260
aatcgtgtat cctctaatat tgtgcggtta gccgacgata tgggaacctc tttggccgaa     1320
gttgaacgcg gtgacgtgcc caaagctatc caatgttaca tgaatgaaac gaacgcctct     1380
gaggaggagg cccgcgaata tgtgcggcgc gttatccagg aagaatggga aaaactgaac     1440
actgaactga tgcgcgacga cgacgatgac gatgatttca ccttaagtaa atactactgc     1500
gaagtcgttg ctaacctgac ccggatggct cagttcattt accaagatgg ttccgatggg     1560
tttgggatga agattccaa agtaaatcgt ttactgaaag aaacgctgat tgagcgctat     1620
gagtgaagat ct                                                         1632
```

<210> SEQ ID NO 2
<211> LENGTH: 2240
<212> TYPE: DNA
<213> ORGANISM: Solanum lycopersicum

<400> SEQUENCE: 2

```
catatgtgct cccattctac cacctcgtcc atgaatggtt ttgaagatgc ccgggatcga       60
atccgtgaaa gtttcggaaa actggaattg tctcccagta gctatgatac cgcgtgggta      120
gccatggttc caagccgtca ttctctgaat gaaccctgct tcccacagtg cctggattgg      180
attattgaaa atcagcggga agatggctct tgggtctaa accccaccca tccccttctg      240
cttaaagact ccttatcctc aaccttagct tgtttattgg cactcacaaa gtggcgtgtc      300
ggcgacgaac aaattaagcg gggactgggg tttattgaaa cctacggatg gccgtggac      360 aacaaggatc aaatttcccc gctaggcttt gaagtcattt ttagtagcat gattaagtcc      420
gcagaaaagt tggacttgaa tcttcccctg aacttgcact tagtcaatct agtcaaatgc      480
aaacgggata gcaccattaa acggaatgta gaatatatgg agaaggcgt aggtgaattg      540 tgtgactgga aagagatgat taagctgcac caacgtcaaa atgggagtct gtttgacagc      600
cctgccacta ctgccgccgc cttgatctac caccagcacg atcaaaagtg ttatcaatac      660
ttgaatagta tctttcaaca acataaaaac tgggtgccca ctatgtaccc cacaaaagtt      720
catagtttat tatgtttagt tgatacatta caaaatctgg gggtgcatcg tcattttaaa      780
agtgaaatta aaaagcgtt ggacgaaata taccgtttat ggcaacaaaa aatgaacag      840 atttttagca atgtgacca ttgcgccatg gcttttcgac ttctgagaat gagttattac      900
gatgttagtt cagatgagct ggctgagttt gtagatgaag acattttttt tgcgactaac      960
gggaaataca aatcccacgt tgaaattta gaactccata agcgtctca attggcaatt     1020 gaccatgaaa aagacgatat tttggacaaa ataacaact ggacgcgcgc gtttatggaa     1080
caaaaactcc taaacaacgg ctttattgac cgcatgagta aaaaggaagt tgaattggcc     1140
ttacgcaaat tttacaccac tagtcacctc gcagaaaacc gtcgctatat caaaagttat     1200
gaagagaata acttcaaaat tttaaaagcg gcctaccgga gtcccaacat taataataaa     1260
```

```
gacttacttg ctttctccat ccatgatttt gaattatgcc aagcccagca ccgggaagaa   1320
ttacagcaat tgaagagatg gtttgaagat taccggttgg atcaattagg cttagccgaa   1380
cgttatattc acgcaagtta tctttttgga gttaccgtga tcccggagcc cgagttatcc   1440
gatgcaagat tgatgtacgc gaaatacgtc atgcttctaa ccatcgttga tgatcacttt   1500
gaatcctttg cgtcgaaaga tgaatgtttc aacatcattg aattagttga gcgttgggac   1560
gattacgctt ccgttggcta caagtccgaa aaggtgaaag tgtttttcag tgtttttttac  1620
aaaagtattg aagaactagc caccattgct gaaatcaaac aaggccggag tgtaaaaaat   1680
cacctgatta atctgtggtt ggaattgatg aaacttatgc ttatggaacg cgttgaatgg   1740
tgtagcggaa aaacgattcc gagtattgaa gaatatctgt acgttacctc tatcactttt   1800
tgtgctaagt tgatccccct atctacccaa tactttctcg gtattaaaat aagcaaagac   1860
ctcttggaga gtgatgaaat ttgtggtctc tggaactgct ccgggcgtgt gatgcgtatt   1920
ttgaacgatt tgcaggatag caaacgtgag caaaaagaag ttagtattaa tctcgtaact   1980
ttactaatga aatccatgag cgaggaagaa gctatcatga aaattaaaga aattttggaa   2040
atgaatcgcc gtgagctatt aaagatggtt cttgtccaga agaaaggttc ccaacttccc   2100
caattgtgca aagatatttt ttggcgcaca agtaagtggg cccatttcac ctactcgcaa   2160
accgatgggt atcggatagc cgaagaaatg aagaatcaca ttgacgaagt gttttataaa   2220
ccgttaaacc actagagatc                                               2240

<210> SEQ ID NO 3
<211> LENGTH: 797
<212> TYPE: DNA
<213> ORGANISM: Solanum lycopersicum

<400> SEQUENCE: 3
gatcttcaca ttctaacggg agataccaga acaatggcta gccttaatct acaaacggaa     60
aaactgtgtt acgaggacaa cgataacgat ctggatgaag aattgatgcc caaacacatc    120
gctttgatta tggatgggaa tcgtcgctgg gccaaagata agggactaga agtctatgag    180
ggccataagc atattattcc aaaattaaaa gaaatctgtg atatctcatc taagttaggc    240
attcagatta ttaccgcctt tgcattcagt actgagaact ggaaacgttc caaagaagaa    300
gtcgactttt tgctccagat gtttgaagaa atctatgatg agttcagccg ctctggtgtt    360
agagtcagca ttattggttg caaaagtgac ttacccatga ccttgcaaaa gtgtattgct    420
ttaacggagg agaccaccaa agggaataag ggtttacacc tagtgatcgc cctaaactac    480
gggggctatt acgatatcct gcaggccacc aaatccatcg taaacaaagc catgaatggc    540
ctcttagatg tggaagacat taataaaaac ttgtttgacc aggaattaga atccaaatgt    600
ccgaatccgg acctgttgat tcgcacgggc ggcgaacagc gcgtctccaa tttttactg     660
tggcaactag cgtatactga attttatttt accaatacat tgtttcctga cttcggggaa    720
gaagacttga aagaagcgat tatgaacttc cagcagaggc atcgacgttt tggagggcat    780
acttattagg cggccgc                                                   797

<210> SEQ ID NO 4
<211> LENGTH: 1731
<212> TYPE: DNA
<213> ORGANISM: Pinus banksiana

<400> SEQUENCE: 4
catatggtca gtagcacagc cagtgtttca aatgatgatg gagtgcggag acgcgtgggc     60
```

```
gattatcgat acaatcactg ggatgaagac ctgatcgatt ccttggccac ctcatacgaa    120
gctccttcct atttgaaacg tgcggatacg ctcgtcgaag cgattaaaga tcggtttaat    180
agtatgggtg tagatgatgg ggaaagaatg tctccattaa ctgatctcta tcaacgactg    240
tggatggtag atagtgtcga acgtttgggt atagatcgcc atttccaaaa tgagattaaa    300
agcgccttgg actatgtgtt ttcttattgg aaagagaaag gcatcggtcg tggccgccaa    360
agcgctgtta ccgatctgaa ttccaccgcc ctgggcttac gtactttacg actgcacggg    420
taccccgtgt catccgatgt gttggaaaat tttaaagatc ataacggtca gtttacgtgt    480
agcggcattc aaacagaagg tgagattaga ggcgtgttaa cttgtttcg tgctagtctt    540
atcgccttcc ccggcgaaaa agtcatggaa gaagccgaaa ttttttccac tatgtatctt    600
aaacatgcct tgcaaaaaat tgcggtgtcc agtctgtctc aggaaatcga atacttactg    660
gagtatggct ggcataccaa cccgcctcgc ctggaagcgc gcatgtatat ggaagtattt    720
ccccaagaca ccatctacga acagaaatta gtggaactgg ctaaagtgga gttcaatatc    780
tttcattctc tacagaagcg tgaactgcag tctttgaccc gatggtggaa acattatggg    840
ttcccccaat taagttttac tagacatata catgtagagt attacacatt tggtagctgt    900
atagccactg atccgaaaca atcggcattt cggctctgtt ttgccaaaat gtcatatttc    960
gtaaccgtgc tagatgatat ctacgacacg tatggaacca tggaggaact ggaattgttt   1020
actgccgcca ttaaacgctg gacccctcc gttgtcgatt gtttaccgga gtatatgaaa   1080
ggtgtatata tggccgtttta cgataccgta acgaaatgg cgaaggaggc ggaaaaagta   1140
caaggtcgtg atacgctaaa ctacgtgcgc caggcctggg aactctatat cgacgcttat   1200
atgccggaag ccaaatggat ttcaagtggc tacctgccca cttttcaaga atacctcgat   1260
aattcgaaaa tctctttttgg cactcggatc accattcttc aaccaatttt aacgttgggt   1320
gagcccctgc cgcacgaaat tctacaggag attgactttc ctgccaagtt taatgatcta   1380
atttccgtga ttctacggtt aaagggcgac accaggtgtt acaaagccga tcgagcgcga   1440
ggcgaggagg catcgtccgt ctcctgctat atgaaagata cgcggggat aaccgaagaa   1500
gatgccattc actgcattaa tgatatggtt aataatctgc tgaaagagtt gaactgggaa   1560
ctgctgaaaac ccgacagtaa cgtgcccatc agttgccgga aagcggcctt cgatatttgt   1620
aggattttc atcacggata caaatatcgg gatggctatg cgacgcaac tattgaagtt   1680
aaaaatttgg tcaaacgcac cgtattagaa cccgttcccc tgtagagatc t           1731
```

<210> SEQ ID NO 5
<211> LENGTH: 1734
<212> TYPE: DNA
<213> ORGANISM: Picea sitchensis

<400> SEQUENCE: 5

```
catatgtcca gccctgtgtc tgatgacgga gttcaaagac ggacgggtgg ctaccattcc     60
aacttatgga atgatgatat tattcaattt ttaagtacga cttatggtga acctgcctat    120
cgagaacgag cgaacgcctt gattgatgaa gttaaaaata tgtttaattc gatttctatg    180
gaagatgttg agttttcacc actgaatgac ttgatccagc gtctgtggat cgtcgattcc    240
gtcgaacgtt tggggatcga tcgccatttt aaaaacgaaa ttaagtcaac cctcgactat    300
gtttactcct actggacgca gaagggcata gggtgtggca tcgaaagcgt agtaccagac    360
ttaaacagta cggcactggg attgcgcacg ctccgtcttc atggatatcc tgtaagcgct    420
```

-continued

```
gaagtcctta aacacttcca aaatcaaaat ggtcagtttg cctgtagccc gtcagagacg      480
gaaggcgaaa tgcggtccat tgtaaactta tatcgggctt ccttaattgc atttcccggc      540
gaaaaagtga tggaagaagc cgaaattttt tccacgaaat acttgaagga agcactgcag      600
aaaattcccg taagtagcct gagccgtgaa atcggggatg tattggaaca agactggcat      660
actaacttgc cacgattaga agctcgaaat tacattgatg tcttcggtca agatactaaa      720
gatacgaaac tgtacatgaa aaccgagaaa cttctggaat tagctaaaact tgaattcaac      780
atttttcagt cactccaaaa aacggaactg gactccttgt tgcgctggtg gaaagatagt      840
ggctttcatc atatcacctt tccccgacat ctacatgtgg aatattacac attggcctcg      900
tgtatcgcca ttgagcccca gcactctaga tttcgccttg gctttgccaa agcgtgtcat      960
gtgataacca tcctggatga catgtacgat gttttttggca ccatcgatga gttagagctt     1020
tttaccgcac agattaagcg ctgggacccg tcagctaccg attgtttgcc caaatatatg     1080
aaacgcatgt atatgatctt atacgatatg gtgaacgaaa tgtctcgtga agccgaaacc     1140
gcccagggaa gggatacccct taattacgcc agacaagcct gggaagattt tatcgattcc     1200
tatatgcagg aagcaaagtg gatcgctacc gggtaccttc ccacgttcga tgagtacttc     1260
gagaacggta aggtttcctc cggccatcgt gttgccgcgt tgcagcccat ccttacaatg     1320
gatatcccct ttccccatga catattgaaa gaagttgatt ttccgtccaa actcaatgat     1380
ctagcctctg ccatcttgcg tctacgcggc gatacgaggt gttataaagc cgaccgtgct     1440
cgtggtgaag aggcctcctg catttcctgt tatatgaaag acaacccggg cgctactgag     1500
gaggacgctt tgagccatat taacgcggtg atatccgatg tcattaaagg attaaactgg     1560
gaactactca atcccaatag ttccgtgccg atttcgtcaa aaaagcacgt ttttgacgtg     1620
tcgcgcgctc tgcactatgg atataagtat cgtgatgggt atagcgtgtc aaatattgaa     1680
acaaagtcat tggtcatgag aactctccta gaatcagtac cattttagag atct           1734
```

<210> SEQ ID NO 6
<211> LENGTH: 1758
<212> TYPE: DNA
<213> ORGANISM: Abies grandis

<400> SEQUENCE: 6

```
catatgtcct tgaccacagc cgtgagcgat gatgggctgc agagaagaat tggcgactat       60
cattccaatt tgtgggatga cgattttata caatcccttt cgacaccgta tggagaacct      120
agttaccgtg aacgcgccga aaagctgatt ggagaagtaa agaaatgtt taattccatg       180
ccctccgagg atggtgaaag tatgagtcct ctcaacgact tgattgaacg tttgtggatg      240
gtggattccg tcgagcgctt gggaattgac cgtcattta aaaagaaat taagagcgct       300
ttggactatg tgtacagcta ttggaatgag aaaggcattg gttgcggccg agatagcgtt      360
tttccagatg tgaatagtac tgctagcgga tttcggactt tgcggctaca tggctattcc      420
gtatctagcg aggtgttaaa ggtattccaa gatcaaaatg gtcagttcgc atttccccct      480
agtaccaaag agcgcgacat acgcactgtc ctaaacctct accgggcctc attcatcgcc      540
tttccaggtg agaaagtaat ggaagaggct gaaattttta gtagtcgcta tttgaaagaa      600
gctgtgcaaa agatccccgt tagtagcctc agtcaagaaa ttgactatac tttggaatat      660
gggtggcata ccaatatgcc tcggttggaa actcgcaatt acctagacgt gtttggccac      720
cccacttcac cgtggttaaa aaagaaacgc acacaatatc tagacagtga aaactcctg      780
gaattagcta agctagaatt caatatcttt cattcattac aacaaaagga gttacaatat      840
```

-continued

```
ctgtcccgat ggtggattca ctcaggcctg ccggaattga cgtttggtcg acatcggcat    900
gtcgaatact acaccctctc tagctgtatt gccaccgagc ccaagcatag tgcttttcgc    960
ctcgggttcg ccaagacttg tcacctaatt accgttttgg atgatatcta cgatacgttt   1020
ggaacgatgg atgagatcga attgtttaat gaagcagttc ggcggtggaa tccttctgag   1080
aaagaacggc tccccgaata tatgaaggag atatatatgg cactttacga agctctgacc   1140
gacatggcac gtgaggccga aaaaactcag gccgtgaca ctctgaacta cgcgcgtaaa    1200
gcttgggaag tttacctcga ttcatatacc caggaggcga agtggatcgc ttccgggtat   1260
ttgcccacct tcgaagagta ccttgaaaat gccaaagtta gttccggtca ccgggctgcg   1320
gcacttaccc cgttattaac cctcgacgtc cccttgccgg atgatgtgct gaaaggcatt   1380
gactttccct cccgttttaa cgacttagcg tctagcttct tgcggctccg gggtgacacc   1440
cgctgttata aagccgatcg cgatcgagga gaggaagcca gttcaatctc ttgttatatg   1500
aaggataatc cgggcctaac cgaagaagat gcgctcaatc atattaatgc gatgattaac   1560
gacataatta aggaattaaa ctgggaattg ttgaaaccag attccaacat tccgatgaca   1620
gctcgcaaac acgcgtatga aattacgcgc gcttttcatc aactctacaa atatcgcgat   1680
ggattcagcg ttgccactca agaaaccaaa agccttgttc ggcgtaccgt attagaacca   1740
gtgcccttat agagatct                                                1758
```

<210> SEQ ID NO 7
<211> LENGTH: 539
<212> TYPE: PRT
<213> ORGANISM: Lavandula angustifolia

<400> SEQUENCE: 7

```
Cys Ser Leu Gln Val Ser Asp Pro Ile Pro Thr Gly Arg Arg Ser Gly
1               5                   10                  15

Gly Tyr Pro Pro Ala Leu Trp Asp Phe Asp Thr Ile Gln Ser Leu Asn
            20                  25                  30

Thr Glu Tyr Lys Gly Glu Arg His Met Arg Arg Glu Glu Asp Leu Ile
        35                  40                  45

Gly Gln Val Arg Glu Met Leu Val His Glu Val Glu Asp Pro Thr Pro
    50                  55                  60

Gln Leu Glu Phe Ile Asp Asp Leu His Lys Leu Gly Ile Ser Cys His
65                  70                  75                  80

Phe Glu Asn Glu Ile Leu Gln Ile Leu Lys Ser Ile Tyr Leu Asn Gln
                85                  90                  95

Asn Tyr Lys Arg Asp Leu Tyr Ser Thr Ser Leu Ala Phe Arg Leu Leu
            100                 105                 110

Arg Gln Tyr Gly Phe Ile Leu Pro Gln Glu Val Phe Asp Cys Phe Lys
        115                 120                 125

Asn Glu Glu Gly Thr Asp Phe Lys Pro Ser Phe Gly Arg Asp Ile Lys
    130                 135                 140

Gly Leu Leu Gln Leu Tyr Glu Ala Ser Phe Leu Ser Arg Lys Gly Glu
145                 150                 155                 160

Glu Thr Leu Gln Leu Ala Arg Glu Phe Ala Thr Lys Ile Leu Gln Lys
                165                 170                 175

Glu Val Asp Glu Arg Glu Phe Ala Thr Lys Met Glu Phe Pro Ser His
            180                 185                 190

Trp Thr Val Gln Met Pro Asn Ala Arg Pro Phe Ile Asp Ala Tyr Arg
        195                 200                 205
```

Arg Arg Pro Asp Met Asn Pro Val Val Leu Glu Leu Ala Ile Leu Asp
    210             215                 220

Thr Asn Ile Val Gln Ala Gln Phe Gln Glu Glu Leu Lys Glu Thr Ser
225                 230                 235                 240

Arg Trp Trp Glu Ser Thr Gly Ile Val Gln Glu Leu Pro Phe Val Arg
                245                 250                 255

Asp Arg Ile Val Glu Gly Tyr Phe Trp Thr Ile Gly Val Thr Gln Arg
            260                 265                 270

Arg Glu His Gly Tyr Glu Arg Ile Met Thr Ala Lys Val Ile Ala Leu
        275                 280                 285

Val Thr Cys Leu Asp Asp Ile Tyr Asp Val Tyr Gly Thr Ile Glu Glu
    290                 295                 300

Leu Gln Leu Phe Thr Ser Thr Ile Gln Arg Trp Asp Leu Glu Ser Met
305                 310                 315                 320

Lys Gln Leu Pro Thr Tyr Met Gln Val Ser Phe Leu Ala Leu His Asn
                325                 330                 335

Phe Val Thr Glu Val Ala Tyr Asp Thr Leu Lys Lys Lys Gly Tyr Asn
            340                 345                 350

Ser Thr Pro Tyr Leu Arg Lys Thr Trp Val Asp Leu Val Glu Ser Tyr
        355                 360                 365

Ile Lys Glu Ala Thr Trp Tyr Tyr Asn Gly Tyr Lys Pro Ser Met Gln
370                 375                 380

Glu Tyr Leu Asn Asn Ala Trp Ile Ser Val Gly Ser Met Ala Ile Leu
385                 390                 395                 400

Asn His Leu Phe Phe Arg Phe Thr Asn Glu Arg Met His Lys Tyr Arg
                405                 410                 415

Asp Met Asn Arg Val Ser Ser Asn Ile Val Arg Leu Ala Asp Asp Met
            420                 425                 430

Gly Thr Ser Leu Ala Glu Val Glu Arg Gly Asp Val Pro Lys Ala Ile
        435                 440                 445

Gln Cys Tyr Met Asn Glu Thr Asn Ala Ser Glu Glu Glu Ala Arg Glu
    450                 455                 460

Tyr Val Arg Arg Val Ile Gln Glu Glu Trp Glu Lys Leu Asn Thr Glu
465                 470                 475                 480

Leu Met Arg Asp Asp Asp Asp Asp Asp Phe Thr Leu Ser Lys Tyr
                485                 490                 495

Tyr Cys Glu Val Val Ala Asn Leu Thr Arg Met Ala Gln Phe Ile Tyr
            500                 505                 510

Gln Asp Gly Ser Asp Gly Phe Gly Met Lys Asp Ser Lys Val Asn Arg
        515                 520                 525

Leu Leu Lys Glu Thr Leu Ile Glu Arg Tyr Glu
    530                 535

<210> SEQ ID NO 8
<211> LENGTH: 573
<212> TYPE: PRT
<213> ORGANISM: Picea sitchensis

<400> SEQUENCE: 8

Ser Ser Pro Val Ser Asp Gly Val Gln Arg Arg Thr Gly Gly Tyr
1               5                   10                  15

His Ser Asn Leu Trp Asn Asp Asp Ile Ile Gln Phe Leu Ser Thr Thr
            20                  25                  30

Tyr Gly Glu Pro Ala Tyr Arg Glu Arg Gly Glu Arg Leu Ile Asp Glu

-continued

```
                35                  40                  45
Val Lys Asn Met Phe Asn Ser Ile Ser Met Glu Asp Val Glu Phe Ser
 50                  55                  60
Pro Leu Asn Asp Leu Ile Gln Arg Leu Trp Ile Val Asp Ser Val Glu
 65                  70                  75                  80
Arg Leu Gly Ile Asp Arg His Phe Lys Asn Glu Ile Lys Ser Thr Leu
                 85                  90                  95
Asp Tyr Val Tyr Ser Tyr Trp Thr Gln Lys Gly Ile Gly Cys Gly Ile
                100                 105                 110
Glu Ser Val Val Pro Asp Leu Asn Ser Thr Ala Leu Gly Leu Arg Thr
                115                 120                 125
Leu Arg Leu His Gly Tyr Pro Val Ser Ala Glu Val Leu Lys His Phe
130                 135                 140
Gln Asn Gln Asn Gly Gln Phe Ala Cys Ser Pro Ser Glu Thr Glu Gly
145                 150                 155                 160
Glu Met Arg Ser Ile Val Asn Leu Tyr Arg Ala Ser Leu Ile Ala Phe
                165                 170                 175
Pro Gly Glu Lys Val Met Glu Glu Ala Glu Ile Phe Ser Thr Lys Tyr
                180                 185                 190
Leu Lys Glu Ala Leu Gln Lys Ile Pro Val Ser Ser Leu Ser Arg Glu
                195                 200                 205
Ile Gly Asp Val Leu Glu Gln Asp Trp His Thr Asn Leu Pro Arg Leu
                210                 215                 220
Glu Ala Arg Asn Tyr Ile Asp Val Phe Gly Gln Asp Thr Lys Asp Thr
225                 230                 235                 240
Lys Leu Tyr Met Lys Thr Glu Lys Leu Leu Glu Leu Ala Lys Leu Glu
                245                 250                 255
Phe Asn Ile Phe Gln Ser Leu Gln Lys Thr Glu Leu Asp Ser Leu Leu
                260                 265                 270
Arg Trp Trp Lys Asp Ser Gly Phe His His Ile Thr Phe Ser Arg His
                275                 280                 285
Leu His Val Glu Tyr Tyr Thr Leu Ala Ser Cys Ile Ala Ile Glu Pro
                290                 295                 300
Gln His Ser Arg Phe Arg Leu Gly Phe Ala Lys Ala Cys His Val Ile
305                 310                 315                 320
Thr Ile Leu Asp Asp Met Tyr Asp Val Phe Gly Thr Ile Asp Glu Leu
                325                 330                 335
Glu Leu Phe Thr Ala Gln Ile Lys Arg Trp Asp Pro Ser Ala Thr Asp
                340                 345                 350
Cys Leu Pro Lys Tyr Met Lys Arg Met Tyr Met Ile Leu Tyr Asp Met
                355                 360                 365
Val Asn Glu Met Ser Arg Glu Ala Glu Thr Ala Gln Gly Arg Asp Thr
                370                 375                 380
Leu Asn Tyr Ala Arg Gln Ala Trp Glu Asp Phe Ile Asp Ser Tyr Met
385                 390                 395                 400
Gln Glu Ala Lys Trp Ile Ala Thr Gly Tyr Leu Pro Thr Phe Asp Glu
                405                 410                 415
Tyr Phe Glu Asn Gly Lys Val Ser Ser Gly His Arg Val Ala Ala Leu
                420                 425                 430
Gln Pro Ile Leu Thr Met Asp Ile Pro Phe Pro His Asp Ile Leu Lys
                435                 440                 445
Glu Val Asp Phe Pro Ser Lys Leu Asn Asp Leu Ala Ser Ala Ile Leu
450                 455                 460
```

Arg Leu Arg Gly Asp Thr Arg Cys Tyr Lys Ala Asp Arg Ala Arg Gly
465                 470                 475                 480

Glu Glu Ala Ser Cys Ile Ser Cys Tyr Met Lys Asp Asn Pro Gly Ala
                485                 490                 495

Thr Glu Glu Asp Ala Leu Ser His Ile Asn Ala Val Ile Ser Asp Val
            500                 505                 510

Ile Lys Gly Leu Asn Trp Glu Leu Leu Asn Pro Asn Ser Ser Val Pro
        515                 520                 525

Ile Ser Ser Lys Lys His Val Phe Asp Val Ser Arg Ala Leu His Tyr
530                 535                 540

Gly Tyr Lys Tyr Arg Asp Gly Tyr Ser Val Ser Asn Ile Glu Thr Lys
545                 550                 555                 560

Ser Leu Val Met Arg Thr Leu Leu Glu Ser Val Pro Phe
                565                 570

<210> SEQ ID NO 9
<211> LENGTH: 581
<212> TYPE: PRT
<213> ORGANISM: Abies grandis

<400> SEQUENCE: 9

Ser Leu Thr Thr Ala Val Ser Asp Asp Gly Leu Gln Arg Arg Ile Gly
1               5                   10                  15

Asp Tyr His Ser Asn Leu Trp Asp Asp Asp Phe Ile Gln Ser Leu Ser
                20                  25                  30

Thr Pro Tyr Gly Glu Pro Ser Tyr Arg Glu Arg Ala Glu Lys Leu Ile
            35                  40                  45

Gly Glu Val Lys Glu Met Phe Asn Ser Met Pro Ser Glu Asp Gly Glu
        50                  55                  60

Ser Met Ser Pro Leu Asn Asp Leu Ile Glu Arg Leu Trp Met Val Asp
65                  70                  75                  80

Ser Val Glu Arg Leu Gly Ile Asp Arg His Phe Lys Lys Glu Ile Lys
                85                  90                  95

Ser Ala Leu Asp Tyr Val Tyr Ser Tyr Trp Asn Glu Lys Gly Ile Gly
                100                 105                 110

Cys Gly Arg Asp Ser Val Phe Pro Asp Val Asn Ser Thr Ala Ser Gly
            115                 120                 125

Phe Arg Thr Leu Arg Leu His Gly Tyr Ser Val Ser Ser Glu Val Leu
130                 135                 140

Lys Val Phe Gln Asp Gln Asn Gly Gln Phe Ala Phe Ser Pro Ser Thr
145                 150                 155                 160

Lys Glu Arg Asp Ile Arg Thr Val Leu Asn Leu Tyr Arg Ala Ser Phe
                165                 170                 175

Ile Ala Phe Pro Gly Glu Lys Val Met Glu Glu Ala Glu Ile Phe Ser
                180                 185                 190

Ser Arg Tyr Leu Lys Glu Ala Val Gln Lys Ile Pro Val Ser Ser Leu
            195                 200                 205

Ser Gln Glu Ile Asp Tyr Thr Leu Glu Tyr Gly Trp His Thr Asn Met
        210                 215                 220

Pro Arg Leu Glu Thr Arg Asn Tyr Leu Asp Val Phe Gly His Pro Thr
225                 230                 235                 240

Ser Pro Trp Leu Lys Lys Lys Arg Thr Gln Tyr Leu Asp Ser Glu Lys
                245                 250                 255

Leu Leu Glu Leu Ala Lys Leu Glu Phe Asn Ile Phe His Ser Leu Gln

```
                    260                 265                 270
    Gln Lys Glu Leu Gln Tyr Leu Ser Arg Trp Trp Ile His Ser Gly Leu
                275                 280                 285

Pro Glu Leu Thr Phe Gly Arg His Arg His Val Glu Tyr Tyr Thr Leu
        290                 295                 300

Ser Ser Cys Ile Ala Thr Glu Pro Lys His Ser Ala Phe Arg Leu Gly
    305                 310                 315                 320

Phe Ala Lys Thr Cys His Leu Ile Thr Val Leu Asp Asp Ile Tyr Asp
                    325                 330                 335

Thr Phe Gly Thr Met Asp Glu Ile Glu Leu Phe Asn Glu Ala Val Arg
                340                 345                 350

Arg Trp Asn Pro Ser Glu Lys Glu Arg Leu Pro Glu Tyr Met Lys Glu
            355                 360                 365

Ile Tyr Met Ala Leu Tyr Glu Ala Leu Thr Asp Met Ala Arg Glu Ala
        370                 375                 380

Glu Lys Thr Gln Gly Arg Asp Thr Leu Asn Tyr Ala Arg Lys Ala Trp
    385                 390                 395                 400

Glu Val Tyr Leu Asp Ser Tyr Thr Gln Glu Ala Lys Trp Ile Ala Ser
                    405                 410                 415

Gly Tyr Leu Pro Thr Phe Glu Glu Tyr Leu Glu Asn Ala Lys Val Ser
                420                 425                 430

Ser Gly His Arg Ala Ala Ala Leu Thr Pro Leu Leu Thr Leu Asp Val
            435                 440                 445

Pro Leu Pro Asp Asp Val Leu Lys Gly Ile Asp Phe Pro Ser Arg Phe
        450                 455                 460

Asn Asp Leu Ala Ser Ser Phe Leu Arg Leu Arg Gly Asp Thr Arg Cys
    465                 470                 475                 480

Tyr Lys Ala Asp Arg Asp Arg Gly Glu Glu Ala Ser Ser Ile Ser Cys
                    485                 490                 495

Tyr Met Lys Asp Asn Pro Gly Leu Thr Glu Glu Asp Ala Leu Asn His
                500                 505                 510

Ile Asn Ala Met Ile Asn Asp Ile Ile Lys Glu Leu Asn Trp Glu Leu
            515                 520                 525

Leu Lys Pro Asp Ser Asn Ile Pro Met Thr Ala Arg Lys His Ala Tyr
        530                 535                 540

Glu Ile Thr Arg Ala Phe His Gln Leu Tyr Lys Tyr Arg Asp Gly Phe
    545                 550                 555                 560

Ser Val Ala Thr Gln Glu Thr Lys Ser Leu Val Arg Arg Thr Val Leu
                    565                 570                 575

Glu Pro Val Pro Leu
                580

<210> SEQ ID NO 10
<211> LENGTH: 572
<212> TYPE: PRT
<213> ORGANISM: Pinus banksiana

<400> SEQUENCE: 10

Val Ser Ser Thr Ala Ser Val Ser Asn Asp Asp Gly Val Arg Arg
    1               5                   10                  15

Val Gly Asp Tyr Arg Tyr Asn His Trp Asp Glu Asp Leu Ile Asp Ser
                    20                  25                  30

Leu Ala Thr Ser Tyr Glu Ala Pro Ser Tyr Leu Lys Arg Ala Asp Thr
                35                  40                  45
```

```
Leu Val Glu Ala Ile Lys Asp Arg Phe Asn Ser Met Gly Val Asp Asp
    50                  55                  60

Gly Glu Arg Met Ser Pro Leu Thr Asp Leu Tyr Gln Arg Leu Trp Met
65                  70                  75                  80

Val Asp Ser Val Glu Arg Leu Gly Ile Asp Arg His Phe Gln Asn Glu
                85                  90                  95

Ile Lys Ser Ala Leu Asp Tyr Val Phe Ser Tyr Trp Lys Glu Lys Gly
            100                 105                 110

Ile Gly Arg Gly Arg Gln Ser Ala Val Thr Asp Leu Asn Ser Thr Ala
            115                 120                 125

Leu Gly Leu Arg Thr Leu Arg Leu His Gly Tyr Pro Val Ser Ser Asp
130                 135                 140

Val Leu Glu Asn Phe Lys Asp His Asn Gly Gln Phe Thr Cys Ser Gly
145                 150                 155                 160

Ile Gln Thr Glu Gly Glu Ile Arg Gly Val Leu Asn Leu Phe Arg Ala
                165                 170                 175

Ser Leu Ile Ala Phe Pro Gly Glu Lys Val Met Glu Glu Ala Glu Ile
            180                 185                 190

Phe Ser Thr Met Tyr Leu Lys His Ala Leu Gln Lys Ile Ala Val Ser
            195                 200                 205

Ser Leu Ser Gln Glu Ile Glu Tyr Leu Leu Glu Tyr Gly Trp His Thr
210                 215                 220

Asn Pro Pro Arg Leu Glu Ala Arg Met Tyr Met Glu Val Phe Pro Gln
225                 230                 235                 240

Asp Thr Ile Tyr Glu Gln Lys Leu Val Glu Leu Ala Lys Val Glu Phe
                245                 250                 255

Asn Ile Phe His Ser Leu Gln Lys Arg Glu Leu Gln Ser Leu Thr Arg
            260                 265                 270

Trp Trp Lys His Tyr Gly Phe Pro Gln Leu Ser Phe Thr Arg His Ile
            275                 280                 285

His Val Glu Tyr Tyr Thr Phe Gly Ser Cys Ile Ala Thr Asp Pro Lys
            290                 295                 300

Gln Ser Ala Phe Arg Leu Cys Phe Ala Lys Met Ser Tyr Phe Val Thr
305                 310                 315                 320

Val Leu Asp Asp Ile Tyr Asp Thr Tyr Gly Thr Met Glu Glu Leu Glu
                325                 330                 335

Leu Phe Thr Ala Ala Ile Lys Arg Trp Asp Pro Ser Val Val Asp Cys
            340                 345                 350

Leu Pro Glu Tyr Met Lys Gly Val Tyr Met Ala Val Tyr Asp Thr Val
            355                 360                 365

Asn Glu Met Ala Lys Glu Ala Glu Lys Val Gln Gly Arg Asp Thr Leu
370                 375                 380

Asn Tyr Val Arg Gln Ala Trp Glu Leu Tyr Ile Asp Ala Tyr Met Pro
385                 390                 395                 400

Glu Ala Lys Trp Ile Ser Ser Gly Tyr Leu Pro Thr Phe Gln Glu Tyr
                405                 410                 415

Leu Asp Asn Ser Lys Ile Ser Phe Gly Thr Arg Ile Thr Ile Leu Gln
            420                 425                 430

Pro Ile Leu Thr Leu Gly Glu Pro Leu Pro His Glu Ile Leu Gln Glu
            435                 440                 445

Ile Asp Phe Pro Ala Lys Phe Asn Asp Leu Ile Ser Val Ile Leu Arg
450                 455                 460

Leu Lys Gly Asp Thr Arg Cys Tyr Lys Ala Asp Arg Ala Arg Gly Glu
```

```
            465                 470                 475                 480
Glu Ala Ser Ser Val Ser Cys Tyr Met Lys Asp Asn Ala Gly Ile Thr
                    485                 490                 495
Glu Glu Asp Ala Ile His Cys Ile Asn Asp Met Val Asn Asn Leu Leu
                500                 505                 510
Lys Glu Leu Asn Trp Glu Leu Leu Lys Pro Asp Ser Asn Val Pro Ile
                515                 520                 525
Ser Cys Arg Lys Ala Ala Phe Asp Ile Cys Arg Ile Phe His His Gly
            530                 535                 540
Tyr Lys Tyr Arg Asp Gly Tyr Gly Asp Ala Thr Ile Glu Val Lys Asn
545                 550                 555                 560
Leu Val Lys Arg Thr Val Leu Glu Pro Val Pro Leu
                565                 570

<210> SEQ ID NO 11
<211> LENGTH: 742
<212> TYPE: PRT
<213> ORGANISM: Solanum lycopersicum

<400> SEQUENCE: 11

Cys Ser His Ser Thr Thr Ser Ser Met Asn Gly Phe Glu Asp Ala Arg
1               5                   10                  15
Asp Arg Ile Arg Glu Ser Phe Gly Lys Leu Glu Leu Ser Pro Ser Ser
                20                  25                  30
Tyr Asp Thr Ala Trp Val Ala Met Val Pro Ser Arg His Ser Leu Asn
            35                  40                  45
Glu Pro Cys Phe Pro Gln Cys Leu Asp Trp Ile Ile Glu Asn Gln Arg
        50                  55                  60
Glu Asp Gly Ser Trp Gly Leu Asn Pro Thr His Pro Leu Leu Leu Lys
65                  70                  75                  80
Asp Ser Leu Ser Ser Thr Leu Ala Cys Leu Leu Ala Leu Thr Lys Trp
                85                  90                  95
Arg Val Gly Asp Glu Gln Ile Lys Arg Gly Leu Gly Phe Ile Glu Thr
                100                 105                 110
Tyr Gly Trp Ala Val Asp Asn Lys Asp Gln Ile Ser Pro Leu Gly Phe
            115                 120                 125
Glu Val Ile Phe Ser Ser Met Ile Lys Ser Ala Glu Lys Leu Asp Leu
        130                 135                 140
Asn Leu Pro Leu Asn Leu His Leu Val Asn Leu Val Lys Cys Lys Arg
145                 150                 155                 160
Asp Ser Thr Ile Lys Arg Asn Val Glu Tyr Met Gly Glu Gly Val Gly
                165                 170                 175
Glu Leu Cys Asp Trp Lys Glu Met Ile Lys Leu His Gln Arg Gln Asn
                180                 185                 190
Gly Ser Leu Phe Asp Ser Pro Ala Thr Thr Ala Ala Ala Leu Ile Tyr
            195                 200                 205
His Gln His Asp Gln Lys Cys Tyr Gln Tyr Leu Asn Ser Ile Phe Gln
        210                 215                 220
Gln His Lys Asn Trp Val Pro Thr Met Tyr Pro Thr Lys Val His Ser
225                 230                 235                 240
Leu Leu Cys Leu Val Asp Thr Leu Gln Asn Leu Gly Val His Arg His
                245                 250                 255
Phe Lys Ser Glu Ile Lys Lys Ala Leu Asp Glu Ile Tyr Arg Leu Trp
                260                 265                 270
```

-continued

```
Gln Gln Lys Asn Glu Gln Ile Phe Ser Asn Val Thr His Cys Ala Met
            275                 280                 285
Ala Phe Arg Leu Leu Arg Met Ser Tyr Tyr Asp Val Ser Ser Asp Glu
290                 295                 300
Leu Ala Glu Phe Val Asp Glu His Phe Ala Thr Asn Gly Lys
305                 310                 315                 320
Tyr Lys Ser His Val Glu Ile Leu Glu Leu His Lys Ala Ser Gln Leu
                325                 330                 335
Ala Ile Asp His Glu Lys Asp Asp Ile Leu Asp Lys Ile Asn Asn Trp
                340                 345                 350
Thr Arg Ala Phe Met Glu Gln Lys Leu Leu Asn Asn Gly Phe Ile Asp
            355                 360                 365
Arg Met Ser Lys Lys Glu Val Glu Leu Ala Leu Arg Lys Phe Tyr Thr
        370                 375                 380
Thr Ser His Leu Ala Glu Asn Arg Arg Tyr Ile Lys Ser Tyr Glu Glu
385                 390                 395                 400
Asn Asn Phe Lys Ile Leu Lys Ala Ala Tyr Arg Ser Pro Asn Ile Asn
                405                 410                 415
Asn Lys Asp Leu Leu Ala Phe Ser Ile His Asp Phe Glu Leu Cys Gln
                420                 425                 430
Ala Gln His Arg Glu Glu Leu Gln Gln Leu Lys Arg Trp Phe Glu Asp
            435                 440                 445
Tyr Arg Leu Asp Gln Leu Gly Leu Ala Glu Arg Tyr Ile His Ala Ser
        450                 455                 460
Tyr Leu Phe Gly Val Thr Val Ile Pro Glu Pro Glu Leu Ser Asp Ala
465                 470                 475                 480
Arg Leu Met Tyr Ala Lys Tyr Val Met Leu Leu Thr Ile Val Asp Asp
                485                 490                 495
His Phe Glu Ser Phe Ala Ser Lys Asp Glu Cys Phe Asn Ile Ile Glu
                500                 505                 510
Leu Val Glu Arg Trp Asp Asp Tyr Ala Ser Val Gly Tyr Lys Ser Glu
            515                 520                 525
Lys Val Lys Val Phe Phe Ser Val Phe Tyr Lys Ser Ile Glu Glu Leu
        530                 535                 540
Ala Thr Ile Ala Glu Ile Lys Gln Gly Arg Ser Val Lys Asn His Leu
545                 550                 555                 560
Ile Asn Leu Trp Leu Glu Leu Met Lys Leu Met Leu Met Glu Arg Val
                565                 570                 575
Glu Trp Cys Ser Gly Lys Thr Ile Pro Ser Ile Glu Glu Tyr Leu Tyr
            580                 585                 590
Val Thr Ser Ile Thr Phe Cys Ala Lys Leu Ile Pro Leu Ser Thr Gln
        595                 600                 605
Tyr Phe Leu Gly Ile Lys Ile Ser Lys Asp Leu Leu Glu Ser Asp Glu
610                 615                 620
Ile Cys Gly Leu Trp Asn Cys Ser Gly Arg Val Met Arg Ile Leu Asn
625                 630                 635                 640
Asp Leu Gln Asp Ser Lys Arg Glu Gln Lys Glu Val Ser Ile Asn Leu
                645                 650                 655
Val Thr Leu Leu Met Lys Ser Met Ser Glu Glu Ala Ile Met Lys
                660                 665                 670
Ile Lys Glu Ile Leu Glu Met Asn Arg Arg Glu Leu Leu Lys Met Val
            675                 680                 685
Leu Val Gln Lys Lys Gly Ser Gln Leu Pro Gln Leu Cys Lys Asp Ile
```

```
                    690             695             700
            Phe Trp Arg Thr Ser Lys Trp Ala His Phe Thr Tyr Ser Gln Thr Asp
            705                 710                 715                 720

Gly Tyr Arg Ile Ala Glu Glu Met Lys Asn His Ile Asp Glu Val Phe
                                725                 730                 735

Tyr Lys Pro Leu Asn His
                        740

<210> SEQ ID NO 12
<211> LENGTH: 23
<212> TYPE: PRT
<213> ORGANISM: Lavandula angustifolia

<400> SEQUENCE: 12

Pro Thr Gly Arg Arg Ser Gly Gly Tyr Pro Pro Ala Leu Trp Asp Phe
1               5                   10                  15

Asp Thr Ile Gln Ser Leu Asn
            20

<210> SEQ ID NO 13
<211> LENGTH: 24
<212> TYPE: PRT
<213> ORGANISM: Picea sitchensis

<400> SEQUENCE: 13

Asp Gly Val Gln Arg Arg Thr Gly Gly Tyr His Ser Asn Leu Trp Asn
1               5                   10                  15

Asp Asp Ile Ile Gln Phe Leu Ser
            20

<210> SEQ ID NO 14
<211> LENGTH: 24
<212> TYPE: PRT
<213> ORGANISM: Abies grandis

<400> SEQUENCE: 14

Asp Gly Leu Gln Arg Arg Ile Gly Asp Tyr His Ser Asn Leu Trp Asp
1               5                   10                  15

Asp Asp Phe Ile Gln Ser Leu Ser
            20

<210> SEQ ID NO 15
<211> LENGTH: 24
<212> TYPE: PRT
<213> ORGANISM: Pinus banksiana

<400> SEQUENCE: 15

Asp Gly Val Arg Arg Arg Val Gly Asp Tyr Arg Tyr Asn His Trp Asp
1               5                   10                  15

Glu Asp Leu Ile Asp Ser Leu Ala
            20

<210> SEQ ID NO 16
<211> LENGTH: 50
<212> TYPE: PRT
<213> ORGANISM: Solanum lycopersicum

<400> SEQUENCE: 16

Glu Gln Ile Lys Arg Gly Leu Gly Phe Ile Glu Thr Tyr Gly Trp Ala
1               5                   10                  15

Val Asp Asn Lys Asp Gln Ile Ser Pro Leu Gly Phe Glu Val Ile Phe
```

Ser Ser Met Ile Lys Ser Ala Glu Lys Leu Asp Leu Asn Leu Pro Leu
         35                  40                  45

Asn Leu
    50

<210> SEQ ID NO 17
<211> LENGTH: 49
<212> TYPE: PRT
<213> ORGANISM: Lavandula angustifolia

<400> SEQUENCE: 17

Cys Leu Asp Asp Ile Tyr Asp Val Tyr Gly Thr Ile Glu Glu Leu Gln
1               5                   10                  15

Leu Phe Thr Ser Thr Ile Gln Arg Trp Asp Leu Glu Ser Met Lys Gln
            20                  25                  30

Leu Pro Thr Tyr Met Gln Val Ser Phe Leu Ala Leu His Asn Phe Val
        35                  40                  45

Thr

<210> SEQ ID NO 18
<211> LENGTH: 49
<212> TYPE: PRT
<213> ORGANISM: Picea sitchensis

<400> SEQUENCE: 18

Ile Leu Asp Asp Met Tyr Asp Val Phe Gly Thr Ile Asp Glu Leu Glu
1               5                   10                  15

Leu Phe Thr Ala Gln Ile Lys Arg Trp Asp Pro Ser Ala Thr Asp Cys
            20                  25                  30

Leu Pro Lys Tyr Met Lys Arg Met Tyr Met Ile Leu Tyr Asp Met Val
        35                  40                  45

Asn

<210> SEQ ID NO 19
<211> LENGTH: 49
<212> TYPE: PRT
<213> ORGANISM: Abies grandis

<400> SEQUENCE: 19

Val Leu Asp Asp Ile Tyr Asp Thr Phe Gly Thr Met Asp Glu Ile Glu
1               5                   10                  15

Leu Phe Asn Glu Ala Val Arg Arg Trp Asn Pro Ser Glu Lys Glu Arg
            20                  25                  30

Leu Pro Glu Tyr Met Lys Glu Ile Tyr Met Ala Leu Tyr Glu Ala Leu
        35                  40                  45

Thr

<210> SEQ ID NO 20
<211> LENGTH: 49
<212> TYPE: PRT
<213> ORGANISM: Pinus banksiana

<400> SEQUENCE: 20

Val Leu Asp Asp Ile Tyr Asp Thr Tyr Gly Thr Met Glu Glu Leu Glu
1               5                   10                  15

Leu Phe Thr Ala Ala Ile Lys Arg Trp Asp Pro Ser Val Val Asp Cys
            20                  25                  30

```
Leu Pro Glu Tyr Met Lys Gly Val Tyr Met Ala Val Tyr Asp Thr Val
        35                  40                  45
Asn

<210> SEQ ID NO 21
<211> LENGTH: 50
<212> TYPE: PRT
<213> ORGANISM: Solanum lycopersicum

<400> SEQUENCE: 21

Ile Val Asp Asp His Phe Glu Ser Phe Ala Ser Lys Asp Glu Cys Phe
1               5                   10                  15

Asn Ile Ile Glu Leu Val Glu Arg Trp Asp Asp Tyr Ala Ser Val Gly
            20                  25                  30

Tyr Lys Ser Glu Lys Val Lys Val Phe Phe Ser Val Phe Tyr Lys Ser
        35                  40                  45

Ile Glu
    50

<210> SEQ ID NO 22
<211> LENGTH: 46
<212> TYPE: PRT
<213> ORGANISM: Lavandula angustifolia

<400> SEQUENCE: 22

Glu Arg Met His Lys Tyr Arg Asp Met Asn Arg Val Ser Ser Asn Ile
1               5                   10                  15

Val Arg Leu Ala Asp Asp Met Gly Thr Ser Leu Ala Glu Val Glu Arg
            20                  25                  30

Gly Asp Val Pro Lys Ala Ile Gln Cys Tyr Met Asn Glu Thr
        35                  40                  45

<210> SEQ ID NO 23
<211> LENGTH: 47
<212> TYPE: PRT
<213> ORGANISM: Picea sitchensis

<400> SEQUENCE: 23

Lys Glu Val Asp Phe Pro Ser Lys Leu Asn Asp Leu Ala Ser Ala Ile
1               5                   10                  15

Leu Arg Leu Arg Gly Asp Thr Arg Cys Tyr Lys Ala Asp Arg Ala Arg
            20                  25                  30

Gly Glu Glu Ala Ser Cys Ile Ser Cys Tyr Met Lys Asp Asn Pro
        35                  40                  45

<210> SEQ ID NO 24
<211> LENGTH: 47
<212> TYPE: PRT
<213> ORGANISM: Abies grandis

<400> SEQUENCE: 24

Lys Gly Ile Asp Phe Pro Ser Arg Phe Asn Asp Leu Ala Ser Ser Phe
1               5                   10                  15

Leu Arg Leu Arg Gly Asp Thr Arg Cys Tyr Lys Ala Asp Arg Asp Arg
            20                  25                  30

Gly Glu Glu Ala Ser Ser Ile Ser Cys Tyr Met Lys Asp Asn Pro
        35                  40                  45

<210> SEQ ID NO 25
<211> LENGTH: 47
```

```
<212> TYPE: PRT
<213> ORGANISM: Pinus banksiana

<400> SEQUENCE: 25

Gln Glu Ile Asp Phe Pro Ala Lys Phe Asn Asp Leu Ile Ser Val Ile
1               5                   10                  15

Leu Arg Leu Lys Gly Asp Thr Arg Cys Tyr Lys Ala Asp Arg Ala Arg
            20                  25                  30

Gly Glu Glu Ala Ser Ser Val Ser Cys Tyr Met Lys Asp Asn Ala
        35                  40                  45

<210> SEQ ID NO 26
<211> LENGTH: 42
<212> TYPE: PRT
<213> ORGANISM: Solanum lycopersicum

<400> SEQUENCE: 26

Glu Ser Asp Glu Ile Cys Gly Leu Trp Asn Cys Ser Gly Arg Val Met
1               5                   10                  15

Arg Ile Leu Asn Asp Leu Gln Asp Ser Lys Arg Glu Gln Lys Glu Val
            20                  25                  30

Ser Ile Asn Leu Val Thr Leu Leu Met Lys
        35                  40

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(3)
<223> OTHER INFORMATION: Xaa = Ser, Thr, Ile, or Val
<220> FEATURE:
<221> NAME/KEY: VARIANT
<222> LOCATION: (5)..(5)
<223> OTHER INFORMATION: Xaa = Gly or Asp
<220> FEATURE:
<221> NAME/KEY: VARIANT
<222> LOCATION: (7)..(7)
<223> OTHER INFORMATION: Xaa = Pro, His, or Arg
<220> FEATURE:
<221> NAME/KEY: VARIANT
<222> LOCATION: (8)..(8)
<223> OTHER INFORMATION: Xaa = Pro, Ser, or Tyr
<220> FEATURE:
<221> NAME/KEY: VARIANT
<222> LOCATION: (9)..(9)
<223> OTHER INFORMATION: Xaa = Ala or Asn
<220> FEATURE:
<221> NAME/KEY: VARIANT
<222> LOCATION: (10)..(10)
<223> OTHER INFORMATION: Xaa = Leu or His

<400> SEQUENCE: 27

Arg Arg Xaa Gly Xaa Tyr Xaa Xaa Xaa Xaa Trp
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic Construct

<400> SEQUENCE: 28

Lys Arg Gly Leu Gly Phe Ile Glu Thr Tyr Gly Trp
```

```
1               5                  10
```

<210> SEQ ID NO 29
<211> LENGTH: 11
<212> TYPE: PRT
<213> ORGANISM: Artificial Sequence
<220> FEATURE:
<223> OTHER INFORMATION: Synthetic Construct

<400> SEQUENCE: 29

```
Arg Arg Ser Gly Gly Tyr Pro Pro Ala Leu Trp
1               5                   10
```

<210> SEQ ID NO 30
<211> LENGTH: 11
<212> TYPE: PRT
<213> ORGANISM: Artificial Sequence
<220> FEATURE:
<223> OTHER INFORMATION: Synthetic Construct

<400> SEQUENCE: 30

```
Arg Arg Thr Gly Gly Tyr His Ser Asn Leu Trp
1               5                   10
```

<210> SEQ ID NO 31
<211> LENGTH: 11
<212> TYPE: PRT
<213> ORGANISM: Artificial Sequence
<220> FEATURE:
<223> OTHER INFORMATION: Synthetic Construct

<400> SEQUENCE: 31

```
Arg Arg Ile Gly Asp Tyr His Ser Asn Leu Trp
1               5                   10
```

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

```
Arg Arg Val Gly Asp Tyr Arg Tyr Asn His Trp
1               5                   10
```

<210> SEQ ID NO 33
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(4)
<223> OTHER INFORMATION: Xaa = any amino acid

<400> SEQUENCE: 33

```
Asp Asp Xaa Xaa Asp
1               5
```

<210> SEQ ID NO 34
<211> LENGTH: 9
<212> TYPE: PRT
<213> ORGANISM: Artificial Sequence
<220> FEATURE:
<223> OTHER INFORMATION: Synthetic Construct
<220> FEATURE:

```
<221> NAME/KEY: VARIANT
<222> LOCATION: (1)..(1)
<223> OTHER INFORMATION: Xaa = Asn or Asp
<220> FEATURE:
<221> NAME/KEY: VARIANT
<222> LOCATION: (3)..(4)
<223> OTHER INFORMATION: any amino acid
<220> FEATURE:
<221> NAME/KEY: VARIANT
<222> LOCATION: (5)..(5)
<223> OTHER INFORMATION: Xaa = Ser or Thr
<220> FEATURE:
<221> NAME/KEY: VARIANT
<222> LOCATION: (6)..(8)
<223> OTHER INFORMATION: Xaa = any amino acid

<400> SEQUENCE: 34

Xaa Asp Xaa Xaa Xaa Xaa Xaa Xaa Glu
1               5

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (3)..(3)
<223> OTHER INFORMATION: Xaa = Ile or Met

<400> SEQUENCE: 35

Asp Asp Xaa Tyr Asp
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Asp Asp His Phe Glu
1               5

<210> SEQ ID NO 37
<211> LENGTH: 25
<212> TYPE: PRT
<213> ORGANISM: Artificial Sequence
<220> FEATURE:
<223> OTHER INFORMATION: Synthetic Construct

<400> SEQUENCE: 37

Asn Arg Val Ser Ser Asn Ile Val Arg Leu Ala Asp Asp Met Gly Thr
1               5                   10                  15

Ser Leu Ala Glu Val Glu Arg Gly Asp
            20                  25

<210> SEQ ID NO 38
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (4)..(4)
<223> OTHER INFORMATION: Xaa = Ala or Ile
<220> FEATURE:
```

```
<221> NAME/KEY: VARIANT
<222> LOCATION: (6)..(6)
<223> OTHER INFORMATION: Xaa = Ala, Ser, or Val
<220> FEATURE:
<221> NAME/KEY: VARIANT
<222> LOCATION: (7)..(7)
<223> OTHER INFORMATION: Xaa = Ile or Phe
<220> FEATURE:
<221> NAME/KEY: VARIANT
<222> LOCATION: (11)..(11)
<223> OTHER INFORMATION: Xaa = Arg or Lys
<220> FEATURE:
<221> NAME/KEY: VARIANT
<222> LOCATION: (22)..(22)
<223> OTHER INFORMATION: Xaa = Ala or Asp

<400> SEQUENCE: 38

Asn Asp Leu Xaa Ser Xaa Xaa Leu Arg Leu Xaa Gly Asp Thr Arg Cys
1               5                   10                  15

Tyr Lys Ala Asp Arg Xaa Arg Gly Glu
            20                  25

<210> SEQ ID NO 39
<211> LENGTH: 13
<212> TYPE: PRT
<213> ORGANISM: Artificial Sequence
<220> FEATURE:
<223> OTHER INFORMATION: Synthetic Construct

<400> SEQUENCE: 39

Arg Ile Leu Asn Asp Leu Gln Asp Ser Lys Arg Glu Gln
1               5                   10

<210> SEQ ID NO 40
<211> LENGTH: 25
<212> TYPE: PRT
<213> ORGANISM: Artificial Sequence
<220> FEATURE:
<223> OTHER INFORMATION: Synthetic Construct

<400> SEQUENCE: 40

Asn Asp Leu Ala Ser Ala Ile Leu Arg Leu Arg Gly Asp Thr Arg Cys
1               5                   10                  15

Tyr Lys Ala Asp Arg Ala Arg Gly Glu
            20                  25

<210> SEQ ID NO 41
<211> LENGTH: 25
<212> TYPE: PRT
<213> ORGANISM: Artificial Sequence
<220> FEATURE:
<223> OTHER INFORMATION: Synthetic Construct

<400> SEQUENCE: 41

Asn Asp Leu Ala Ser Ser Phe Leu Arg Leu Arg Gly Asp Thr Arg Cys
1               5                   10                  15

Tyr Lys Ala Asp Arg Asp Arg Gly Glu
            20                  25

<210> SEQ ID NO 42
<211> LENGTH: 25
<212> TYPE: PRT
<213> ORGANISM: Artificial Sequence
<220> FEATURE:
<223> OTHER INFORMATION: Synthetic Construct

<400> SEQUENCE: 42
```

Asn Asp Leu Ile Ser Val Ile Leu Arg Leu Lys Gly Asp Thr Arg Cys
1               5                   10                  15

Tyr Lys Ala Asp Arg Ala Arg Gly Glu
            20                  25

<210> SEQ ID NO 43
<211> LENGTH: 20
<212> TYPE: DNA
<213> ORGANISM: Artificial Sequence
<220> FEATURE:
<223> OTHER INFORMATION: Synthetic Construct

<400> SEQUENCE: 43
aatccaggca ctgtgggaag                                              20

<210> SEQ ID NO 44
<211> LENGTH: 19
<212> TYPE: DNA
<213> ORGANISM: Artificial Sequence
<220> FEATURE:
<223> OTHER INFORMATION: Synthetic Construct

<400> SEQUENCE: 44
cacgaccgat gcctttctc                                               19

<210> SEQ ID NO 45
<211> LENGTH: 21
<212> TYPE: DNA
<213> ORGANISM: Artificial Sequence
<220> FEATURE:
<223> OTHER INFORMATION: Synthetic Construct

<400> SEQUENCE: 45
tttcgagctt ctaatcgtgg c                                            21

<210> SEQ ID NO 46
<211> LENGTH: 20
<212> TYPE: DNA
<213> ORGANISM: Artificial Sequence
<220> FEATURE:
<223> OTHER INFORMATION: Synthetic Construct

<400> SEQUENCE: 46
attgcgagtt tccaaccgag                                              20

<210> SEQ ID NO 47
<211> LENGTH: 20
<212> TYPE: DNA
<213> ORGANISM: Artificial Sequence
<220> FEATURE:
<223> OTHER INFORMATION: Synthetic Construct

<400> SEQUENCE: 47
tcgctgggcc aaagataagg                                              20

<210> SEQ ID NO 48
<211> LENGTH: 21
<212> TYPE: PRT
<213> ORGANISM: Artificial Sequence
<220> FEATURE:
<223> OTHER INFORMATION: Synthetic Construct

<400> SEQUENCE: 48

Trp Asn Cys Ser Gly Arg Val Met Arg Ile Leu Asn Asp Leu Gln Asp
1               5                   10                  15

```
Ser Lys Arg Glu Gln
         20
```

PRODUCTION OF MONOTERPENE BLENDS BY UNICELLULAR PHOTOSYNTHETIC MICROORGANISMS

CROSS-REFERENCE TO RELATED APPLICATIONS

This application is a U.S. National Phase of International Application No. PCT/US2017/034754, filed May 26, 2017, which claims priority benefit of U.S. provisional application no. 62/342,737 filed May 27, 2016, which is herein incorporated by reference in its entirety.

REFERENCE TO A SEQUENCE LISTING SUBMITTED AS AN ASCII TEXT FILE

The Sequence Listing written in file Sequence_Listing_1113545.txt, created on Nov. 26, 2018, 52,592 bytes, machine format IBM-PC, MS-Windows operating system, is hereby incorporated by reference in its entirety.

BACKGROUND OF THE INVENTION

Cyanobacteria are suitable hosts for heterologous production of plant essential oils that have commercial value as synthetic chemistry feedstock, in the pharmaceutical and cosmetic industries, and in household cleaning applications. Essential oils, such as monoterpene hydrocarbons, are naturally produced as secondary metabolites by several terrestrial plant species. Development of heterologous microbial systems for essential oils production is a valuable alternative to meet increasing product demand as compared to extraction from the plant biomass.

Heterologous expression in cyanobacteria of the β-phellandrene synthase (PHLS) from *Lavandula angustifolia* (lavender) has been shown. Transformation of *Synechocystis* with this single gene was sufficient to endow *Synechocystis* with the ability to synthesize β-phellandrene (monoterpene hydrocarbon) (Bentley et al. 2013, Formighieri and Melis 2014a, Formighieri and Melis 2015).

Leaves of *L. angustifolia* contain essential oils, primarily phellandrenes, and a few minor products such as camphor and borneol, in the range of 0.7-2.9 mg g$^{-1}$ fresh weight (Demissie et al. 2011). The LaPHLS encoding sequence was identified by microarray analysis to be highly transcribed in young lavender leaves. By in vitro assay, LaPHLS was shown to use geranyl-diphosphate (GPP) as substrate and to produce β-phellandrene as the major product (>86%), followed by limonene, consistent with the promiscuous activity of monoterpene synthases to convert the substrate into multiple terpene hydrocarbon products (Demissie et al. 2011). In contrast to higher plants, cyanobacteria and other aquatic microorganisms typically do not have the ability to generate monoterpene hydrocarbons, or other plant essential oils, as they lack the terpene synthase genes required for their synthesis (Van Wagoner et al. 2007). Constitutive generation of β-phellandrene in *Synechocystis* was achieved by heterologous expression of the LaPHLS encoding sequence. In particular, earlier work identified the slow $k_{cat}$ of the enzyme to be the main factor limiting rate and yield of product generation, a limitation that was overcome by increasing the concentration of the terpene synthase in the cyanobacterial cell (Formighieri and Melis 2015). This was achieved upon expression of LaPHLS under the strong endogenous cpc operon promoter and as a fusion protein with the highly abundant in cyanobacteria phycocyanin β-subunit (Formighieri and Melis 2016). The resulting *Synechocystis* transformants produced β-phellandrene as the major terpene product (88%), followed by a small amount of β-myrcene, while no limonene was detected. This was a distinct and interesting feature of monoterpenes blend obtained by heterologous expression of LaPHLS in cyanobacteria (Formighieri and Melis 2014a, Formighieri and Melis 2015), and one that differed from the product profile obtained in vitro and from the lavender leaf essential oil extracts (Demissie et al. 2011).

β-Phellandrene is an important constituent of the essential oils in different plant species. The glandular trichomes found on the surface of leaves and stems of *Solanum lycopersicum* (tomato) were reported to contain β-phellandrene (1 mg g$^{-1}$ leaf dry weight), followed by limonene, α-phellandrene and δ-2-carene. A β-phellandrene synthase was shown to be highly expressed in tomato trichomes, and to specifically use neryl-diphosphate (NPP) as substrate instead of geranyl-diphosphate (GPP). A neryl-diphosphate synthase (NPPS) was also identified as the enzyme catalyzing the formation of NPP from the universal terpenoid precursors isopentenyl-diphosphate (IPP) and dimethylallyl-diphosphate (DMAPP) (Schilmiller et al. 2009). When assayed in vitro with NPP, the profile of monoterpenes produced by SlPHLS was nearly identical with the profile of monoterpenes found in tomato trichomes (Schilmiller et al. 2009).

β-Phellandrene was additionally identified to be a constituent of the terpenoid oleoresin, which is used as a chemical and physical barrier against insect and pathogen attack by conifer trees. Oleoresin is stored in resin ducts of conifer bark, wood and needles (Hall et al. 2013). β-Phellandrene was found to accumulate up to 12 mg g$^{-1}$ dry weight in leader stem and needles of three-year-old pine trees, whose oleoresin constituents also include different amounts of β-pinene, α-pinene and 3-carene, depending on the plant species (Hall et al. 2013). β-Phellandrene synthases were identified by transcriptome analysis both in lodgepole pine (*Pinus contorta*) and jack pine (*Pinus banksiana*). In particular, two *P. contorta* and one *P. banksiana* PHLS sequences were identified, that encode for proteins that have 95-99% of identity. When assayed in vitro, these enzymes converted GPP into β-phellandrene representing 82-88% of the terpene product, plus minor amounts of α-phellandrene (Hall et al. 2013).

Transcriptome mining was also used to isolate β-phellandrene synthase encoding sequences in *Picea sitchensis* (Sitka spruce). Four PHLS were identified that share 99% of aminoacid identity, suggesting a recent gene duplication event. When assayed in vitro, these enzymes converted GPP into β-phellandrene as major product (~60%), followed by β-pinene (~20%) and α-pinene (~12%) (Keeling et al. 2011).

Screening of cDNA libraries resulted in the isolation of a β-phellandrene synthase from *Abies grandis* (grand fir), which, in combination with other monoterpene synthases, contributes to the production of turpentine. In vitro, the enzyme yielded β-phellandrene as the major product (52%), followed by β-pinene (34%), α-pinene (8.5%) and limonene (6%) (Bohlmann et al. 1999). Despite a similar monoterpenes profile, the PHLS from grand fir is only 70% identical to the PHLS proteins of Sitka spruce, suggesting that the gene function evolved independently (Keeling et al. 2011).

BRIEF SUMMARY OF CERTAIN ASPECTS OF THE DISCLOSURE

This disclosure provides methods and compositions to heterologously express β-phellandrene synthase (PHLS)

enzymes from different plant sources in cyanobacteria, e.g., Synechocystis. In the present disclosure, the β-phellandrene synthase (PHLS) proteins from *Solanum lycopersicum. Pinus banksiana., Picea sitchensis* and *Abies grandis* were heterologously expressed and characterized in cyanobacteria. Differences in terms of activity and product specificity of the aforementioned enzymes was observed in cyanobacteria in vivo. Employment of different PHLS enzymes in cyanobacteria is a strategy to obtain distinct monoterpene blends of commercial interest that were unexpectedly different from the corresponding plant essential oil extracts.

Illustrative data provided in the EXAMPLES section demonstrate that the β-phellandrene synthase from *Lavandula angustifolia* (lavender), *Solanum lycopersicum* (tomato). *Pinus banksiana* (pine), *Picea sitchensis* (Sitka spruce) and *Abies grandis* (grand fir) were active in cyanobacteria, e.g., *Synechocystis*, transformants and generated an unexpected blend of monoterpene hydrocarbons comprising β-phellandrene, α-phellandrene. β-myrcene, β-pinene, and δ-2-carene with variable percentage ratios ranging from <10% to >90% with different product combinations and proportions. These hydrophobic monoterpenes spontaneously diffused out of the cyanobacterial cells that generated them and accumulated as floater molecules on the surface of the liquid culture, a property that simplified harvesting. In some embodiments, a blend of monoterpene hydrocarbons produced in accordance with the disclosure may also comprise one or more of α-pinene, terpinene, ocimene or limonene.

In some embodiments, the disclosure provides a method of obtaining a blend of monoterpene hydrocarbons from cyanobacteria, the method comprising: culturing a cyanobacteria strain that has been genetically modified to express a heterologous β-phellandrene synthase under conditions in which the β-phellandrene synthase is expressed, wherein the heterologous β-phellandrene synthase is encoded by a polynucleotide comprising a β-phellandrene synthase nucleic acid sequence that is codon-optimized for expression in cyanobacteria fused to the 3' end of a leader nucleic acid sequence encoding a cyanobacteria protein that is expressed in cyanobacteria at a level of at least 1% of the total cellular protein; and isolating a blend of monoterpene hydrocarbons comprising at least two monoterpenes selected from the group consisting of β-phellandrene, α-phellandrene, β-myrcene, β-pinene, and δ-2-carene produced in the cyanobacteria that has spontaneously diffused from the cyanobacteria intracellular space into the culture medium. In some embodiments, the monoterpene blend comprises at least three monoterpenes selected from the group consisting of β-phellandrene, α-phellandrene, β-myrcene, β-pinene, and δ-2-carene. In some embodiments, the cyanobacteria protein expressed at a level of at least 1% of the total cellular protein is a β-subunit of phycocyanin (cpcB), an α-subunit of phycocyanin (cpcA), a phycoerythrin subunit (cpeA or cpcB), an allophycocyanin subunit (apcA or apcB), a large subunit of Rubisco (rbcL), a small subunit of Rubisco (rbcS), a D1/32 kD reaction center protein (psbA) of photosystem-II, a D2/34 kD reaction center protein (psbD) of photosystem-II, a CP47 (psbB) or CP43 (psbC) reaction center protein of photosystem-II, a psaA or psaB reaction center protein of photosystem-I, a psaC or psaD reaction center protein of photosystem-I, an rpl ribosomal RNA protein, or an rps ribosomal RNA protein. In some embodiments, the cyanobacteria protein is the β-subunit of phycocyanin (cpcB) or the α-subunit of phycocyanin (cpcA). In some embodiments, the β-phellandrene synthase is lavender, tomato, grand fir, pine, or spruce β-phellandrene synthase. In some embodiments, the β-phellandrene synthase has at least 70% identity to a β-phellandrene synthase sequence set forth in FIG. 9 and comprises conserved domains having a sequence of an underlined region of a β-phellandrene polypeptide sequence as shown in FIG. 9*a*-9*d*. In some embodiments, the β-phellandrene has at least 80% identity, and in some embodiments at least 90% identity, to a β-phellandrene synthase sequence set forth in FIG. 9*a*-9*d* and comprises conserved domains as described herein. In some embodiments, the monoterpene hydrocarbon blend produced by the expression of the heterologous β-phellandrene comprises β-phellandrene in an amount of at least 10% of the total monoterpene hydrocarbon blend. In some embodiments, the cyanobacteria strain is from a genus selected from the group consisting of *Synechocystis, Synechococcus, Athrospira, Nostoc,* and *Anabaena*.

In some aspects, the disclosure provides a culture comprising a cyanobacteria strain that has been genetically modified to express a heterologous β-phellandrene synthase under conditions in which the β-phellandrene synthase is expressed, wherein the heterologous β-phellandrene synthase is encoded by a polynucleotide comprising a β-phellandrene synthase nucleic acid sequence that is codon-optimized for expression in cyanobacteria fused to the 3' end of a leader nucleic acid sequence encoding a cyanobacteria protein that is expressed in cyanobacteria at a level of at least 1% of the total cellular protein; and wherein the culture comprises a blend of monoterpene hydrocarbons comprising at least two monoterpenes selected from the group consisting of β-phellandrene, α-phellandrene, β-myrcene, β-pinene, and δ-2-carene produced in the cyanobacteria that has spontaneously diffused from the cyanobacteria intracellular space into the culture medium.

In some embodiments, the β-phellandrene synthase expressed in accordance with the disclosure is a tomato β-phellandrene synthase and the method comprises co-expressing the tomato β-phellandrene synthase with a neryl-diphosphate synthase (NPPS), such as a tomato NPSS. In some embodiments, the blend of monoterpene hydrocarbon produces by co-expressing the tomato β-phellandrene synthase with a NPPS such as tomato NPSS in cyanobacteria comprises β-phellandrene, α-phellandrene, β-myrcene, β-pinene and δ-carene.

In some embodiments, the β-phellandrene synthase expressed in cyanobacteria in accordance with the disclosure is from *Pinus banksiana* and the blend of monoterpenes comprises β-phellandrene, β-myrcene, and β-pinene.

In some embodiments, the β-phellandrene synthase expressed in cyanobacteria in accordance with the disclosure is from *Picea sitchensis* and the blend of monoterpenes comprises β-phellandrene, α-phellandrene, β-myrcene, and β-pinene.

In some embodiments, the β-phellandrene synthase expressed in cyanobacteria in accordance with the disclosure is from *Abies grandis* and the blend of monoterpenes comprises β-phellandrene, β-myrcene, and β-pinene.

In some embodiments, a β-phellandrene synthase that is expressed to obtain a monoterpene blend is expressed in a unicellular photosynthetic microorganism selected from the group consisting of green algae, diatoms, red algae, and brown algae. A β-phellandrene synthase nucleic acid for expression in the unicellular photosynthetic microorganism encodes a β-phellandrene synthase as described herein. Examples of green algae include *Chlamydomonas reinhardtii; Dunaliella salina; Chlorella fusca; Chlorella vulgaris; Scenedesmus obliquus; Botryococcus braunii*. Examples of diatoms that can be modified to express a β-phellandrene synthase in accordance with this disclosure to produce a blend of monoterpenes include *Pheodactylum tricornutum: Cylindrotheca fusiformis; Cyclotella gamma; Nannochloropsis oceanica*; and *Thalassiosira pseudonana*. Examples of red algae that can be modified to express a β-phellandrene synthase in accordance with this disclosure to produce a blend of monoterpenes include *Porphyridium cruentum; Cyanidioschywon merolae: Flintiella sanguinaria*; and *Rhodosorus marinus*.

BRIEF DESCRIPTION OF THE FIGURES

FIG. 5a-5d provides data illustrating expression of *Picea sitchensis* (Sipka spruce) β-phellandrene synthase (PsPHLS) in *Synechocystis*. 5a: PsPHLS was expressed as a fusion to CpcB in the cpc genomic locus. 5b: Genomic PCR analysis with cpc_us and cpcA_Rv primers. 5c: Genomic PCR analysis with cpc_us and PsPHLS_Rv primers. Location of the primers is shown as arrows in (a). Ps denotes three independent transformants lines. 5d: SDS-PAGE resolution and Coomassie-stain of total cell protein extracts from *Synechocystis* wild type and transformants. The CpcB.PsPHLS fusion protein and the native CpcB are marked at 84 kD and 18 kD, respectively. Molecular weight markers are on the left side and expressed in kD.

FIG. 9a-9d shows an amino acid sequence alignment of representative PHLS proteins from the N-terminus (9a) to the C-terminus (9d) (*L. angustifolia* (SEQ ID NO: 7); *P. sitchensis* (SEQ ID NO: 8); *A. grandis* (SEQ ID NO: 9); *P. banksiana* (SEQ ID NO: 10); *S. lycopersicum* (SEQ ID NO: 11)). The putative transit sequences are removed from the protein sequences SEQ ID NOS:7-11 in the alignment. Conserved motifs involved in class I activity are underlined: the RR(x8)W sequence, or KR(x9) W in SIPHLS; the DD-rich motif and the partially conserved (N/D)Dxx(S/T) xxxE sequence (SEQ ID NO:34), which coordinate three divalent metal (Mg2+ or Mn2+) ions required for catalysis (Demissie et al. 2011, Zhou et al. 2012).

FIG. 11a-11d shows modeling of protein folding by the RaptorX web server (Källberg et al 2012) of *Lavandula angustifolia* PHLS and *Solanum lycopersicum* PHLS protein structures. 11a: Predicted structure of the LaPHLS protein, showing the αβ domains and the N-terminal strand folding back across the C-terminal α-domain. Best template: limonene synthase (2ongA), p-value 2.43e-14. 11b: CpcB·LaPHLS fusion protein structure, where the CpcB moiety is predicted to be structurally independent and not interfering with LaPHLS activity. 11c: Predicted structure of the SIPHLS protein, showing the αβγ domains. Best template: abietadiene synthase (3s9vA), p-value 9.58e-18. 11d: CpcB·SIPHLS fusion protein structure, where the CpcB moiety is predicted to be structurally at right angles and, hence, not interfering with reactant access to SIPHLS.

DETAILED DESCRIPTION OF THE INVENTION

Terminology

Figures 1A, 1B, 1C, 1D, 1E, 1F:
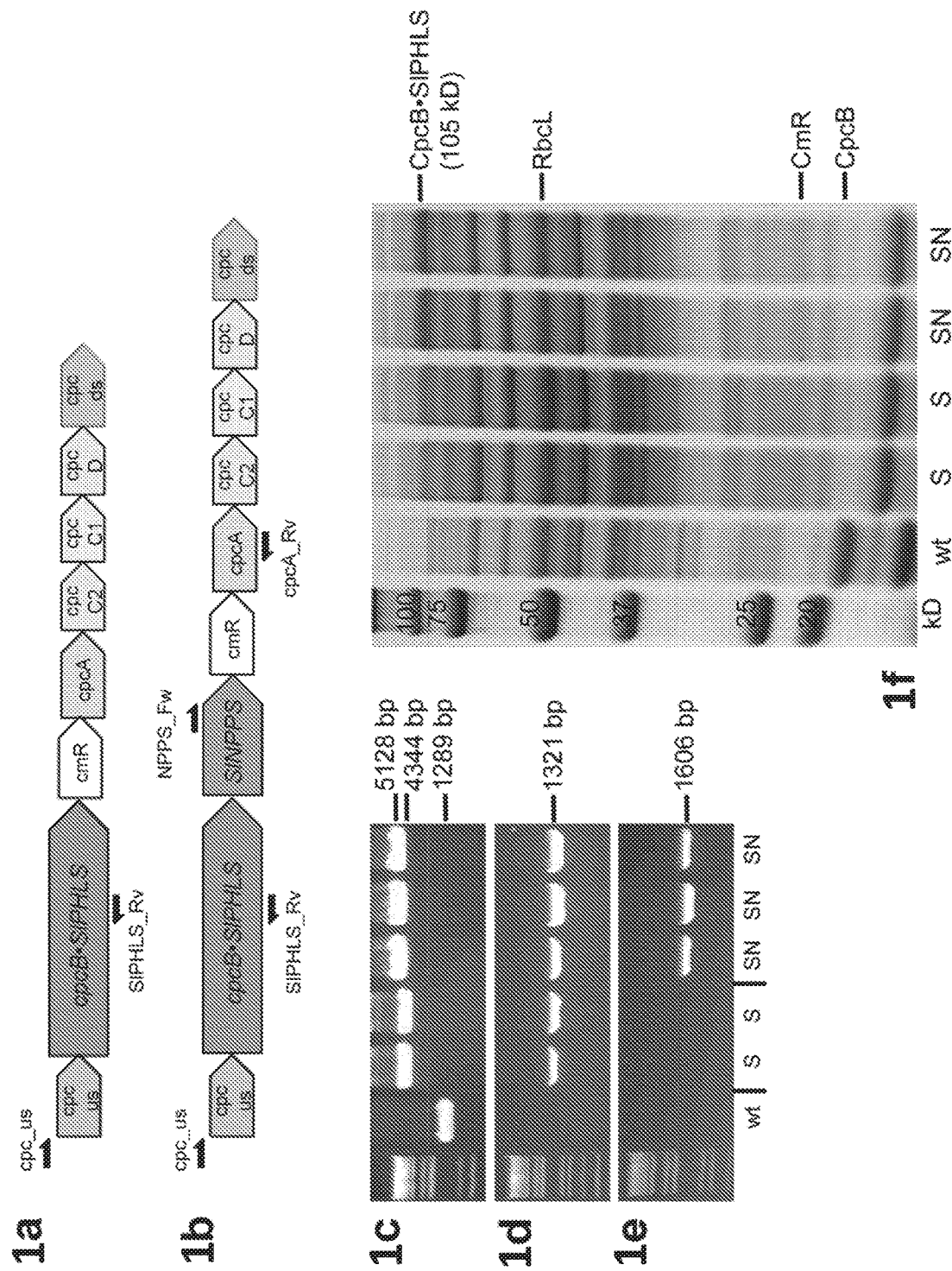
FIG. 1a-1f provides data illustrating expression of *Solanum lycopersicum* (tomato) β-phellandrene synthase (SIPHLS) and neryl diphosphate synthase (SINPPS) in *Synechocystris*. 1a: Recombinant construct for expression of SIPHLS as a fusion to the phycocyanin β-subunit (CpcB) in the cpc genomic locus. 1b: Recombinant construct for co-expression of the CpcB·SIPHLS fusion construct with the NPPS. 1c: Genomic PCR analysis of wild type and transformant *Synechocystis* with cpc_us and cpcA_Rv primers. 1d: Genomic PCR analysis with cpc_us and SIPHLS_Rv primers. 1e: Genomic PCR analysis with NPPS_Fw and cpcA_Rv primers. Location of the primers is shown as arrows in panels (a) and (b). S denotes two independent CpcB·SIPHLS transformant lines, while SN denotes three independent CpcB·SIPHLS+NPPS transformant lines. 1f: SDS-PAGE resolution and Coomassie-stain of total cell protein extracts from *Synechocystis* wild type and transformants. The CpcB·SIPHLS fusion protein and the native CpcB are marked as 105 kD and 18 kD polypeptides, respectively. Molecular weight markers are shown on the left-most lane and expressed in kD.

The term "naturally-occurring" or "native" as used herein as applied to a nucleic acid, a protein, a cell, or an organism, refers to a nucleic acid, protein, cell, or organism that is found in nature. For example, a polypeptide or polynucleotide sequence that is present in an organism that can be isolated from a source in nature and which has not been intentionally modified by a human in the laboratory is naturally occurring.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence endogenous to the host microorganism or host cell. In some embodiments, a "heterologous" nucleic acid may comprise a nucleotide sequence that differs in sequence from the endogenous nucleotide sequence but encodes the same protein (having the same amino acid sequence) as found endogenously; or two or more nucleotide sequences that are not found in the same relationship to each other in nature, e.g., the nucleic acid is recombinant. An example of a heterologous nucleic acid is a nucleotide sequence encoding a fusion protein comprising two proteins that are not joined to one another in nature.

The term "recombinant" polynucleotide or nucleic acid refers to one that is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. A "recombinant" protein is encoded by a recombinant polynucleotide. In the context of a genetically modified host cell, a "recombinant" host cell refers to both the original cell and its progeny.

As used herein, the term "genetically modified" refers to any change in the endogenous genome of a cyanobacteria cell compared to a wild-type cell. Thus, changes that are introduced through recombinant DNA technology and/or classical mutagenesis techniques are both encompassed by this term. The changes may involve protein coding sequences or non-protein coding sequences such as regulatory sequences as promoters or enhancers.

An "expression construct" or "expression cassette" as used herein refers to a recombinant nucleic acid construct, which, when introduced into a cyanobacterial host cell in accordance with the present invention, results in increased expression of a fusion protein encoded by the nucleic acid construct. The expression construct may comprise a promoter sequence operably linked to a nucleic acid sequence encoding the fusion protein or the expression cassette may comprise the nucleic acid sequence encoding the fusion protein where the construct is configured to be inserted into a location in a cyanobacterial genome such that a promoter endogenous to the cyanobacterial host cell is employed to drive expression of the fusion protein.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the term "exogenous protein" refers to a protein that is not normally or naturally found in and/or produced by a given cyanobacterium, organism, or cell in nature. As used herein, the term "endogenous protein" refers to a protein that is normally found in and/or produced by a given cyanobacterium, organism, or cell in nature.

An "endogenous" protein or "endogenous" nucleic acid" is also referred to as a "native" protein or nucleic acid that is found in a cell or organism in nature.

The terms "nucleic acid" and "polynucleotide" are used synonymously and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones. Thus, nucleic acids or polynucleotides may also include modified nucleotides, that permit correct read through by a polymerase. "Polynucleotide sequence" or "nucleic acid sequence" may include both the sense and antisense strands of a nucleic acid as either individual single strands or in a duplex. As will be appreciated by those in the art, the depiction of a single strand also defines the sequence of the complementary strand, thus the sequences described herein also provide the complement of the sequence. Unless otherwise indicated, a particular nucleic acid sequence also implicitly encompasses conservatively modified variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc The term "promoter" or "regulatory element" refers to a region or sequence determinants located upstream or downstream from the start of transcription that are involved in recognition and binding of RNA polymerase and other proteins to initiate transcription. A "cyanobacteria promoter" is a promoter capable of initiating transcription in cyanobacteria cells. Such promoters need not be of cyanobacterial origin, for example, promoters derived from other bacteria or plant viruses, can be used in the present invention.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman Add. *APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (U.S.A.) 85: 2444 (1988), by computerized implementations of these algorithms (GAP, BESTFIT. BLAST. FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" in the context of polynucleotide or polypeptide sequences means that a polynucleotide or polypeptide comprises a sequence that has at least 50% sequence identity to a reference nucleic acid or polypeptide sequence. Alternatively, percent identity can be any integer from 40% to 100%. Exemplary embodiments include at least: 50%, 55%, 60%, 65%, 70%, 75%, 80%, 85%, 90%, 95%, or 99% compared to a reference sequence using the programs described herein; preferably BLAST using standard parameters, as described below.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

The term "isolated", when applied to a nucleic acid or protein, denotes that the nucleic acid or protein is essentially free of other cellular components with which it is associated in the natural state. It is preferably in a homogeneous state and may be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. In particular, an isolated gene is separated from open reading frames which flank the gene and encode a protein other than the gene of interest.

As used herein, "mass-culturing" refers to growing large quantities of cyanobacteria, that have been modified to express a β-phellandrene synthase gene. A "large quantity" is generally in the range of about 100 liters to about 1,500,000 liters, or more. In some embodiments, the organisms are cultured in large quantities in modular bioreactors, each having a capacity of about 1,000 to about 1,000,000 liters.

A "bioreactor" in the context of this invention is any enclosed large-capacity vessel in which cyanobacteria are grown. A "large-capacity vessel" in the context of this invention can hold about 100 liters, often about 500 liters, or about 1,000 liters to about 1,000,000 liters, or more.

As used herein, "harvesting" or "isolating" terpenes produced by β-phellandrene synthase refers to collecting the terpenes that have spontaneously diffused from within the intracellular space into the liquid culture medium and floated on the surface of the liquid culture medium.

DETAILED DESCRIPTION OF THE INVENTION

The invention employs various routine recombinant nucleic acid techniques. Generally, the nomenclature and the laboratory procedures in recombinant DNA technology described below are those commonly employed in the art. Many manuals that provide direction for performing recombinant DNA manipulations are available, e.g., Molecular Cloning, A Laboratory Manual. (Sambrook, J. and Russell, D., eds.). CSHL Press. New York (3rd Ed, 2001): and Current Protocols in Molecular Biology. (Ausubel et al., eds.), New Jersey (1994-1999).

In one aspect, the invention is based, in part, on the discovery that expression of plant β-phellandrene synthase in cyanobacteria results in the production of blends of terpenes that are not the same as those in extracts from plants.

β-Phellandrene Synthase Nucleic Acid and Polypeptide Sequences

β-phellandrene synthase nucleic acid and polypeptide sequences are known in the art. β-phellandrene synthase genes have been isolated, sequenced and characterized from lavender (*Lavandular angustifolia*), grand fir (*Abies grandis*), tomato (*Solanum lycopersicum*) and spruce (*Picea abies. Picea sitchensis*). See, e.g., Demissie et al., Planta, 233:685-6% (2011); Bohlmann et al., Arch. Biochem. Biophys., 368:232-243 (1994); Schilmiller et al., Proc. Nat. Acad. Sci. U.S.A., 106:10865-10870 (2009): and Keeling et al., BMC Plant Biol. 11:43-57 (2011). Illustrative accession numbers are: lavender (*Lavandula angustifolia* cultivar Lady), Accession: HQ404305; tomato (*Solanum lycopersicum*), Accession: FJ797957; grand fir (*Abies grandis*), Accession: AF139205; spruce (*Picea sitchensis*) (4 genes identified, Accession Nos: Q426162 (PsTPS-Phel-1), HQ426169 (PsTPS-Phel-2), HQ426163 (PsTPS-Phel-3), HQ426159 (PsTPS-Phel-4). FIG. 9 illustrates an amino acid alignment of β-phellandrene synthases from lavender, grand fir, tomato and spruce.

The alignments in FIG. 9a-9d show that there is a greater divergence in the N-terminal part of the enzymes, as compared to the C-terminal region of the proteins. Overall, the degree of identity among the sequences shown in FIG. 9a-9d is 70% between *Picea sitchensis* and *Abies grandis* PHLS, followed by 63% with the *Pinus banksiana* counterpart. These conifer enzymes differ from the *Lavandula angustifolia* PHLS, showing only ~20% of identity with the latter. The *Solanum lycopersicum* PHLS is also differs from the other PHLS enzymes shown in FIG. 9a-9d, having only ~15% identity with the rest.

Figure 10:
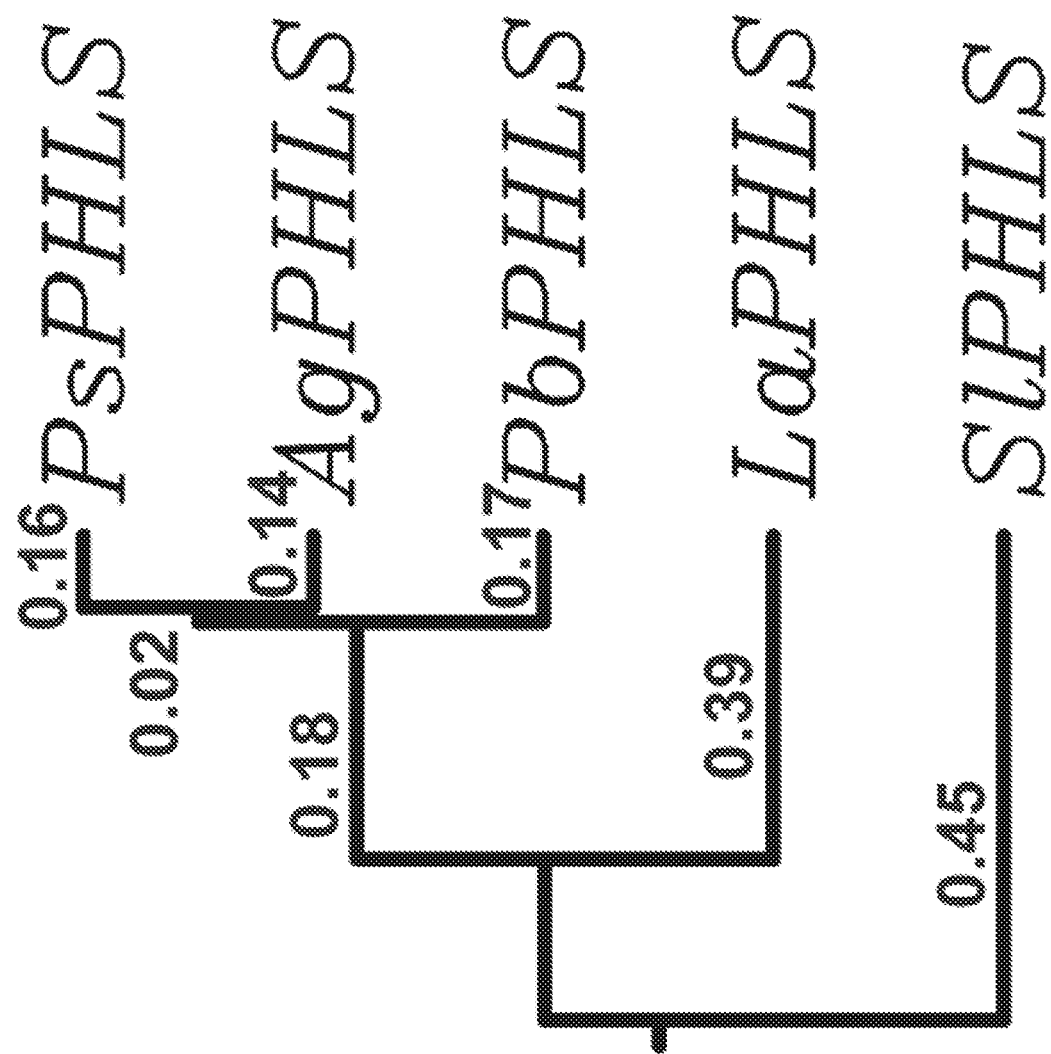
FIG. 10 shows a rooted phylogenetic tree (UPGMA) based on the ClustalW aminoacid sequence alignment of the PHLS proteins heterologously expressed in *Synechocystis*. Branch lengths are proportional to the nucleotide substitutions per site.

A rooted phylogenetic tree, based on the ClustalW amino acid sequence alignment in FIG. 9a-9d is shown in FIG. 10.

It shows closer proximity, i.e. fewer nucleotide substitutions per site, among the conifer monoterpene synthases, and a higher degree of sequence divergence between the conifer monoterpene synthases and either the *Lavandula angustifolia* PHLS or the *Solanum lycopersicum* PHLS, consistent with their taxonomic classification.

Although the amino acid sequences differ in terms of their percent identity to one another, there are important motifs that are conserved among terpene synthases that are identified as playing a role in catalysis.

In particular, the arginine-rich RR(x8)W signature motif is localized near the N-terminus, but it is part of an N-terminal strand that folds back on the C-terminal domain and supports closure of the active site (Hyatt et al. 2007, Srividya et al. 2015). This motif is conserved in *Solanum lycopersicum* PHLS as a KR(x9)W sequence. The sequences corresponding to this motif are underlined in the following:

```
L.angustifoliaADQ73631.1      P-TGRRSGGYPPALWDFDTIQSLN------------------------        32
(SEQ ID NO: 12)

P.sitchensisADZ45506.1        DGVQRRTGGYHSLNWNDDIIQFLS------------------------        33
(SEQ ID NO: 13)

A.grandisAAF61453.1           DGLQRRIGDYHSNLWDDDPIQSLS------------------------        33
(SEQ ID NO: 14)

P.banksianasAFU73854.1        DGVRRRVGDYRYNHWDEDLIDSLA------------------------        34
(SEQ ID NO: 15)

S.lycopersicumACO56896.1      EQIKRGLGFIETYGWAVDNKDQISPLGFEVIFSSMIKSAEKLDLNLPLNL     150
(SEQ ID NO: 16)
```

The C-terminal α-domain contains the class I (ionization-initiated) active site, characterized by the aspartate-rich DDxxD (SEQ ID NO:33) motif (corresponding sequences are underlined in the upper alignment) and the partially conserved (N/D)Dxx(S/T)xxxE (SEQ ID NO:34) sequence that coordinate the binding of three divalent metal ($Mg^{2+}$ or $Mn^{2+}$) ions (corresponding sequence are underlined in the lower alignment). The latter are required for substrate binding and activation (Demissie et al. 2011, Hyatt et al. 2007, Zhou et al. 2012).

```
L.angustifoliaADQ73631.1      CLDDTYDVYGTIEELQLFTSTIQRWDLKS-MKQLPTYMQVSFLALHNPVT      339
(SEQ ID NO: 17)

P.sitchensisADZ45506.1        ILDDMYDVFGTIDELELFTAQIKRWDPSA-TDCLPKYMKRMYMILYDMVN      373
(SEQ ID NO: 18)

A.grandisAAF61453.1           VLDDIYDTFGTMDEIELFNEAVRRWNPSE-KERLPEYMKEIYMALYEALT      379
(SEQ ID NO: 19)

P.banksianaAFU73854.1         VLDDIYDTYGTMEELELFTAAIKRWDPSV-VDCLPEYMKGVYMAVYDTVN      369
(SEQ ID NO: 20)

S.lycopersicumACO56896.1      IVDDHFESFASKDECFNIIELVERWDDYASVGYKSEKVKVFFSVFYKSIE      542
(SEQ ID NO: 21)

L.angustifoliaADQ73631.1      ERMHKYRDMNRVSSNIVRLADDMGTSLAEVERGDVPKAIQCYMNET-          455
(SEQ ID NO: 22)

P.sitchensisADZ45506.1        KEVDFPSKLNDLASAILRLRGDTRCYKADRARGEEASCISCYMKDNP          497
(SEQ ID NO: 23)

A.grandisAAF61453.1           KGIDFPSRFNDLASSFLRLRGDTRCYKADRDRGEEASSISCYMKDNP          503
(SEQ ID NO: 24)
```

-continued

| P.banksianaAFU73854.1 (SEQ ID NO: 25) | QEIDFPAKF<u>NDLISVILRLKGDTRCYKADRARGE</u>EASSVSCYMKDNA | 493 |
| --- | --- | --- |
| S.lycopersicumACO56896.1 (SEQ ID NO: 26) | ESDEICG-LWNCSGRVM<u>RILNDLQDSK</u>----<u>REQ</u>KEVSINLVTLLMK | 662 |

Modeling of the 3D structures of the PHLS proteins (FIG. 11a-11d) performed with the RaptorX web server (Källberg et al 2012), showed differences in the folding of the respective polypeptides. The PHLS from *Lavandula angustifolia* (Bentley et al. 2013; Formighieri and Melis 2014a. Formighieri and Melis 2015) was predicted to have a two-domain (αβ) structure, and is similar to the limonene synthase from *Mentha spicata* that served as the best template (2ongA, p-value 2.43e-14) (FIG. 11a). The N-terminal strand (FIG. 11a), that precedes the β-domain, was also retained, and it folds back across the C-terminal α-domain to form a 'cap' that shields reactive carbocation intermediates from the solvent (Hyatt et al. 2007, Srividya et al. 2015). Modeling of the CpcB·LaPHLS fusion protein showed the CpcB fusion moiety to be structurally independent from the LaPHLS (FIG. 11b).

As the case was for the LaPHLS, PHLS proteins from conifer trees (*Pinus banksiana. Picea sitchensis* and *Abies grandis*) were also modeled with a two-domain (αβ) structure (FIG. 11a).

Modeling of the 3D structure of the SIPHLS protein using the RaptorX web server (Källberg et al 2012) showed a three-domain (αβγ) structure (FIG. 11c) with the best template being that of the abietadiene (diterpene) synthase from *Abies grandis* (3s9vA, p-value 9.58e-18). Modeling of the CpcB·SIPHLS fusion protein showed the CpcB domain to be structurally independent from the SIPHLS moiety (FIG. 11d). In the case of the SIPHLS, the C-terminal α-domain contains the class I active site where the NPP substrate ionizes to a neryl-cation intermediate before being converted to the monoterpene product(s) (Schilmiller et al. 2009).

A β-phellandrene synthase expressed in accordance with the invention comprises sequences conserved in β-phellandrene synthase polypeptides. In some embodiments, such α-phellandrene synthase of the present disclosure comprises an arginine-rich region comprising RR(S/T/I/V)G(G/D)Y(P/H/R)(P/S/Y)(A/N)(L/H)W (SEQ ID NO:27). In some embodiments, e.g., when the β-phellandrene synthase is a tomato β-phellandrene synthase variant, the β-phellandrene synthase comprises KRGLGFIETYGW (SEQ ID NO:28). In some embodiments, the β-phellandrene synthase comprises RRSGGYPPALW (SEQ ID NO:29). In some embodiments, the β-phellandrene synthase comprises RRTGGYHSNLW (SEQ ID NO:30). In some embodiments, the β-phellandrene synthase comprises RRIGDYHSNLW (SEQ ID NO:31). In some embodiments, the β-phellandrene synthase comprises RRVGDYRYNHW (SEQ ID NO:32).

In some embodiments, the β-phellandrene synthase comprises a C-terminal α-domain active site characterized by an aspartate-rich DDxxD (SEQ ID NO:33) motif and a partially conserved sequence referred to as an (N/D)Dxx(S/T)xxxE sequence (SEQ ID NO:34) that coordinates binding of divalent metal ions (referred to herein for convenience as a "metal-binding sequence"). For example, in some embodiments, a β-phellandrene synthase of the present disclosure comprises a C-terminal α-domain active site sequence DD(I/M)YD (SEQ ID NO:35). In some embodiments, e.g., when the a β-phellandrene synthase is tomato a β-phellandrene synthase variant, the β-phellandrene synthase comprises a C-terminal α-domain active site sequence DDHFE (SEQ ID NO:36). In some embodiments, a β-phellandrene synthase of the present disclosure comprises a metal binding sequence NRVSSNIVRLADDMGTSLAEVERGD (SEQ ID NO:37). In some embodiments, a β-phellandrene synthase of the present disclosure comprises a metal binding sequence NDL(A/I)S(A/SN)(I/F)LRL(R/K)GDTRCYKADR(A/D)RGE (SEQ ID NO:38). In some embodiments, e.g., when the β-phellandrene synthase is a tomato β-phellandrene synthase variant, the β-phellandrene synthase a metal binding sequence RILNDLQDSKREQ (SEQ ID NO:39). In some embodiments, the β-phellandrene synthase comprises a metal binding sequence NDLASAILRLRGDTRCYKADRARGE (SEQ ID NO:40). In some embodiments, the β-phellandrene synthase comprises a metal binding sequence NDLASSFLRLRGDTRCYKADRDRGE (SEQ ID NO:41). In some embodiments, the β-phellandrene synthase comprises a metal binding sequence NDLISVILRLKGDTRCYKADRARGE (SEQ ID NO:42). In some embodiments, the β-phellandrene synthase comprises the amino acid sequence WNCSGRVMRILNDLQDSKREQ (SEQ ID NO: 48).

Preferably, a β-phellandrene synthase of the present disclosure comprises an arginine-rich region, a C-terminal α-domain active site sequence, and metal binding sequence as described in the two preceding paragraphs.

In the present disclosure, a nucleic acid construct that encodes a β-phellandrene synthase polypeptide is introduced into cyanobacteria for expression. The β-phellandrene synthase polypeptide encoded by the construct typically has at least 70%, at least 75%, at least 80%, at least 85%, at least 90%, or at least 95%, or greater, identity to a β-PHLS polypeptide set forth in FIG. 9a-9d in cyanobacteria and comprises conserved domains as underlined in FIG. 9a-9d. A β-PHLS polypeptide encoded by a nucleic acid employed in the methods of the invention have the catalytic activity of converting GPP or its cis-isomer to β-phellandrene. In some embodiments, the invention provides a β-PHLS gene that encodes a modified version of a β-PHLS polypeptide from an angiosperm or gymnosperm plant, such as lavender, grand fir, tomato, pine, or spruce. A β-PHLS polypeptide variant suitable for use in the present invention possesses the ability to convert GPP or NPP to β-phellandrene when heterologously expressed in cyanobacteria. In some embodiments, the β-PHLS polypeptide variant employs GPP. In some embodiments, a β-PHLS for use in the invention has at least 70%, typically at least 75%, at least 80%, at least 85%, at least 90%, at least 95%, or greater, identity to a β-PHLS polypeptide from lavender, tomato, pine, grand fir or spruce as set forth in FIG. 9a-9d. Typically, the level of activity is equivalent to the activity exhibited by a natural β-phellandrene synthase polypeptide to produce β-phellandrene. A β-phellandrene synthase polypeptide suitable for producing β-phellandrene has at least 20%, at least 30%, at least 40%, at least 50%, at least 60%, at least 70%, at least 80%, at least 90%6 or at least 95%, or greater, of the activity of an endogenous β-PHLS polypeptide from a plant, such as lavender, grand fir, tomato, and spruce.

Activity of a β-phellandrene synthase can be assayed by methods known to those skilled in the art. Non-limiting examples of assays that measure the function of β-phellandrene synthase to produce terpenes from the substrate GPP or NPP include in vitro enzymatic assays using purified recombinant β-phellandrene synthase protein, assays that determine the enzyme saturation kinetics, GC and GC-MS analysis and/or spectrophotometric analysis to measure terpene production (e.g., as detailed description in the Examples.

β-Phellandrene Synthase Expression Constructs

β-PHLS nucleic acid sequences are expressed recombinantly in cyanobacteria. Expression constructs can be designed taking into account such properties as codon usage frequencies of the organism in which the β-PHLS nucleic acid is to be expressed. Codon usage frequencies can be tabulated using known methods (see, e.g., Nakamura et al. Nucl. Acids Res. 28:292 (2000)). Codon usage frequency tables, including those for cyanobacteria, are also available in the art (e.g., in codon usage databases of the Department of Plant Genome Research, Kazusa DNA Research Institute, Japan).

Isolation or generation of β-PHLS polynucleotide sequences can be accomplished by well-known techniques, including amplification techniques and/or library screening.

Appropriate primers and probes for generating a β-PHLS gene can be designed based on known principles using, e.g., the β-PHLS sequences provided herein. For a general overview of PCR see PCR Protocols: A Guide to Methods and Applications. (Innis, M, Gelfand, D., Sninsky, J. and White, T., eds.), Academic Press, San Diego (1990). An illustrative PCR for amplifying a β-PHLS nucleic acid sequence is provided in the examples.

β-PHLS nucleic acid sequences for use in the invention include genes and gene products identified and characterized by techniques such as hybridization and/or sequence analysis using an exemplary nucleic acid sequence. In some embodiments, β-PHLS nucleic acid sequence for use in the invention encodes a β-PHLS polypeptide that has at least 70%, typically at least 75%, at least 80%, at least 85%, at least 90%, at least 95%, or greater, identity to a β-PHLS polypeptide from lavender, tomato, pine, grand fir or spruce as set forth in FIG. 9a-9d. Such β-PHLS also comprise a conserved domain as set forth in. In some embodiments, a β-PHLS nucleic acid sequence for use in the invention has at least 70%, at least 75%, at least 80%, at least 85%, or at least 90% to any one of SEQ ID NOS: 1-6, exclusive of the restriction sites at the ends of the sequences. In some embodiments, a β-PHLS nucleic acid sequence for use in the invention has at least 90%, at least 91%, at least 92%, at least 93%, at least 94%, at least 95%, at least 96%, at least 97%, at least 98%, at least 99% identity to any one of SEQ ID NOS: 1-6. In some embodiments the β-PHLS nucleic acid sequence comprises any one of SEQ ID NOS: 1-6, exclusive of the restriction sites at the ends of the sequences.

Fusion Constructs Comprising a β-PHLS Polypeptide and Leader Sequence

In the present disclosure, nucleic acid constructs are typically created in which a polynucleotide sequence encoding a β-PHLS encodes a version in which the β-PHLS is fused to the C-terminal end of a polynucleotide that encodes a leader protein, i.e., a protein that is expressed at high levels in cyanobacteria as described herein. In the context of the present invention, a protein that is "expressed at high levels in cyanobacteria" refers to a protein that accumulates to at least 1% of total cellular protein as described herein. Such proteins, when fused at the N-terminus of a protein of interest to be expressed in cyanobacteria, are also referred to herein as "leader proteins", "leader peptides", or "leader sequences". A nucleic acid encoding a leader protein is typically referred to herein as a "leader polynucleotide" or "leader nucleic acid sequence" or "leader nucleotide sequence".

The β-PHLS protein of interest is also expressed at high levels in conjunction with the leader sequence. In the context of the invention, a β-PHLS protein that is "expressed at high levels" in cyanobacteria refers to a β-PHLS protein that is at least 1%, typically at least 2%, at least 3%, at least 4%, at least 5%, or at least 10%, or greater, of the total protein expressed in the cyanobacteria. Expression levels in cyanobacteria may be evaluated in cells that are logarithmically growing, but may be alternatively determined in cells in a stationary phase of growth. The level of protein expression can be assessed using various techniques. In the present invention, high level expression is typically determined using SDS PAGE analysis. Following electrophoresis, the gel is stained and the level of proteins assessed by scanning the gel and quantifying the amount of protein using an image analyzer.

In some embodiments, a leader sequence use in this disclosure encodes a naturally occurring cyanobacteria protein that is expressed at high levels in native cyanobacteria. Thus, in some embodiments, the protein is endogenous to cyanobacteria. Examples of such proteins include cpcB, cpcA, cpeA, cpeB, apcA, apcB, rbcL, rbcS, psbA, rpl, or rps. In some embodiments, the leader sequence encodes less than the full-length of the protein, but typically comprises a region that encodes at least 25%, typically at least 50%, or at least 75%, or at least 90%, or at least 95%, or greater, of the length of the protein. As appreciated by one of skill in the art, use of an endogenous cyanobacterial polynucleotide sequence for constructing an expression construct in accordance with the invention provides a sequence that need not be codon-optimized, as the sequence is already expressed at high levels in cyanobacteria. Examples of cyanobacterial polynucleotides that encode cpcB, cpcA, cpeA, cpeB, apcA, apcB, rbcL, rbcS, psbA, rpl, or rps are available at the website www.genome.microbedb.jp/cyanobase under accession numbers, as follows:

cpcA: *Synechocystis* sp. PCC6803 sll1578, *Anabaena* sp. PCC7120 ar10529, *Thermosynechococcus elongatus* BP-1 tlr1958, *Synechococcus elongatus* PCC6301 syc0495_c, syc0500_c cpcB: *Synechocystis* sp. PCC6803 sl11577, *Anabaena* sp. PCC7120 ar10528, *Thermosynechococcus elongatus* BP-1 tlr1957, *Synechococcus elongatus* PCC6301 syc0496_c, syc0501_c cpeA: *Prochlorococcus marinus* SS120 Pro0337, *Synechococcus* sp. WH8102 SYNW2009, SYNW2016 cpeB: *Prochlorococcus marinus* SS120 Pro0338, *Synechococcus* sp. WH8102 SYNW2008, SYNW2017 apcA: *Synechocystis* sp. PCC 6803, slr2067; *Anabaena* sp. PCC 7120, a110450, alr0021; *Synechococcus elongalus* PCC 6301, syc 1186_d apcB: *Synechocystis* sp. PCC 6803, slr1986, *Anabaena* sp. PCC 7120, alr0022, *Synechococcus elongatus* PCC 6301, syc 1187_d rbcL RubisCO large subunit: *Synechocystis* sp. PCC 6803 slr0009 rbcS RubisCO small subunit: *Synechocystis* sp. PCC 6803 sir0012 rpl: 50S ribosomal protein of *Synechocystis*. e.g. sl11803; sll1810; ssr1398.

rps: 30S ribosomal protein of *Synechocystis*, e.g. sll1804; slr1984.

In some embodiments, the leader sequence is a cpcB gene and the other cpc genes of the endogenous cpc operon are maintained in place downstream of the recombinant construct.

The polynucleotide sequence that encodes the leader protein need not be 100% identical to a native cyanobacteria polynucleotide sequence. A polynucleotide variant having at least 50% identity or at least 60% identity, or greater, to a native cyanobacterial polynucleotide sequence, e.g., a native cpcB, cpcA, cpeA, cpeB, rbcL, rbcS, psbA, rpl, or rps cyanobacteria polynucleotide sequence, may also be used, so long as the codons that vary relative to the native cyanobacterial polynucleotide are codon optimized for expression in cyanobacteria and the codons that vary relative to the wild type sequence do not substantially disrupt the structure of the protein. In some embodiments, a polynucleotide variant that has at least 70% identity, at least 75% identity, at least 80% identity, or at least 85% identity, or greater to a native cyanobacterial polynucleotide sequence, e.g., a native cpcB, cpcA, cpeA, cpeB, rbcL, rbcS, psbA, rpl, or rps cyanobacteria polynucleotide sequence, is used, again maintaining codon optimization for cyanobacteria. In some embodiments, a polynucleotide variant that has least 90% identity, or at least 95% identity, or greater, to a native cyanobacterial polynucleotide sequence, e.g., a native cpcB, cpcA, cpeA, cpeB, rbcL, rbcS, psbA, rpl, or rps cyanobacteria polynucleotide sequence, is used. The percent identity is typically determined with reference the length of the polynucleotide that is employed in the construct, i.e., the percent identity may be over the full length of a polynucleotide that encodes the leader polypeptide sequence, or may be over a smaller length, e.g., in embodiments where the polynucleotide encodes at least 25%, typically at least 50%, or at least 75%, or at least 90%, or at least 95%, or greater, of the length of the protein. The protein encoded by a variant polynucleotide sequence as described need not retain a biological function, however, a codon that varies from the wild-type polynucleotide is typically selected such that the protein structure of the native cyanobacterial sequence is not substantially altered by the changed codon, e.g., a codon that encodes an amino acid that has the same charge, polarity, and/or is similar in size to the native amino acid is selected.

In some embodiments, a polynucleotide variant of a naturally over-expressed (more than 1% of the total cellular protein) cyanobacterial gene is employed, that encodes for a polypeptide sequence that has at least 70%, or 80%, or at least 85% or greater identity to the protein encoded by the wild-type gene. In some embodiments, the polynucleotide encodes a protein that has 90% identity, or at least 95% identity, or greater, to the protein encoded by the wild-type gene. Variant polynucleotides are also codon optimized for expression in cyanobacteria.

In some embodiments, a protein that is expressed at high levels in cyanobacteria is not native to cyanobacteria in which a fusion construct in accordance with the invention is expressed. For example, polynucleotides from bacteria or other organisms that are expressed at high levels in cyanobacteria may be used as leader sequences. In such embodiments, the polynucleotides from other organisms are codon-optimized for expression in cyanobacteria. In some embodiments, codon optimization is performed such that codons used with an average frequency of less than 12% by *Synechocystis* are replaced by more frequently used codons. Rare codons can be defined, e.g., by using a codon usage table derived from the sequenced genome of the host cyanobacterial cell. See, e.g., the codon usage table obtained from Kazusa DNA Research Institute, Japan (website www.kazusa.or.jp/codon/) used in conjunction with software, e.g., "Gene Designer 2.0" software, from DNA 2.0 (website www.dna20.com/) at a cut-off thread of 15%.

In some embodiments, a leader sequence in accordance with the present invention encodes a protein that confers antibiotic resistance. An example of such a leader sequence encodes neomycin phosphotransferase e.g., NPT1, which confers neomycin and kanamycin resistance. Other polynucleotides that may be employed include a chloramphenicol acetyltransferase polynucleotide, which confers chloramphenicol resistance; or a polynucleotide encoding a protein that confers streptomycin, ampicillin, or tetracycline resistance, or resistance to another antibiotic. In some embodiments, the leader sequence encodes less than the full-length of the protein, but typically comprises a region that encodes at least 25%, typically at least 50%, or at least 75%, or at least 90%, or at least 95%, or greater, of the length of the protein. In some embodiments, a polynucleotide variant of a naturally occurring antibiotic resistance gene is employed. As noted above, a variant polynucleotide need not encode a protein that retains the native biological function. A variant polynucleotide typically encodes a protein that has at least 80% identity, or at least 85% or greater, identity to the protein encoded by the wild-type antibiotic resistance gene. In some embodiments, the polynucleotide encodes a protein that has 90% identity, or at least 95% identity, or greater, to the wild-type antibiotic resistance protein. Such variant polynucleotides employed as leader sequence are also codon-optimized for expression in cyanobacteria. The percent identity is typically determined with reference to the length of the polynucleotide that is employed in the construct, i.e., the percent identity may be over the full length of a polynucleotide that encodes the leader polypeptide sequence, or may be over a smaller length, e.g., in embodiments where the polynucleotide encodes at least 25%, typically at least 50%, or at least 75%, or at least 90%, or at least 95%, or greater, of the length of the protein. A protein encoded by a variant polynucleotide sequence need not retain a biological function, however, codons that are present in a variant polynucleotide are typically selected such that the protein structure relative to the wild-type protein structure is not substantially altered by the changed codon, e.g., a codon that encodes an amino acid that has the same charge, polarity, and/or is similar in size to the native amino acid is selected.

Other leader proteins can be identified by evaluating the level of expression of a candidate leader protein in cyanobacteria. For example, a leader polypeptide that does not occur in wild type cyanobacteria may be identified by measuring the level of protein expressed from a polynucleotide codon optimized for expression in cyanobacteria that encodes the candidate leader polypeptide. A protein may be selected for use as a leader polypeptide if the protein accumulates to a level of at least 1%, typically at least 2%, at least 3%, at least 4%, at least 5%, or at least 10%, or greater, of the total protein expressed in the cyanobacteria when the polynucleotide encoding the leader polypeptide is introduced into cyanobacteria and the cyanobacteria cultured under conditions in which the transgene is expressed. The level of protein expression is typically determined using SDS PAGE analysis. Following electrophoresis, the gel is scanned and the amount of protein determined by image analysis.

Constructs Comprising a β-PHLS Gene

To use isolated sequences in the above techniques, recombinant DNA vectors suitable for transformation of cyanobacteria are prepared. Techniques for transformation are well known and described in the technical and scientific literature. For example, a DNA sequence encoding a β-PHLS gene (described in further detail below), can be combined with transcriptional and other regulatory sequences which will direct the transcription of the sequence from the gene in the intended cells of the transformed cyanobacteria. In some embodiments, an expression vector that comprises an expression cassette that comprises the β-PHLS gene further comprises a promoter operably linked to the β-PHLS gene. In other embodiments, a promoter and/or other regulatory elements that direct transcription of the β-PHLS gene are endogenous to the cyanobacteria and the expression cassette comprising the β-PHLS gene is introduced, e.g., by homologous recombination, such that the heterologous β-PHLS gene is operably linked to an endogenous promoter and is expression driven by the endogenous promoter.

Regulatory sequences include promoters, which may be either constitutive or inducible. In some embodiments, a promoter can be used to direct expression of β-PHLS nucleic acids under the influence of changing environmental conditions. Examples of environmental conditions that may affect transcription by inducible promoters include anaerobic conditions, elevated temperature, or the presence of light. Promoters that are inducible upon exposure to chemicals reagents are also used to express β-PHLS nucleic acids. Other useful inducible regulatory elements include copper-inducible regulatory elements (Mett et al., Proc. Natl. Acad. Sci. USA 90:4567-4571 (1993); Furst et al., Cell 55:705-717 (1988)); tetracycline and chlor-tetracycline-inducible regulatory elements (Gatz et al., Plant J. 2:397-404 (1992); Röder et al., Mol. Gen. Genet. 243:32-38 (1994); Gatz, Meth. Cell Biol. 50:411-424 (1995)); ecdysone inducible regulatory elements (Christopherson et al., Proc. Natl. Acad. Sci. USA 89:6314-6318 (1992); Kreutzweiser et al., Ecotoxicol. Environ. Safety 28:14-24 (1994)); heat shock inducible promoters, such as those of the hsp70/dnaK genes (Takahashi et al., Plant Physiol. 99:383-390 (1992); Yabe et al., Plant Cell Physiol. 35:1207-1219 (1994); Ueda et al., Mol. Gen. Genet. 250:533-539 (1996)); and lac operon elements, which are used in combination with a constitutively expressed lac repressor to confer, for example, IPTG-inducible expression (Wilde et al., EMBO J. 11:1251-1259 (1992)). An inducible regulatory element also can be, for example, a nitrate-inducible promoter, e.g., derived from the spinach nitrite reductase gene (Back et al., Plant Mol. Biol. 17:9 (1991)), or a light-inducible promoter, such as that associated with the small subunit of RuBP carboxylase or the LHCP gene families (Feinbaum et al., Mol. Gen. Genet. 226:449 (1991): Lam and Chua, Science 248:471 (1990)), or a light.

In some embodiments, the promoter may be from a gene associated with photosynthesis in the species to be transformed or another species. For example such a promoter from one species may be used to direct expression of a protein in transformed cyanobacteria cells. Suitable promoters may be isolated from or synthesized based on known sequences from other photosynthetic organisms. Preferred promoters are those for genes from other photosynthetic species, or other photosynthetic organism where the promoter is active in cyanobacteria.

In some embodiments, a promoter used to drive expression of a heterologous β-PHLS gene is a constitutive promoter. Examples of constitutive strong promoters for use in cyanobacteria include, for example, the psbDI gene or the basal promoter of the psbD II gene. Various other promoters that are active in cyanobacteria are also known. These include the light inducible promoters of the psbA1, psbA2, and psbA3 genes in cyanobacteria and promoters such as those set forth in U.S. Patent Application Publication No. 20020164706, which is incorporated by reference. Other promoters that are operative in plants, e.g., promoters derived from plant viruses, such as the CaMV35S promoters, can also be employed in cyanobacteria. For a description of strong and regulated promoters, e.g., active in the cyanobacterium *Anabaena* sp, strain PCC 7120, see e.g., Elhai, FEMS Microbiol Lett 114:179-184, (1993)). In other embodiments, other locus in the cyanobacterial chloroplast genome can be used to drive expression of the heterologous β-PHLS gene, provided that the locus permits relatively high expression levels of the heterologous gene. In some embodiments, the promoter is a cpc promoter, a Ptrc promoter, or a T7 promoter.

In some embodiments, promoters are identified by analyzing the 5' sequences of a genomic clone corresponding to a β-PHLS gene. Sequences characteristic of promoter sequences can be used to identify the promoter.

A promoter can be evaluated, e.g., by testing the ability of the promoter to drive expression in cyanobacteria in which it is desirable to introduce a β-PHLS expression construct.

A vector comprising β-PHLS nucleic acid sequences will typically comprise a marker gene that confers a selectable phenotype on cyanobacteria transformed with the vector. Such markers are known. For example, the marker may encode antibiotic resistance, such as resistance to chloramphenicol, kanamycin, G418, bleomycin, hygromycin, and the like.

Heterologous Expression of β-Phellandrene Synthase Gene in Unicellular Microorganisms Cell transformation methods and selectable markers for cyanobacteria are well known in the art (Wirth, Mol. Gen. Genet., 216(1):175-7 (1989); Koksharova, Appl. Microbiol. Biotechnol., 58(2): 123-37 (2002): Thelwell et al., Proc. Natl. Acad. Sci. U.S.A., 95:10728-10733 (1998)). Transformation methods and selectable markers for are also well known (see. e.g., Sambrook et al., supra).

A codon-optimized β-phellandrene synthase gene as described in this disclosure can be expressed in any number of cyanobacteria where it is desirable to produce a blend of terpenes. Suitable unicellular cyanobacteria include *Synechocystis* sp., such as strain *Synechocystis* PCC 6803; and *Synechococcus* sp., e.g., the thermophilic *Synechococcus lividus*: the mesophilic *Synechococcus elongatus* or *Synechococcus* 6301. Multicellular, including filamentous cyanobacteria, may also be engineered to express β-PHLS in accordance with this invention. Multicellular cyanobacteria that can be used include, e.g., Gloeocapsa, as well as filamentous cyanobacteria such as *Nostoc* sp., e.g., *Nostoc* sp. PCC 7120, *Nostoc sphaeroides*): *Anabaena* sp., e.g., *Anabaena variabilis*, and *Arthrospira* sp. ("*Spirulina*"), such as *Arthrospira platensis* and *Arthrospira maxima*. Cyanobacteria that are genetically modified in accordance with this disclosure to express a β-PHLS gene may also contain other genetic modifications, e.g., modifications to the terpenoid pathway, to enhance production of terpenes.

In some embodiments, an expression construct is generated to allow the heterologous expression of the β-phellandrene synthase gene in *Synechocystis* through the replacement of the *Synechocystis* PsbA2 gene with the codon-optimized β-PHLS gene via double homologous recombination. In some embodiments, the expression construct comprises a codon-optimized β-phellandrene synthase gene operably linked to an endogenous cyanobacteria promoter. In some aspects, the promoter is the PsbA2 promoter.

In some embodiments, cyanobacteria are transformed with an expression vector comprising a β-PHLS gene and an antibiotic resistance gene. A detailed description is set forth in PCT Application No. PCT/US2007/71465, which is incorporated by reference. Transformants are cultured in selective media containing an antibiotic to which an untransformed host cell is sensitive. Cyanobacteria normally have up to 100 copies of identical circular DNA chromosomes in each cell. Successful transformation with an expression vector comprising a β-PHLS gene and an antibiotic resistance gene normally occurs in only one, or just a few, of the many cyanobacterial DNA copies. Hence, presence of the antibiotic is necessary to encourage expression of the transgenic copy(ies) of the DNA for terpene production. In the absence of the selectable marker (antibiotic), the transgenic copy(ies) of the DNA would be lost and replaced by wild-type copies of the DNA.

In some embodiments, cyanobacterial transformants are cultured under continuous selective pressure conditions (presence of antibiotic over many generations) to achieve DNA homoplasmy in the transformed host organism. One of skill in the art understands that the number of generations and length of time of culture varies depending on the particular culture conditions employed. Homoplasmy can be determined, e.g., by monitoring the DNA composition in the cells to determine the presence of wild-type copies of the cyanobacterial DNA.

"Achieving homoplasmy" refers to a quantitative replacement of most, e.g., 70% or greater, or typically all, wild-type copies of the cyanobacterial DNA in the cell with the transformant DNA copy that carries the β-PHLS transgene. This is normally attained over time, under the continuous selective pressure (antibiotic) conditions applied, and entails the gradual during growth replacement of the wild-type copies of the DNA with the transgenic copies, until no wild-type copy of the cyanobacterial DNA is left in any of the transformant cells. Achieving homoplasmy is typically verified by quantitative amplification methods such as genomic-DNA PCR using primers and/or probes specific for the wild-type copy of the cyanobacterial DNA. In some embodiments, the presence of wild-type cyanobacterial DNA can be detected by using primers specific for the wild-type cyanobacterial DNA and detecting the presence of the PsbA2 gene. Transgenic DNA is typically stable under homoplasmy conditions and present in all copies of the cyanobacterial DNA.

In some embodiments, cyanobacterial cultures can be cultured under conditions in which the light intensity is varied. Thus, for example, when a psbA2 promoter is used as a promoter to drive β-phellandrene synthase expression, transformed cyanobacterial cultures can be grown at low light intensity conditions (e.g., 10-50 µmol photons $m^{-2}\ s^{-1}$), then shifted to higher light intensity conditions (e.g., 500 µmol photons $m^{-2}\ s^{-1}$). The psbA2 promoter responds to the shift in light intensity by up-regulating the expression of the β-PHLS gene in *Synechocystis*, typically at least about 10-fold. In other embodiments, cyanobacterial cultures can be exposed to increasing light intensity conditions (e.g., from 50 µmol photons $m^{-2}\ s^{-1}$ to 2,500 µmol photons $m^{-2}\ s^{-1}$) corresponding to a diurnal increase in light intensity up to full sunlight. The psbA2 promoter responds to the gradual increase in light intensity by up-regulating the expression of the β-PHLS gene in *Synechocystis* in parallel with the increase in light intensity.

Blends of monoterpenes can also be obtained by expressing a β-phellandrene synthase as described herein in unicellular photosynthetic microorganisms other than cyanobacteria. Such organisms include green algae, diatoms, and red algae. Illustrative green algae include *Chlamydomonas reinhardtii; Dunaliella salina; Chlorella fusca; Chlorella vulgaris; Scenedesmus obliquus: Botryococcus braunii*. Examples of diatoms that can be modified to express a β-phellandrene synthase in accordance with this disclosure to produce a blend of monoterpenes include *Pheodactylum tricornutum: Cylindrotheca fusiformis; Cyclotella gamma; Nannochloropsis oceanica*; and *Thalassiosira pseudonana*. Examples of red algae that can be modified to express a β-phellandrene synthase in accordance with this disclosure to produce a blend of monoterpenes include *Porphyridium cruentum: Cyanidioschyzon merolae; Flintiella sanguinaria*; and *Rhodosorus marinus*

Production of Monoterpene Hydrocarbon Blends in Cyanobacteria

Transformed cyanobacteria (transformant cyanobacteria) are grown under conditions in which the heterologous β-PHLS gene is expressed. Methods of mass culturing cyanobacteria are known to one skilled in the art. For example, cyanobacteria can be grown to high cell density in photobioreactors (see, e.g., Lee et al., Biotech. Bioengineering 44:1161-1167, 1994; Chaumont, J Appl. Phycology 5:593-604, 1990). Examples of photobioreactors include cylindrical or tubular bioreactors, see, e.g., U.S. Pat. Nos. 5,958,761, 6,083,740, US Patent Application Publication No. 2007/0048859: WO 2007/011343, and WO 2007/098150. High density photobioreactors are described in, for example, Lee, et al., Biotech. Bioengineering 44: 1 161-1 167, 1994. Other photobioreactors suitable for use in the invention are described. e.g., in WO 2011/034567 and references cited in the background section. Photobioreactor parameters that can be optimized, automated and regulated for production of photosynthetic organisms are further described in (Puiz (2001) Appl Microbiol Biotechnol 57:287-293). Such parameters include, but are not limited to, materials of construction, efficient light incidence into reactor lumen, light path, layer thickness, oxygen released, salinity and nutrients, pH, temperature, turbulence, optical density, and the like.

Transformed cyanobacteria that express a heterologous β-PHLS gene are grown under mass culture conditions for the production of monoterpene hydrocarbons. In typical embodiments, the transformed organisms are growth in bioreactors or fermentors that provide an enclosed environment. For example, in some embodiments for mass culture, the cyanobacteria are grown in enclosed reactors in quantities of at least about 500 liters, often of at least about 1000 liters or greater, and in some embodiments in quantities of about 1,000,000 liters or more. One of skill understands that large-scale culture of transformed cyanobacteria that comprise a β-phellandrene synthase gene where expression is driven by a light sensitive promoter, such as a PsbA2 promoter, is typically carried out in conditions where the culture is exposed to natural light. Accordingly, in such embodiments appropriate enclosed reactors are used that allow light to reach the cyanobacteria culture.

Growth media for culturing cyanobacteria transformants are well known in the art. For example, cyanobacteria may be grown on solid media such as BG-11 media (see, e.g., Rippka et al., J. Gen Microbiol, 111:1-61, 1979). Alternatively, they may be grown in liquid media (see, e.g., Bentley & Melis, Biotechnol. Bioeng. 109:100-109, 2012). In typical embodiments for production of monterpenes, liquid cultures are employed. For example, such a liquid culture may be maintained at about 25° C. under a slow stream of constant aeration and illumination, e.g., at 20 µmol photons m$^{-2}$ s$^{-1}$. In certain embodiments, an antibiotic, e.g., chloramphenical, is added to the liquid culture. For example, chloramphenicol may be used at a concentration of 15 µg/ml.

In some embodiments, cyanobacteria transformants are grown photoautotrophically in a gaseous/aqueous two-phase photobioreactor (see, e.g., Bentley & Melis. 2012, supra, and WO 2012/145692). In certain embodiments, the methods of the present invention comprise obtaining a blend of monoterpenes produced by the cyanobacteria using a diffusion-based method for spontaneous gas exchange in a gaseous/aqueous two-phase photobioreactor. In particular aspects of the method, carbon dioxide is used as a feedstock for the photosynthetic generation in cell culture and the headspace of the bioreactor is filled with 100% $CO^2$ and sealed.

Conditions for growing β-PHLS-expressing cyanobacteria for the purposes illustrated above are known in the art (see, e.g., the illustrative references cited herein). Monoterpene hydrocarbons produced by the modified cyanobacteria can be harvested using known techniques. Monoterpene hydrocarbons are not miscible in water and they rise to and float at the surface of the microorganism growth medium. In typical embodiments, they are siphoned off from the surface and sequestered in suitable containers. In addition, and depending on the prevailing temperature during the mass cultivation of the cyanobacteria, monoterpene can exist in vapor form above the water medium in the bioreactor container (monoterpene hydrocarbons have a relatively high boiling temperature T=170-175° C.). In some embodiments, monoterpene vapor is piped off the bioreactor container and condensed into liquid 1 form upon cooling or low-level compression.

In typical embodiments, the photosynthetically produced monoterpene blend is in liquid form and floating on the aqueous phase of the liquid culture. The blend of monoterpene hydrocarbons typically comprises at least two, or at least three monoterpenes selected from the group consisting of β-phellandrene, α-phellandrene, β-myrcene, β-pinene, and δ-2-carene with variable percentage ratios, e.g., ranging from <10% to >90% with different product combinations and proportions. In some embodiments, a blend of monoterpene hydrocarbons produced in accordance with the disclosure may also comprise one or more of α-pinene, terpinene, ocimene or limonene. These hydrophobic monoterpenes spontaneously diffuse out of the cyanobacterial cells that generate them and accumulate as floater molecules on the surface of the liquid culture.

In some embodiments, extraction of the terpenes produced in accordance with the invention is performed by skimming the floating terpenes from the surface of the liquid phase of the culture and isolating the terpenes. In certain embodiments, photosynthetically produced non-miscible monoterpenes in liquid form are extracted from the liquid phase by a method comprising overlaying a solvent such as heptane, decane, or dodecane, on top of the liquid culture in the bioreactor, incubating for at room temperature, e.g. 30 minutes or longer; and removing the solvent, e.g., heptane, layer containing monoterpenes. In some embodiments, photosynthetically produced monoterpenes are a volatile product accumulating in the headspace of the bioreactor.

EXAMPLES

The examples described herein are provided by way of illustration only and not by way of limitation. Those of skill in the art will readily recognize a variety of non-critical parameters that could be changed or modified to yield essentially similar results The following examples illustrate the over-expression of β-phellandrene synthase and isoprene synthase in cyanobacteria.

Materials and Methods

*Synechocystis* Strains, Recombinant Constructs, and Culturing Conditions

*Synechocystis* sp. PCC 6803 was used as the recipient strain and referred to as the wild type (wt) in this study. The PHLS sequences from *Solanum* llvcopersicum (tomato; AC056896.1), *Pinus banksiana* (pine; AFU73854.1), *Picea sitchensis* (Sitka spruce; ADZ45506.1), and *Abies grandis* (grand fir; AAF61453.1), and the NPPS sequence from *Solanum lycopersicum* (AC056895.1), were codon optimized for expression in *Synechocystis*, after removal of the putative chloroplast transit peptide, as predicted by ChloroP (Emanuelsson et al. 1999). The resulting nucleotide sequences (table of sequences) were synthesized at Biomatik (http://wwv.biomatik.com/) with the NdeI and BglII restriction sites at the 5' and 3'-end, respectively, for subsequent cloning in the corresponding sites of the CpcB·PHLS+Cpce plasmid. This plasmid was the same, as that previously employed for expression of the *Lavandula angustifolia* (lavender) PHLS as a fusion with the *Synechocystis* phycocyanin β-subunit (CpcB) under control of the strong cpe operon promoter (Formighieri and Melis 2015). The NPPS encoding sequence, including the CpcA ribosome-binding site, was additionally cloned in an operon configuration downstream of the SIPHLS transgene via BglII and NotI. The recombinant plasmids used in this work have been deposited and can be made available through Addgene (<https://www.addgene.org/Anastasios_Melis>).

*Synechocystis* transformations and growth conditions were made according to established protocol (Williams 1988, Eaton-Rye 2011). Wild type and transformants were maintained on 1% agar BG11 media supplemented with 10 mM TES-NaOH (pH 8.2) and 0.3% sodium thiosulfate. Liquid cultures in BG11 were buffered with 25 mM phosphate (pH 7.5) and incubated under continuous low-stream bubbling with air at 28° C. Transgenic DNA copy homoplasmy was achieved with cells incubated on agar in the presence of 30 µg/mL chloramphenicol, 5 mM glucose, under illumination of 170 µmol photons m$^{-2}$ s$^{-1}$.

Genome integration of the recombinant cassette in the cpe locus, and attainment of transgenic DNA copy homoplasmy were verified by genomic DNA PCR analysis, using primers cpc_us and cpcA_Rv (Formighieri and Melis 2015). The cpc_us primer was also coupled in a PCR reaction with specific oligonucleotides designed to recognize each PHLS sequence: 5'-AATCCAGGCACTGTGGGAAG-3' (SIPHLS_Rv) (SEQ ID NO:43), 5'-CACGACCGATGCC-TTCTC-3' (PbPHLS_Rv) (SEQ ID NO:44), 5'-TTTCGAGCTTCTAATCGTGGC-3' (PsPHLS_Rv) (SEQ ID NO:45), 5'-ATTGCGAGTTTCCAACCGAG-3' (AgPHLL_Rv) (SEQ ID NO:46). Presence of the NPPS sequence was verified in a PCR reaction using the specific oligonucleotide (NPPS_Fw, 5'-TCGCTGGGCCAAAGA-TAAGG-3') (SEQ ID NO:47) and cpcA_Rv.

Protein Analysis and Monoterpenes Production by *Synechocystis* Transformants

Protein extraction from cell lysates was performed as described (Formighieri and Melis 2015). Total cell proteins were subsequently resolved by SDS-PAGE and Coomassie stained. Monoterpenes production and separation from *Synechocystis* cultures were performed as described (Bentley et al. 2013; Formighieri and Melis 2014a: Formighieri and Melis 2015). Typically, cells from mid-growth cultures were pelleted and resuspended in fresh medium at $OD_{730}$ nm=0.5, bubbled with 100% CO2 to fill the gaseous headspace of the gaseous-aqueous two-phase reactor (Bentley and Melis 2012), sealed and incubated for 48 h in the light. Monoterpene hydrocarbons spontaneously diffused out of the cells and were collected from the surface of the transformant cultures by applying a known volume of hexane overlayer. Monoterpene products were analyzed by UV-absorbance spectrophotometry and sensitive gas chromatography (GC-FID) (Formighieri and Melis 2014b, 2015). For PsPHLS and AgPHLS, whose corresponding *Synechocystis* transformants yielded low levels of monoterpene products, a splitless injection mode was used instead of a split ratio of 10.

Results

Example 1. Heterologous Expression and Activity of *Solanum lycopersicum* in *Synechocystis* Transformants The codon optimized sequence encoding for the *Solanum lycopersicum* PHLS (SlPHLS) was expressed under control of the strong endogenous cpc operon promoter as a fusion protein with the highly abundant in cyanobacteria phycocyanin β-subunit (CpcB). The other cpe genes of the endogenous cpc operon were maintained in place downstream of the recombinant construct (FIG. 1a). This strategy proved successful in over-expressing the PHLS from *Lavandula angustifolia* (Formighieri and Melis 2015). High concentrations of the enzyme in the cell help to overcome limitations in the rate and yield of monoterpene production due to the slow catalytic activity (slow $K_{cat}$) of terpene synthases (Formighieri and Melis 2015). A second construct (FIG. 1b) was designed to co-express SlPHLS with the neryl-diphosphate synthase of *Solanum lycopersicum* (SlNPPS) in an operon configuration. *Synechocystis* has an endogenous pool of GPP, but it lacks a NPPS activity. The second construct tested the requirement of NPP as a substrate for the catalytic activity of SlPHLS.

Both constructs were integrated in the cpc genomic locus of *Synechocystis* by double homologous recombination. The resulting transformants were screened by genomic DNA PCR analysis to test for the correct genome integration of the recombinant genes and attainment of transgenic DNA copy homoplasmy. A PCR amplifying the cpc upstream-to-cpcA region resulted in a 5128 bp product with the CpcB·SlPHLS+NPPS transformants, a 4344 bp product with CpcB·SlPHLS, and a 1289 bp product with the wild type (FIG. 1c). PCR amplification of the cpc upstream-to-SlPHLS region gave a 1321 bp product in the transformants only, and not in the wt (FIG. 1d), while amplification of the SlNPPS-to-cpcA specifically showed presence of the NPPS encoding sequence in the CpcB·SlPHLS+NPPS transformants (FIG. 1e, 1606 bp product).

Protein expression analysis was then performed by SDS-PAGE followed by Coomassie staining (FIG. 1f). While phycocyanin is the most abundant protein in wild type *Synechocystis* extracts (FIG. 1f, wt), the native CpcB was replaced by CpcB.SlPHLS fusion protein in the transformants, and could be seen in the Coomassie-stained gel with an expected molecular weight of 105 kD, both in CpcB·SlPHLS and CpcB·SlPHLS+NPPS transformants (FIG. 1f), offering clear evidence of over-expression. In contrast, the NPPS protein could not be detected in the CpcB·SlPHLS+NPPS transformants upon Coomassie-staining, indicating a lower level of expression.

In vivo activity of SlPHLS was assayed by measuring monoterpene hydrocarbons production by the CpcB·SlPHLS and CpcB·SlPHLS+NPPS *Synechocystis* transformants. The monoterpene products were collected as floater molecules from the surface of sealed cultures upon dilution with a known volume of hexane and siphoning-off the lipophilic phase. The hexane extracts from the CpcB·SlPHLS+NPPS transformants showed distinctive UV-absorbance spectra (Formighieri and Melis 2016), suggesting the presence of monoterpenes (FIG. 2a. CpcB·SlPHLS+NPPS). In contrast, the hexane extracts from the wild type and the CpcB·SlPHLS transformants resulted in a featureless flat absorbance (FIG. 2a, wt. CpcB·SlPHLS). This outcome was to be expected for the wild type that is not endowed with monoterpene biosynthesis, and it also indicated lack of hydrocarbons productivity by the CpcB·SlPHLS transformants. This result is consistent with the notion that SlPHLS alone cannot use the endogenous GPP pool in cyanobacteria, but it requires heterologous synthesis of NPP as substrate.

The monoterpene hydrocarbons profile of the CpcB·SlPHLS+NPPS transformants was additionally analyzed by GC-FID, showing the presence of a blend of monoterpenes produced under these conditions (FIG. 2b). β-Phellandrene was detected as the major product (74%), followed by α-phellandrene (20%) and β-myrcene (5%). Smaller amounts (~1%) of β-pinene and δ-2-carene were also detected. Limonene that was identified in tomato trichome extracts and apparently produced by the SlPHLS enzyme in vitro (Schilmiller et al. 2009) was not detected upon heterologous expression of the SlPHLS in *Synechocystis*. It is concluded that heterologous expression of the PHLS from tomato in *Synechocystis* results in the generation of substantially different and unique blends of monoterpenes.

Figures 3A, 3B, 3C, 3D:
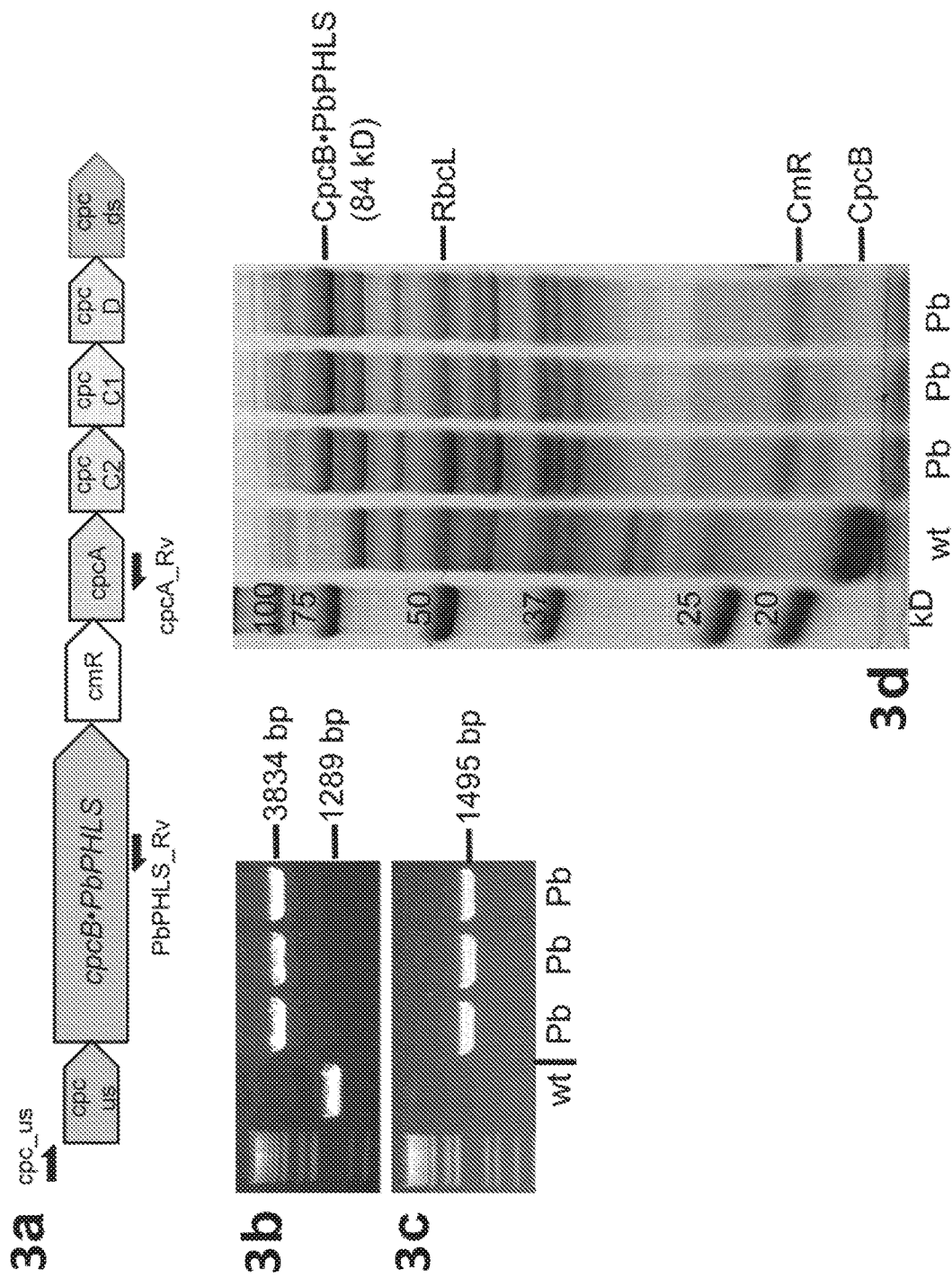
FIG. 3a-3d provides data illustrating the expression of *Pinus banksiana* (pine) β-phellandrene synthase (PbPHLS) in *Synechocystis*. 3a: Recombinant construct for expression of PbPHLS as a fusion to CpcB in the cpc genomic locus. 3b: Genomic PCR analysis with cpc_us and cpcA_Rv primers. 3c: Genomic PCR analysis with cpc_us and PbPHLS_Rv primers. Location of the primers is shown as arrows in (a). Pb denotes three independent transformants lines. 3d: SDS-PAGE resolution and Coomassie-stain of total cell protein extracts from *Synechocystis* wild type and transformants. The CpcB·PbPHLS fusion protein and the native CpcB are marked at 84 kD and 18 kD, respectively. Molecular weight markers are on the left side and expressed in kD.

Example 2. Heterologous Expression and Activity of *Pinus Banksiana* PHLS in *Synechocystis* Transformants The codon optimized sequence encoding the *Pinus banksiana* PHLS (PbPHLS) was expressed in *Synechocystis* in the cpc genomic locus as a fusion with CpcB (FIG. 3a). Correct genome integration and transgenic DNA copy homoplasmy were tested by genomic DNA PCR analysis. The cpc upstream-to-cpcA genomic region was PCR amplified and resulted in a 3834 bp product with the transformants as compared to the 1289 bp product corresponding to the wild type sequence (FIG. 3b). The cpc upstream-to-PbPHLS region was specifically amplified in the transformants only, resulting in a 1495 bp PCR product (FIG. 3c).

Protein expression was then investigated by SDS-PAGE analysis of total cell protein extracts. The CpcB·PbPHLS fusion protein was highly expressed in the *Synechocystis* transformants, clearly visible upon Coomassie staining of the gel (FIG. 3d, CpcB·PbPHLS, expected molecular weight of 84 kD).

Figures 2A, 2B:
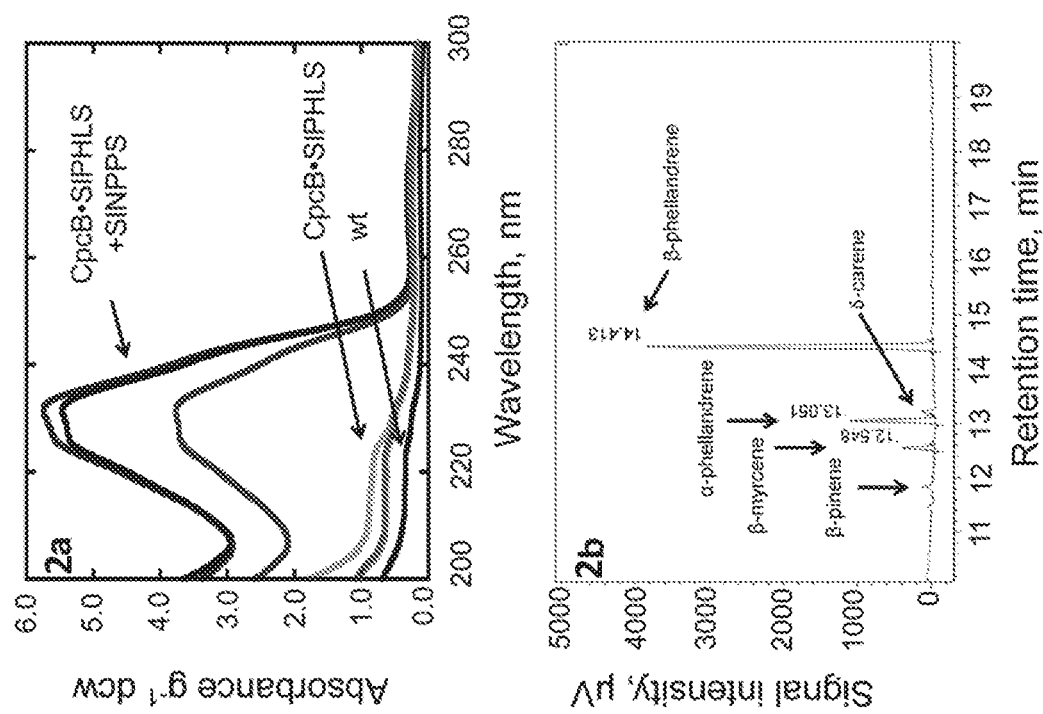
FIG. 2a-2b provides data illustrating monoterpene production by *Synechocystis* transformants expressing the SIPHLS construct with or without NPPS transgene. Cells in liquid culture were grown photoautotrophically for 48 h. 2a: UV-absorbance spectra of hexane extracts from *Synechocystis* CpcB·SIPHLS+NPPS and CpcB·SIPHLS transformants, normalized on per g of dry cell weight (dcw) and compared to wild type (wt) extracts. 2b: GC-FID analysis of the monoterpenes isolated from the CpcB·SIPHLS+NPPS transformants. β-Phellandrene, α-phellandrene and β-myrcene were detected as the main terpene products with retention time of 14.413 min, 13.051 min, and 12.548 min, respectively. Small amounts of β-pinene (about 11.6-11.8 min) and δ-carene (about 13.2 min) were also detected.
Figures 4A, 4B:
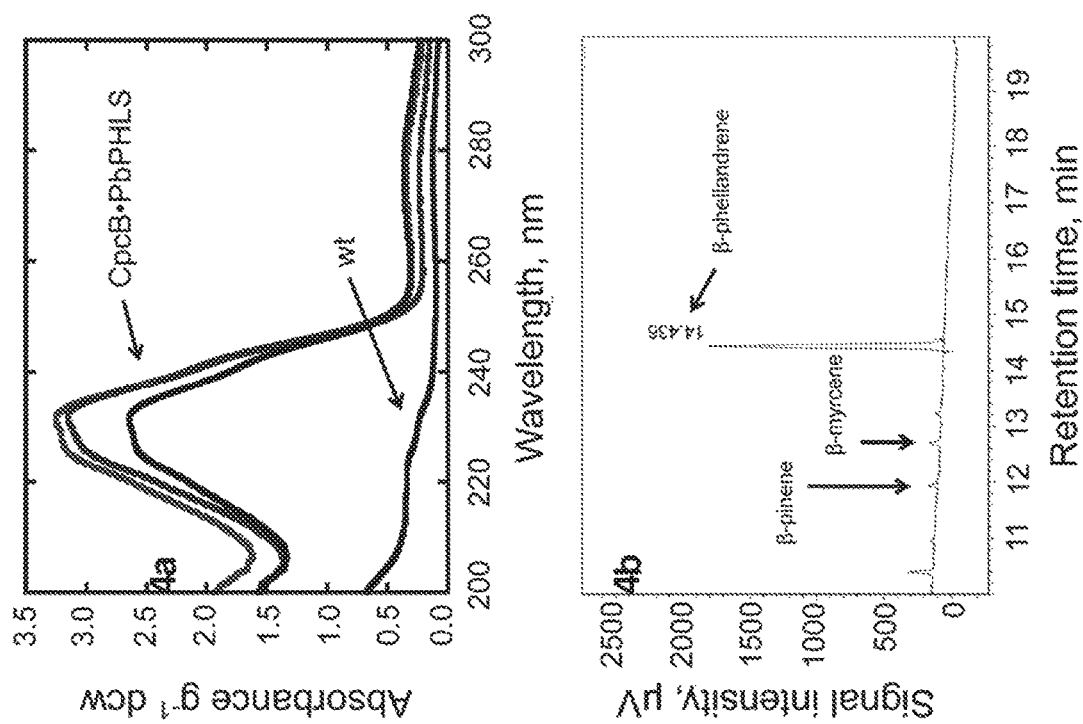
FIG. 4a-4b provides data illustrating monoterpene production by *Synechocystis* transformants expressing PbPHLS. 4a: UV-absorbance spectra of hexane extracts from *Synechocystis* CpcB·PbPHLS transformants, normalized on per g of dcw and compared to wild type (wt) extracts. 4b: GC-FID analysis of the hexane extract from the CpcB·PbPHLS transformants, showing β-phellandrene to be the primary product with a retention time of 14.436 min. Small amounts of β-pinene (about 11.6-11.8 min) and β-myrcene (12.6 min) were also detected.

When assayed for monoterpene production, the CpcB·PbPHLS transformants showed a distinctive UV-absorbance spectrum of the hexane extracts as compared to the wild type, suggesting activity of the PbPHLS upon heterologous expression in *Synechocystis* (FIG. 4a). Analysis of the monoterpene products by GC-FID showed β-phellandrene as the dominant product, suggesting high product specificity of the PbPHLS enzyme toward this monoterpene hydrocarbon (FIG. 4b). Considerably smaller amounts of β-pinene and β-myrcene were also detected (<2%). The relatively higher specificity of cyanobacteria transformants for the β-phellandrene product affords an advantage over oleoresin extracts from *Pinus banksiana* that contain a mix of difficult to extract monoterpenes (Hall et al. 2013). It is also in contrast to the blend of monoterpene hydrocarbons obtained upon in vivo expression of the SlPHLS in *Synechocystis* (FIG. 2b). As such, expression of the PbPHLS in cyanobacteria could be used for the generation of a more pure monoterpene hydrocarbon product, when so desired.

Example 3. Heterologous Expression and Activity of *Picea sitchensis* PHLS in *Synechocystis* Transformants The codon optimized sequence encoding the *Picea sitchensis* PHLS (PsPHLS) was expressed as a fusion with CpcB in the cpc locus of the *Synechocystis* genome (FIG. 5a). Genomic DNA PCR analysis was then performed to genetically characterize the transformants. The cpc upstream-to-cpcA region was amplified by PCR and resulted in a 3837 bp product with the transformants. Absence of the 1289 bp product, corresponding to the wt sequence, showed attainment of transgenic DNA copy homoplasmy in the transformants (FIG. 5b). Genome integration of the PsPHLS encoding sequence was specifically verified by PCR amplification of the cpc upstream-to-PsPHLS, yielding a product of 1832 bp in the transformants only (FIG. 5c).

Figures 6A, 6B:
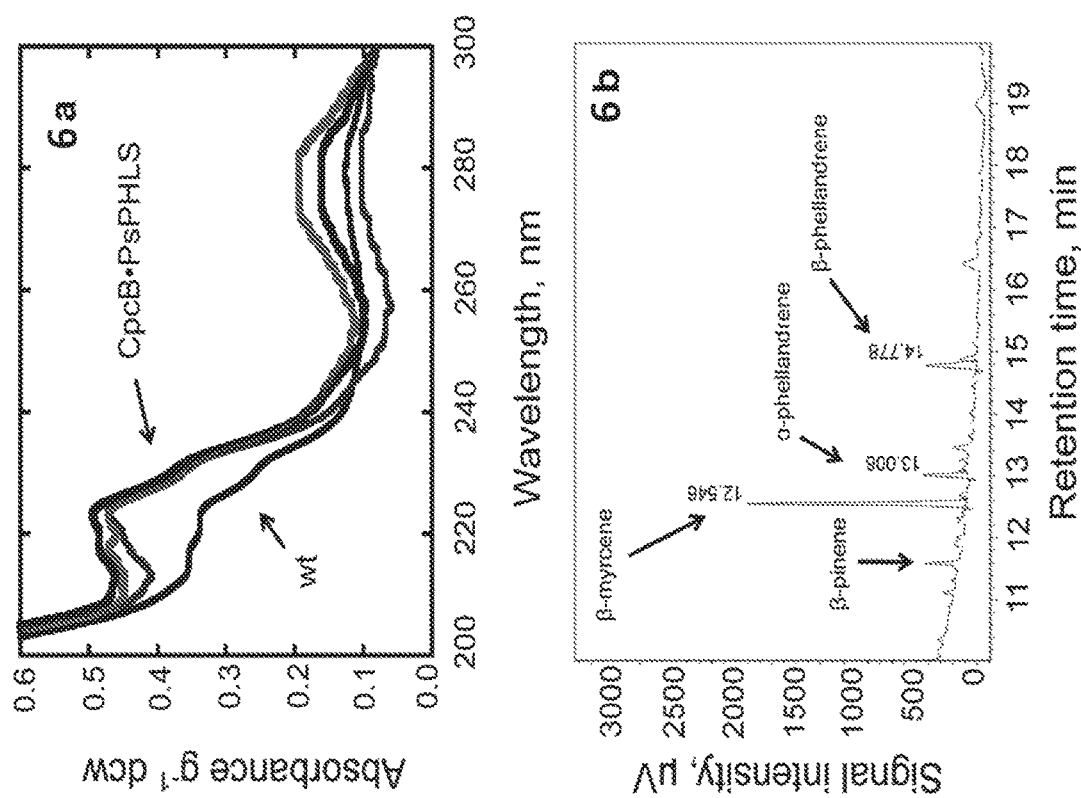
FIG. 6a-6b provides data illustrating monoterpenes production by *Synechocystis* transformants expressing PsPHLS. 6a: UV-absorbance spectra of hexane extracts from *Synechocystis* CpcB·PsPHLS transformnnants, as compared to the wild type. Spectra were normalized on per g of dcw. 6b: GC-FID analysis of the hexane extract from CpcB·PsPHLS transformants. In this case, β-myrcene was the main product with a retention time of 12.546 min, followed by α-phellandrene and β-phellandrene at 13.006 min and 14.778 min of retention time, respectively. Minor amounts of β-pinene (about 11.6-11.8 min) were also detected.

The CpcB·PsPHLS fusion protein, with an expected molecular weight of 84 kD, was detected upon Coomassie staining of electrophoretically resolved total protein extracts (FIG. 5d), indicating successful expression of the recombinant fusion protein. Heterologous expression of the CpcB.PsPHLS fusion resulted in relatively low yields of monoterpene production, as suggested by the low amplitude of UV-absorbance of exudates from the transformants (FIG. 6a), compared with production levels by the CpcB·SlPHLS (FIG. 2a) and CpcB·PsPHLS (FIG. 4a). GC-FID analysis (FIG. 6b) showed β-myrcene as the main monoterpene produced (62%), followed by smaller amounts of β-phellandrene (19%), α-phellandrene (14%), and β-pinene (5%). This profile was consistent with the UV-absorbance spectra of lipophilic extracts from *Synechocystis* transformants. β-Phellandrene has an absorbance peak at 232 nm in hexane (Formighieri and Melis 2014a), while the absorbance max of hexane extracts from the CpcB·PsPHLS transformants was shifted toward 224 nm, where the absorbance maximum of β-myrcene occurs (FIG. 6a). PsPHLS was additionally expressed under the cpc operon promoter in a non-fusion configuration, but this resulted in even lower yields of monoterpene production, likely related to lower protein expression levels (Formighieri and Melis 2014a), while the monoterpenes profile was the same as that shown in FIG. 6b (results not shown). Interestingly, the monoterpene products profile obtained upon heterologous expression of PsPHLS in *Synechocystis* was different than that obtained upon assaying the recombinant enzyme in vitro (Keeling et al. 2011). These results also support the notion that heterologous expression in *Synechocystis* of the PHLS from *Picea sitchensis* (Sitka spruce) results in the generation of substantially different and unique profiles of monoterpenes than those obtained in the same host with the lavender, tomato and pine PHLS enzymes, but also different from the monoterpenes profile of Sitka spruce extracts.

Figures 7A, 7B, 7C, 7D:
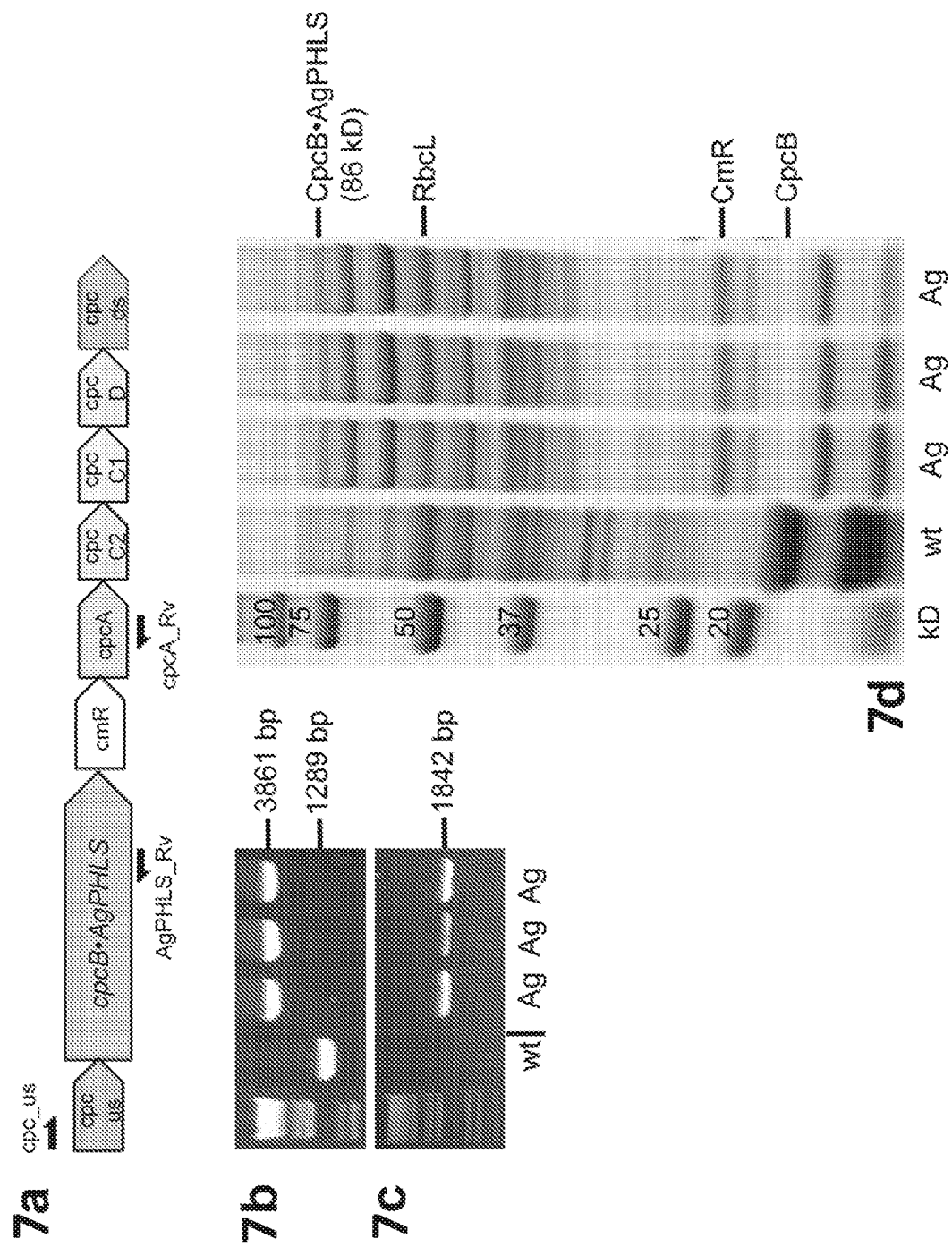
FIG. 7a-7d provides data illustrating expression of *Abies grandis* (grand fir) β-phellandrene synthase (AgPHLS) in *Synechocystis*. 7a: AgPHLS was expressed as a fusion to CpcB in the cpc genomic locus. 7b: Genomic PCR analysis with cpc_us and cpcA_Rv primers. 7c: Genomic PCR analysis with cpc_us and AgPHLS_Rv primers. Location of the primers is shown as arrows in (a). Ag denotes three independent transformants lines. 7d: SDS-PAGE resolution and Coomassie-stain of total cell protein extracts from *Synechocystis* wild type and transformants. The CpcB·AgPHLS fusion protein and the native CpcB are marked at 86 kD and 18 kD, respectively. Molecular weight markers are on the left side and expressed in kD.

Example 4. Heterologous Expression and Activity of *Abies grandis* PHLS in *Synechocystis* Transformants A corresponding DNA recombinant construct, as the ones employed for expression of the PHLS proteins from the afore-mentioned plant species, was also made for expression of the *Synechocystis* codon optimized *Abies grandis* PHLS (FIG. 7a).

Genomic DNA PCR analysis confirmed the genetic identity and homoplasmy of the resulting *Synechocystis* transformants. PCR amplification of the cpc upstream-to-cpcA region resulted in a 3861 bp product with the transformants, and a 1289 bp product when using the wt genome as template (FIG. 7b). Genome integration of the AgPHLS encoding sequence was specifically tested upon amplification of the cpc upstream-to-AgPHLS region, resulting in a 1842 bp product in the transformants only (FIG. 7c). The CpcB·AgPHLS fusion protein was visually detected upon SDS-PAGE and Coomassie staining of total protein extracts, with an expected molecular weight of 86 kD (FIG. 7d).

Figures 8A, 8B:
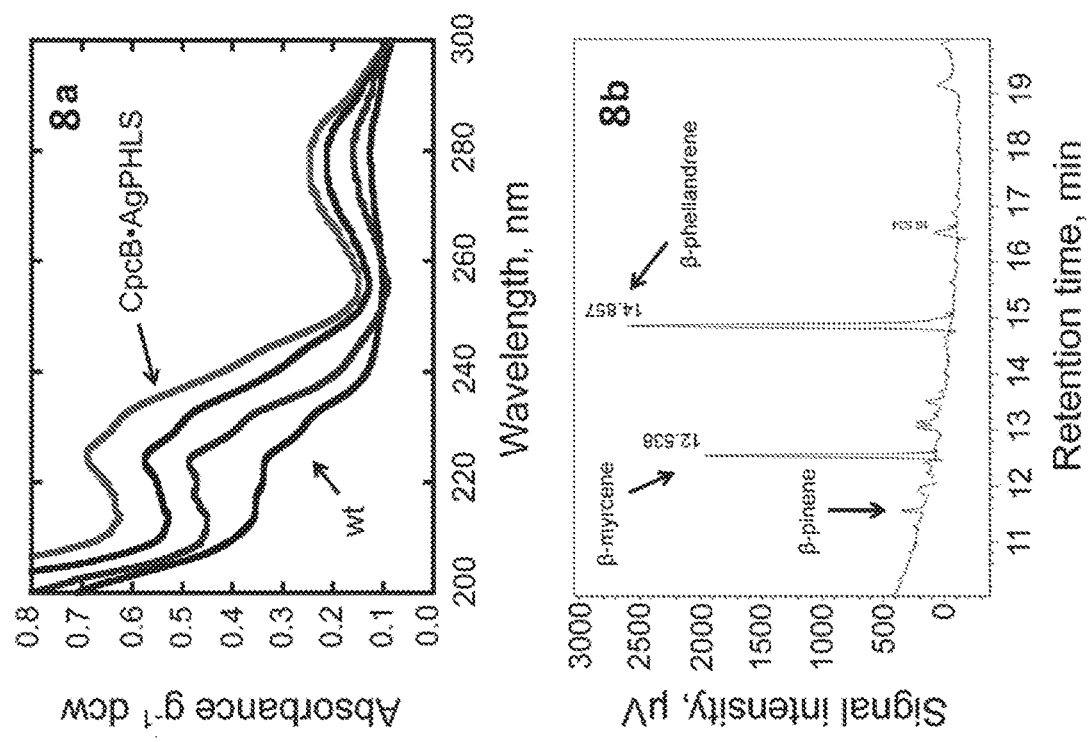
FIG. 8a-8b provides data illustrating monoterpenes production by *Synechocystis* transformants expressing AgPHLS. 8a: UV-absorbance spectra of hexane extracts from *Synechocystis* CpcB·AgPHLS transformants, normalized on per g of dcw and compared to wild type extracts. 8b: GC-FID analysis of the hexane extract from CpcB·AgPHLS transformants that generated β-phellandrene and β-myrcene as the main monoterpenes. Retention times of the two monoterpenes products were 14.857 min 12.538 min, respectively. Smaller amounts of β-pinene (about 11.6-11.8 min) were also detected.

When assayed upon heterologous expression in *Synechocystis*, the CpcB·AgPHLS construct yielded relatively low levels of monoterpenes, as shown by the low level of UV-absorbance (FIG. 8a), compared with production levels by the CpcB·SlPHLS (FIG. 2a) and CpcB·PsPHLS (FIG. 4a) constructs. Even lower yields were obtained upon expression of AgPHLS in a non-fusion configuration, corresponding to lower levels of protein expression (not shown). GC-FID analysis showed that the monoterpene exudates from the CpcB·AgPHLS transformant *Synechocystis* are composed of β-phellandrene (66%), β-myrcene (32%), and β-pinene (2%) (FIG. 8b). This outcome reinforces the above results by showing that heterologous expression of the PHLS from *Abies grandis* (grand fir) in *Synechocystis* results in the generation of unique blends of monoterpenes.

DISCUSSION

The cyanobacterium *Synechocystis* was applied as a microbial factory for heterologous expression of β-phellandrene synthase (PHLS) enzymes from divergent plant species (Schilmiller et al. 2009, Hall et al. 2013, Keeling et al. 2011. Bohlmann et al. 1999). These enzymes, when expressed in the cytosol of the heterologous cyanobacterial host, showed the unexpected ability of producing a variable blend of plant essential oils, whose composition and unique scent differed from what the same enzymes generate in their natural plant hosts, or when assayed in vitro.

β-Phellandrene synthases from divergent plants were reported to primarily produce β-phellandrene (Schilmiller et al. 2009, Hall et al. 2013, Keeling et al. 2011. Bohlmann et al. 1999), although they substantially differed from one-another in their amino acid sequence (FIG. 9a-9d). From the amino acid sequence alignment of different PHLS (FIG. 9a-9d), it is evident that there is a greater divergence in the N-terminal part of the enzymes, as compared to the C-terminal region of the proteins. Overall, the higher degree of identity among the examined sequences is 70% between *Picca sitchensis* and *Abies grandis* PHLS, followed by 63% with the *Pinus banksiana* counterpart. These conifer enzymes are substantially different from the *Lavandula*

*angustifolia* PHLS showing only ~20% of identity with the latter. The *Solanum lycopersicum* PHLS is also substantially different from the other PHLS enzymes examined in the present work, having only ~15% identity with the rest. A rooted phylogenetic tree, based on the ClustalW aminoacid sequence alignment (FIG. 9*a*-9*d*) is reported in FIG. 10. It shows closer proximity, i.e. less nucleotide substitutions per site, among the conifer monoterpene synthases, and a higher degree of sequence divergence between the conifer monoterpene synthases and either the *Lavandula angustifolia* PHLS or the *Solanum lycopersicum* PHLS, consistent with their taxonomic classification (FIG. 10). Although the amino acid sequences are substantially different (FIG. 9*a*-9*d*), important conserved motifs among terpene synthases could be identified as playing a role in the catalysis reported.

In particular, the arginine-rich RR(x8)W signature motif is localized near the N-terminus, but it is part of an N-terminal strand that folds back on the C-terminal domain and supports closure of the active site (Hyatt et al. 2007, Srividya et al. 2015). This motif is uniquely conserved in *Solanum lycopersicum* PHLS as a KR(x9)W sequence (FIG. 9*a*-9*d*).

```
L.angustifoliaADQ73631.1    P-TGRRSGGYPPALWDFDTIQSLN-------------------------    32
(SEQ ID NO: 12)

P.sitchensisADZ45506.1      DGVQRRTGGYHSLNWNDDIIQFLS-------------------------    33
(SEQ ID NO: 13)

A.grandisAAF61453.1         DGLQRRIGDYHSNLWDDDPIQSLS-------------------------    33
(SEQ ID NO: 14)

P.banksianasAFU73854.1      DGVRRRVGDYRYNHWDEDLIDSLA-------------------------    34
(SEQ ID NO: 15)

S.lycopersicumACO56896.1    EQIKRGLGFIETYGWAVDNKDQISPLGFEVIFSSMIKSAEKLDLNLPLNL   150
(SEQ ID NO: 16)
```

The C-terminal α-domain contains the class I (ionization-initiated) active site, characterized by the aspartate-rich DDxxD motif and the partially conserved (N/D)Dxx(S/T)xxxE sequence that coordinate the binding of three divalent metal ($Mg^{2+}$ or $Mn^{2+}$) ions. The latter are required for substrate binding and activation (Demissie et al. 2011, Hyatt et al. 2007, Zhou et al. 2012).

```
L.angustifoliaADQ73631.1    CLDDTYDVYGTIEELQLFTSTIQRWDLKS-MKQLPTYMQVSFLALHNPVT   339
(SEQ ID NO: 17)

P.sitchensisADZ45506.1      ILDDMYDVFGTIDELELFTAQIKRWDPSA-TDCLPKYMKRMYMILYDMVN   373
(SEQ ID NO: 18)

A.grandisAAF61453.1         VLDDIYDTFGTMDEIELFNEAVRRWNPSE-KERLPEYMKEIYMALYEALT   379
(SEQ ID NO: 19)

P.banksianaAFU73854.1       VLDDIYDTYGTMEELELFTAAIKRWDPSV-VDCLPEYMKGVYMAVYDTVN   369
(SEQ ID NO: 20)

S.lycopersicumACO56896.1    IVDDHFESFASKDECFNIIELVERWDDYASVGYKSEKVKVFFSVFYKSIE   542
(SEQ ID NO: 21)

L.angustifoliaADQ73631.1    ERMHKYRDMNRVSSNIVRLADDMGTSLAEVERGDVPKAIQCYMNET-      455
(SEQ ID NO: 22)

P.sitchensisADZ45506.1      KEVDFPSKLNDLASAILRLRGDTRCYKADRARGEEASCISCYMKDNP      497
(SEQ ID NO: 23)

A.grandisAAF61453.1         KGIDFPSRFNDLASSFLRLRGDTRCYKADRDRGEEASSISCYMKDNP      503
(SEQ ID NO: 24)

P.banksianaAFU73854.1       QEIDFPAKFNDLISVILRLKGDTRCYKADRARGEEASSVSCYMKDNA      493
(SEQ ID NO: 25)

S.lycopersicumACO56896.1    ESDEICG-LWNCSGRVMRILNDLQDSK----REQKEVSINLVTLLMK      662
(SEQ ID NO: 26)
```

Modeling of the 3D structures of the PHLS proteins, performed with the RaptorX web server (Källberg et al. 2012), showed interesting differences in the folding of the respective polypeptides. The PHLS from *Lavandula angustifolia* (Bentley et al. 2013. Formighieri and Melis 2014a, Formighieri and Melis 2015) was predicted to have a two-domain ($\alpha\beta$) structure, and is similar to the limonene synthase from *Mentha spicata* that served as the best template (2ongA, p-value 2.43e-14) (FIG. 11a). Terpene synthases are thought to derive from a common ancestor with a three ($\alpha\beta\gamma$) domains structure (Trapp and Croteau 2001). During evolution the $\gamma$-domain was lost from the monofunctional class I terpene synthases, where the active site is embedded in the C-terminal $\alpha$-domain. It was speculated that the extensive contacts that the $\beta$-domain makes with the $\alpha$-domain prevented its deletion (Zhou et al. 2012). The N-terminal strand (FIG. 11a), that precedes the $\beta$-domain, was also retained, and it folds back across the C-terminal $\alpha$-domain to form a 'cap' that shields reactive carbocation intermediates from the solvent (Hyatt et al. 2007, Srividya et al. 2015). Modeling of the CpcB·LaPHLS fusion protein showed the CpcB fusion moiety to be structurally independent from the LaPHLS (FIG. 11b).

As the case was for the LaPHLS, PHLS proteins from conifer trees (*Pinus banksiana, Picea sitchensis* and *Abies grandis*) were also modeled with a two-domain ($\alpha\beta$) structure (FIG. 11a). However, based on their aminoacid sequence, they showed higher similarity with sesquiterpene synthases from conifers, such as the bisabolene synthase from *Abies grandis* (3saeA), rather than other monoterpene synthases from angiosperm species, although they do not have the $\gamma$-domain found in the sesquiterpene synthase (McAndrew et al. 2011).

Interestingly, modeling of the 3D structure of the SIPHLS protein using the RaptorX web server (Källberg et al 2012) showed a three-domain ($\alpha\beta\gamma$) structure (FIG. 11c) with the best template being that of the abietadiene (diterpene) synthase from *Abies grandis* (3s9vA, p-value 9.58e-18). Modeling of the CpcB·SIPHLS fusion protein showed the CpcB domain to be structurally independent from the SIPHLS moiety (FIG. 11d, blue). The common ancestor of terpene synthases is thought to have all three domains active in the catalysis of subsequent steps in product formation (Trapp and Croteau 2001). This is still true for the dual-function abietadiene synthase that has two distinct active sites, one within the $\alpha$-domain and one between the $\beta$ and $\gamma$-domains (Zhou et al. 2012). In the case of the SIPHLS, the C-terminal $\alpha$-domain contains the class I active site where the NPP substrate ionizes to a neryl-cation intermediate before being converted to the monoterpene product(s) (Schilmiller et al. 2009). However, the substantial sequence conservation of the $\beta$ and $\gamma$-domains, as compared to diterpene synthases, suggests that they may have retained a function in SIPHLS and may not be evolutionary relics (Hyatt et al. 2007).

Overall, the differences among PHLS proteins may suggest that the gene function evolved independently more than once (Keeling et al. 2011). Our results further suggest that enzyme function and product specificity also depend on the environment of the cell host or of the cellular compartment, with the biochemical basis of the later causing catalytic deviations from the products naturally observed in the corresponding gene-encoding plants, or upon testing the recombinant proteins in vitro, giving rise to the terpene hydrocarbon blends described in this work.

Upon expression of the aforementioned PHLS proteins in *Synechocystis*, we observed differences in activity and monoterpene products profile. Co-expression of SIPHLS and NPPS led on average to a total monoterpenes yield of 0.6 mg g$^{-1}$ dcw (Table 1), of which $\beta$-phellandrene accounted for 74%, followed by $\alpha$-phellandrene (20%) and $\beta$-myrcene (5%, Table 2). Expression of SIPHLS, as a fusion to CpcB resulted in recombinant protein accumulation clearly visible in SDS-PAGE Coomassie stain; however the NPPS protein was present at low levels in the transformants and could not be discerned in the Coomassie-stain under these conditions (FIG. 1f). Because SIPHLS depends on the heterologous NPP synthase activity to supply the necessary NPP substrate, optimization of NPPS expression could further improve monoterpene yields.

Among the PHLS proteins from conifer trees, the PHLS from *Pinus banksiana* proved to be the most active in *Synechocystis* transformants, yielding an average of 0.33 mg $\beta$-phellandrene g-1 dcw (Table 1). PbPHLS also showed a higher specificity for $\beta$-phellandrene comprising the dominant product (Table 2). Since no heterologous GPPS was co-expressed with PbPHLS, the terpene synthase was able to compete with the endogenous pool of GPP as substrate.

In contrast, heterologous expression of the PHLS from *Picea sitchensis* and *Abies grandis* resulted in lower product yields, although the recombinant proteins were expressed at sufficient levels and clearly visible in SDS-PAGE Coomassie-stain of total cell protein extracts (FIGS. 5, 7). These enzymes also produced a blend of monoterpenes ($\beta$-phellandrene, $\alpha$-phellandrene, and $\beta$-myrcene, and $\beta$-pinene) with the acyclic monoterpene $\beta$-myrcene comprising higher relative amounts than recorded with the other PHLS enzymes (FIGS. 6, 8 and Table 2). $\beta$-Myrcene synthesis by monoterpene synthase enzymes was associated to premature termination of the reaction (Srividya et al. 2015).

Interestingly, monoterpene synthases from angiosperms were reported to require either Mg$^{2+}$ or Mn$^{2+}$ in the ionization steps of the reaction to neutralize the negatively charged diphosphate group of the substrate (Schilmiller et al. 2009, Hyatt et al. 2007). In contrast, monoterpene synthases from conifers specifically require Mn$^{2+}$, while Mg$^{2+}$ was an ineffective cation cofactor, and have the additional requirement for a monovalent cation (K$^+$) (Bohlmann et al. 1997, Green et al. 2009). In this respect, the intracellular environment of *Synechocystis* may be substantially different than the environment where these proteins are naturally active in plants, and also different compared to in vitro assay conditions. Changes in local concentrations of metal ions could affect activity and product specificity of the monoterpene synthases, so that modifications of *Synechocystis* growth media and culture conditions could be a complementary strategy to improve yields and composition toward desired blend of monoterpenes cyanobacteria in vivo.

These examples describe heterologous expression and characterization of plant-based $\beta$-phellandrene synthase enzymes in an illustrative cyanobacteria strain. *Synechocystis*. Expression of these various $\beta$-phellandrene synthase enzymes unexpectedly resulted in monoterpene profiles that included multiple monoterpenes. Further, the monoterpene profiles differed from those in plant extracts. Thus, expression of $\beta$-phellandrene synthase enzymes in cyanobacteria results in the generation of monoterpene hydrocarbon blends with distinctly different chemical properties and scents. These terpene products have commercial value in applications by the cosmetics, pharmaceutical and potentially and other industries.

All publications, accession numbers, and patent applications cited in this specification are herein incorporated by

LISTING OF REFERENCES CITED IN THE APPLICATION BY AUTHOR AND YEAR OF PUBLICATION

Bentley F K, Garcia-Cerdan J G, Chen H C, Melis A (2013) Paradigm of monoterpene (β-phellandrene) hydrocarbons production via photosynthesis in cyanobacteria. BioEnergy Res 6:917-929

Bentley F K, Melis A (2012) Diffusion-based process for carbon dioxide uptake and isoprene emission in gaseous/aqueous two-phase photobioreactors by photosynthetic microorganisms. Biotechnol Bioeng 109:100-109

Bohlmann J. Steele C L, Croteau R (1997) Monoterpene synthases from grand fir (Abies grandis). cDNA isolation, characterization, and functional expression of myrcene synthase, (−) -(4S)-limonene synthase, and (−)-(1S,5S)-pinene synthase. J Biol Chem 272:21784-21792

Bohlmann J, Phillips M, Ramachandiran V, Katoh S, Croteau R (1999) cDNA Cloning, Characterization, and Functional Expression of Four New Monoterpene Synthase Members of the Tpsd Gene Family from Grand Fir (Abies grandis). Archives of Biochemistry and Biophysics 368: 232-243

Demissie Z A, Sarker L S, Mahmoud S S (2011) Cloning and functional characterization of β-phellandrene synthase from Lavandula angustifolia. Planta 233:685-696

Eaton-Rye J J (2011) Construction of gene interruptions and gene deletions in the cyanobacterium Synechocystis sp, strain PCC 6803. Methods Mol Biol 684:295-312

Emanuelsson O, Nielsen H, von Heijne G (1999) ChloroP, a neural network-based method for predicting chloroplast transit peptides and their cleavage sites. Protein Sci. 8:978-984.

Formighieri C, Melis A (2014a) Regulation of β-phellandrene synthase gene expression, recombinant protein accumulation, and monoterpene hydrocarbons production in Synechocystis transformants. Planta 240:309-324

Formighieri C, Melis A (2014b) Carbon partitioning to the terpenoid biosynthetic pathway enables heterologous β-phellandrene production in Escherichia coli cultures. Arch Microbiol 196:853-861

Formighieri C. Melis A (2015) A phycocyanin.phellandrene synthase fusion enhances recombinant protein expression and R-phellandrene (monoterpene) hydrocarbons production in Synechocystis (cyanobacteria). Metab Eng 32:116-124

Formighieri C, Melis A (2016) Sustainable heterologous production of terpene hydrocarbons in cyanobacteria. Photosynth Res DOI: 10.1007/s11120-016-0233-2

Green S, Squire C J, Nieuwenhuizen N J, Baker E N, Laing W (2009) Defining the potassium binding region in an apple terpene synthase. J Biol Chem 284:8661-8669.

Hall D E, Yuen M M S, Jancsik S. Quesada A L, Dullat H K, Li M, Henderson H, Arango-Velez A, Liao N Y, Docking R T, Chan S K, Cooke J E K, Breuil C, Jones S J M, Keeling C I, Bohlmannl J (2013) Transcriptome resources and functional characterization of monoterpene synthases for two host species of the mountain pine beetle, lodgepole pine (Pinus contorta) and jack pine (Pinus banksiana). BMC Plant Biology 13:80-94

Hyatt D C. Youn B, Zhao Y. Santhamma B. Coates R M, Croteau R B, Kang C (2007) Structure of limonene synthase, a simple model for terpenoid cyclase catalysis. Proc Natl Acad Sci USA 104: 5360-5365.

Källberg M. Wang H. Wang S, Peng J, Wang Z, Lu H, Xu J (2012) Template-based protein structure modeling using the RaptorX web server. Nature Protocols 7:1511-1522.

Keeling C I, Weisshaar S, Ralph S G, Jancsik S. Hamberger B, Dullat H K, Bohlmann J (2011) Transcriptome mining, functional characterization, and phylogeny of a large terpene synthase gene family in spruce (Picea spp.). BMC Plant Biol 11:43-57

McAndrew R P, Peralta-Yahya P P, DeGiovanni A, Pereira J H, Hadi M Z, Keasling J D, Adams P D (2011) Structure of a three-domain sesquiterpene synthase: a prospective target for advanced biofuels production. Structure 19:1876-1884.

Schilmiller A L, Schauvinhold I, Larson M, Xu R, Charbonneau A L, Schmidt A, Wilkerson C. Last R L, Pichersky E (2009) Monoterpenes in the glandular trichomes of tomato are synthesized from a neryl diphosphate precursor rather than geranyl diphosphate. PNAS 106: 10865-10870

Srividya N. Davis E M, Croteau R B, Lange B M (2015) Functional analysis of (4S)-limonene synthase mutants reveals determinants of catalytic outcome in a model monoterpene synthase. PNAS 112: 3332-3337

Trapp S C, Croteau R B (2001) Genomic organization of plant terpene synthases and molecular evolutionary implications. Genetics 158:811-832.

Van Wagoner R M, Drummond A K, Wright J L C (2007) Biogenetic diversity of cyanobacterial metabolites. Adv Appi Microbiol 61:89-217

Williams J G K (1988) Construction of specific mutations in photosystem II photosynthetic reaction center by genetic engineering methods in Synechocystis 6803. Methods Enzymol 167:766-778

Zhou K, Gao Y, Hoy J A, Mann F M, Honzatko R B, Peters R J (2012) Insights into diterpene cyclization from structure of bifunctional abietadiene synthase from Abies grandis. J Biol Chem 287:6840-6850.

TABLE 1

Photosynthetic carbon partitioning between monoterpenes and cellular biomass in Synechocystis transformants expressing the PHLS and NPPS from Solanum lycopersicum, or the PHLS from Pinus banksiana. Yields are expressed as mg of total monoterpenes relative to the increment in biomass observed during a 48 h culture incubation period. Three independent transformant lines were assayed for each genotype, with corresponding averages and standard deviations.

| | Total monoterpenes, mg $g^{-1}$ dcw Transformant lines tested | | |
|---|---|---|---|
| | a | b | c |
| SlPHLS + NPPS | 0.760 ± 0.10 | 0.597 ± 0.15 | 0.445 ± 0.06 |
| PbPHLS | 0.348 ± 0.08 | 0.330 ± 0.06 | 0.307 ± 0.02 |

TABLE 2

Monoterpene products profile obtained upon heterologous expression of β-phellandrene synthase in Synechocystis of the following enzymes: *Lavandula angustifolia* (lavender) β-phellandrene synthase (LaPHLS), *Solanum lycopersicum* (tomato) β-phellandrene synthase and neryl diphosphate synthase (SlPHLS + NPPS), *Pinus banksiana* β-phellandrene synthase (PbPHLS), *Picea sitchensis* (Sitka spruce) β-phellandrene synthase (PsPHLS), *Abies grandis* β-phellandrene synthase (AgPHLS). Monoterpenes are expressed as percentage of the total monoterpene blend photosynthetically generated, n.d., not detected.

| | β-Phl | α-Phl | β-Myr | β-Pin | δ-Car |
|---|---|---|---|---|---|
| LaPHLS (Lavender) | 88% | n.d. | 12% | n.d | n.d |
| SlPHLS + NPPS (Tomato) | 74% | 20% | 5% | <1% | <1% |
| PbPHLS (Pine) | >96% | n.d. | <2% | <2% | n.d. |
| PsPHLS (Sitka spruce) | 19% | 14% | 62% | 5% | n.d. |
| AgPHLS (Grand fir) | 66% | n.d. | 32% | 2% | n.d. |

```
Codon-optimized PHLS sequences:
SEQ ID 1. HQ404305| beta-phellandrene synthase [Lavandula angustifolia]
Underlined are the NdeI and BglII restriction sites for cloning at
the 5' and 3'-end, respectively.
```

<u>CATA</u>TGTGTAGTTTGCAAGTTTCTGATCCTATTCCTACCGGACGCCGTTCCGGTGGTTATCCCCCGGCCT

TATGGGATTTCGATACTATTCAATCCCTGAATACCGAATATAAGGGCGAACGTCACATGCGTCGGGAAGA

AGACTTAATTGGTCAAGTTCGGGAAATGTTGGTGCACGAAGTAGAAGATCCCACTCCCCAGTTGGAATTC

ATTGACGATCTGCATAAATTGGGCATTTCCTGCCATTTTGAAAACGAGATTCTGCAAATTCTCAAATCCA

TTTATCTCAACCAAAACTATAAACGGGACCTCTATTCTACCAGTTTAGCCTTCCGTCTCTTGCGTCAATA

CGGGTTTATCTTGCCGCAGGAAGTTTTGACTGCTTTAAAAACGAAGAAGGTACGGATTTTAAACCCAGC

TTCGGCCGGGATATTAAGGGTCTGTTACAGTTGTACGAAGCCTCCTTTTTGTCCCGGAAGGGGGAAGAAA

CTTTACAACTCGCCCGCGAATTTGCTACCAAAATCTTGCAAAAGGAAGTCGATGAACGGGAATTTGCTAC

TAAAATGGAATTTCCCAGTCACTGGACCGTACAAATGCCTAACGCTCGGCCTTTTATCGATGCCTATCGT

CGGCGTCCCGACATGAACCCCGTGGTTCTGGAACTCGCCATTCTCGATACCAATATCGTGCAAGCTCAGT

TTCAAGAAGAATTGAAGGAGACCTCCCGTTGGTGGGAAAGCACGGGGATTGTTCAAGAACTGCCGTTTGT

TCGGGACCGGATTGTGGAAGGTTATTTTTGGACCATTGGTGTTACTCAACGCCGTGAACACGGTTACGAA

CGTATTATGACGGCCAAAGTCATCGCTTTGGTGACCTGTTTGGATGATATTTATGACGTATATGGCACTA

TTGAAGAATTGCAACTCTTCACCTCTACGATTCAGCGTTGGGATTTGGAGTCTATGAAGCAGTTACCGAC

TTATATGCAGGTAAGCTTCCTGGCCTTGCACAATTTTGTAACCGAAGTGGCCTATGATACGCTGAAGAAA

AAGGGCTACAACTCTACCCCCTATTTGCGGAAGACTTGGGTGGATTTGGTCGAAAGTTACATTAAGGAAG

CCACTTGGTACTATAATGGGTACAAACCCTCTATGCAGGAATACCTCAACAACGCCTGGATCTCTGTGGG

CAGCATGGCTATTTTGAATCATTTGTTTTTTCGCTTTACTAATGAACGCATGCATAAGTACCGGGACATG

AATCGTGTATCCTCAATATTGTGCGGTTAGCCGACGATATGGGAACCTCTTTGGCCGAAGTTGAACGCG

GTGACGTGCCCAAAGCTATCCAATGTTACATGAATGAAACGAACGCCTCTGAGGAGGAGGCCCGCGAATA

TGTGCGGCGCGTTATCCAGGAAGAATGGGAAAAACTGAACACTGAACTGATGCGCGACGACGACGATGAC

GATGATTTCACCTTAAGTAAATACTACTGCGAAGTCGTTGCTAACCTGACCCGGATGGCTCAGTTCATTT

ACCAAGATGGTTCCGATGGGTTTGGGATGAAAGATTCCAAAGTAAATCGTTTACTGAAAGAAACGCTGAT

TGAGCGCTATGAGtga<u>AGATCT</u>

SEQ ID 2. ACO56896.1 | beta-phellandrene synthase [*Solanum lycopersicum*]
Underlined are the NdeI and BglII restriction sites for cloning at the
5' and 3'-end, respectively.

<u>CATATG</u>TGCTCCCATTCTACCACCTCGTCCATGAATGGTTTTGAAGATGCCCGGGATCGAATCC

GTGAAAGTTTCGGAAAACTGGAATTGTCTCCCAGTAGCTATGATACCGCGTGGGTAGCCATGGT

TCCAAGCCGTCATTCTCTGAATGAACCCTGCTTCCCACAGTGCCTGGATTGGATTATTGAAAAT

CAGCGGGAAGATGGCTCTTGGGGTCTAAACCCCACCCATCCCCTTCTGCTTAAAGACTCCTTAT

CCTCAACCTTAGCTTGTTTATTGGCACTCACAAAGTGGCGTGTCGGCGACGAACAAATTAAGCG

GGGACTGGGGTTTATTGAAACCTACGGATGGGCCGTGGACAACAAGGATCAAATTTCCCCGCTA

GGCTTTGAAGTCATTTTTAGTAGCATGATTAAGTCCGCAGAAAAGTTGGACTTGAATCTTCCCC

TGAACTTGCACTTAGTCAATCTAGTCAAATGCAAACGGGATAGCACCATTAAACGGAATGTAGA

ATATATGGGAGAAGGCGTAGGTGAATTGTGTGACTGGAAAGAGATGATTAAGCTGCACCAACGT

CAAAATGGGAGTCTGTTTGACAGCCCTGCCACTACTGCCGCCGCCTTGATCTACCACCAGCACG

ATCAAAAGTGTTATCAATACTTGAATAGTATCTTTCAACAACATAAAAACTGGGTGCCCACTAT

GTACCCCACAAAAGTTCATAGTTTATTATGTTTAGTTGATACATTACAAAATCTGGGGGTGCAT

CGTCATTTTAAAAGTGAAATTAAAAAAGCGTTGGACGAAATATACCGTTTATGGCAACAAAAAA

ATGAACAGATTTTTAGCAATGTGACCCATTGCGCCATGGCTTTTCGACTTCTGAGAATGAGTTA

TTACGATGTTAGTTCAGATGAGCTGGCTGAGTTTGTAGATGAAGAACATTTTTTTGCGACTAAC

GGGAAATACAAATCCCACGTTGAAATTTTAGAACTCCATAAAGCGTCTCAATTGGCAATTGACC

ATGAAAAGACGATATTTTGGACAAAATAAACAACTGGACGCGCGCGTTTATGGAACAAAAACT

CCTAAACAACGGCTTTATTGACCGCATGAGTAAAAAGGAAGTTGAATTGGCCTTACGCAAATTT

TACACCACTAGTCACCTCGCAGAAAACCGTCGCTATATCAAAAGTTATGAAGAGAATAACTTCA

AAATTTTAAAAGCGGCCTACCGGAGTCCCAACATTAATAATAAAGACTTACTTGCTTTCTCCAT

CCATGATTTTGAATTATGCCAAGCCCAGCACCGGGAAGAATTACAGCAATTGAAGAGATGGTTT

GAAGATTACCGGTTGGATCAATTAGGCTTAGCCGAACGTTATATTCACGCAAGTTATCTTTTTG

GAGTTACCGTGATCCCGGAGCCCGAGTTATCCGATGCAAGATTGATGTACGCGAAATACGTCAT

GCTTCTAACCATCGTTGATGATCACTTTGAATCCTTTGCGTCGAAAGATGAATGTTTCAACATC

ATTGAATTAGTTGAGCGTTGGGACGATTACGCTTCCGTTGGCTACAAGTCCGAAAAGGTGAAAG

TGTTTTTCAGTGTTTTTTACAAAAGTATTGAAGAACTAGCCACCATTGCTGAAATCAAACAAGG

CCGGAGTGTAAAAAATCACCTGATTAATCTGTGGTTGGAATTGATGAAACTTATGCTTATGAA

CGCGTTGAATGGTGTAGCGGAAAAACGATTCCGAGTATTGAAGAATATCTGTACGTTACCTCTA

TCACTTTTTGTGCTAAGTTGATCCCCCTATCTACCCAATACTTTCTCGGTATTAAAATAAGCAA

AGACCTCTTGGAGAGTGATGAAATTTGTGGTCTCTGGAACTGCTCCGGGCGTGTGATGCGTATT

TTGAACGATTTGCAGGATAGCAAACGTGAGCAAAAAGAAGTTAGTATTAATCTCGTAACTTTAC

TAATGAAATCCATGAGCGAGGAAGAAGCTATCATGAAAATTAAAGAAATTTTGGAAATGAATCG

CCGTGAGCTATTAAAGATGGTTCTTGTCCAGAAGAAAGGTTCCCAACTTCCCCAATTGTGCAAA

GATATTTTTTGGCGCACAAGTAAGTGGGCCCATTTCACCTACTCGCAAACCGATGGGTATCGGA

TAGCCGAAGAAATGAAGAATCACATTGACGAAGTGTTTTATAAACCGTTAAACCACTAG<u>AGATCT</u>

SEQ ID 3. ACO56895.1 | neryl diphosphate synthase 1 [*Solarium lycopersicum*]
Underlined are the BglII and NotI restriction sites for cloning at the
5' and 3'-end, respectively. The ribosome binding site of cpcA for expression
in an operon configuration is shown in grey.

```
AGATCTTCACATTCTAACGGGAGATACCAGAACAATGGCTAGCCTTAATCTACAAACGGAAAAACTGTGTTAC

GAGGACAACGATAACGATCTGGATGAAGAATTGATGCCCAAACACATCGCTTTGATTATGGATGGGAATCGTC

GCTGGGCCAAAGATAAGGGACTAGAAGTCTATGAGGGCCATAAGCATATTATTCCAAAATTAAAAGAAATCTG

TGATATCTCATCTAAGTTAGGCATTCAGATTATTACCGCCTTTGCATTCAGTACTGAGAACTGGAAACGTTCC

AAAGAAGAAGTCGACTTTTTGCTCCAGATGTTTGAAGAAATCTATGATGAGTTCAGCCGCTCTGGTGTTAGAG

TCAGCATTATTGGTTGCAAAAGTGACTTACCCATGACCTTGCAAAAGTGTATTGCTTTAACGGAGGAGACCAC

CAAAGGGAATAAGGGTTTACACCTAGTGATCGCCCTAAACTACGGGGGCTATTACGATATCCTGCAGGCCACC

AAATCCATCGTAAACAAAGCCATGAATGGCCTCTTAGATGTGGAAGACATTAATAAAAACTTGTTTGACCAGG

AATTAGAATCCAAATGTCCGAATCCGGACCTGTTGATTCGCACGGGCGGCGAACAGCGCGTCTCCAATTTTTT

ACTGTGGCAACTAGCGTATACTGAATTTTATTTTACCAATACATTGTTTCCTGACTTCGGGGAAGAAGACTTG

AAAGAAGCGATTATGAACTTCCAGCAGAGGCATCGACGTTTTGGAGGGCATACTTATTAGGCGGCCGC
```

SEQ ID 4. AFU73854.1 | (-)-beta-phellandrene synthase [*Pinus banksiana*]
Underlined are the NdeI and BglII restriction sites for cloning at the
5' and 3'-end, respectively.

```
CATATGGTCAGTAGCACAGCCAGTGTTTCAAATGATGATGGAGTGCGGAGACGCGTGGGCGATTATCGATACA

ATCACTGGGATGAAGACCTGATCGATTCCTTGGCCACCTCATACGAAGCTCCTTCCTATTTGAAACGTGCGGA

TACGCTCGTCGAAGCGATTAAAGATCGGTTTAATAGTATGGGTGTAGATGATGGGGAAAGAATGTCTCCATTA

ACTGATCTCTATCAACGACTGTGGATGGTAGATAGTGTCGAACGTTTGGGTATAGATCGCCATTTCCAAATG

AGATTAAAAGCGCCTTGGACTATGTGTTTTCTTATTGGAAAGAGAAAGGCATCGGTCGTGGCCGCCAAAGCGC

TGTTACCGATCTGAATTCCACCGCCCTGGGCTTACGTACTTTACGACTGCACGGGTACCCCGTGTCATCCGAT

GTGTTGGAAAATTTTAAAGATCATAACGGTCAGTTTACGTGTAGCGGCATTCAAACAGAAGGTGAGATTAGAG

GCGTGTTAAACTTGTTTCGTGCTAGTCTTATCGCCTTCCCCGGCGAAAAAGTCATGGAAGAAGCCGAAATTTT

TTCCACTATGTATCTTAAACATGCCTTGCAAAAAATTGCGGTGTCCAGTCTGTCTCAGGAAATCGAATACTTA

CTGGAGTATGGCTGGCATACCAACCCGCCTCGCCTGGAAGCGCGCATGTATATGGAAGTATTTCCCCAAGACA

CCATCTACGAACAGAAATTAGTGGAACTGGCTAAAGTGGAGTTCAATATCTTTCATTCTCTACAGAAGCGTGA

ACTGCAGTCTTTGACCCGATGGTGGAAACATTATGGGTTCCCCCAATTAAGTTTTACTAGACATATACATGTA

GAGTATTACACATTTGGTAGCTGTATAGCCACTGATCCGAAACAATCGGCATTTCGGCTCTGTTTTGCCAAAA

TGTCATATTTCGTAACCGTGCTAGATGATATCTACGACACGTATGGAACCATGGAGGAACTGGAATTGTTTAC

TGCCGCCATTAAACGCTGGGACCCCTCCGTTGTCGATTGTTTACCGGAGTATATGAAAGGTGTATATATGGCC

GTTTACGATACCGTAAACGAAATGGCGAAGGAGGCGGAAAAAGTACAAGGTCGTGATACGCTAAACTACGTGC

GCCAGGCCTGGGAACTCTATATCGACGCTTATATGCCGGAAGCCAAATGGATTTCAAGTGGCTACCTGCCCAC

TTTTCAAGAATACCTCGATAATTCGAAAATCTCTTTTGGCACTCGGATCACCATTCTTCAACCAATTTTAACG

TTGGGTGAGCCCCTGCCGCACGAAATTCTACAGGAGATTGACTTTCCTGCCAAGTTTAATGATCTAATTTCCG

TGATTCTACGGTTAAAGGGCGACACCAGGTGTTACAAAGCCGATCGAGCGCGAGGCGAGGAGGCATCGTCCGT

CTCCTGCTATATGAAAGATAACGCGGGGATAACCGAAGAAGATGCCATTCACTGCATTAATGATATGGTTAAT

AATCTGCTGAAAGAGTTGAACTGGGAACTGCTGAAACCCGACAGTAACGTGCCCATCAGTTGCCGGAAAGCGG

CCTTCGATATTTGTAGGATTTTTCATCACGGATACAAATATCGGGATGGCTATGGCGACGCAACTATTGAAGT

TAAAAATTTGGTCAAACGCACCGTATTAGAACCCGTTCCCCTGTAGAGATCT
```

SEQ ID 5. ADZ45506.1 | (-)-beta-phellandrene synthase [*Picea sitchensis*]
Underlined are the NdeI and BglII restriction sites for cloning at the
5' and 3'-end, respectively.

CATATGTCCAGCCCTGTGTCTGATGACGGAGTTCAAAGACGGACGGGTGGCTACCATTCCAACT
TATGGAATGATGATATTATTCAATTTTTAAGTACGACTTATGGTGAACCTGCCTATCGAGAACG
AGGCGAACGCTTGATTGATGAAGTTAAAAATATGTTTAATTCGATTTCTATGGAAGATGTTGAG
TTTTCACCACTGAATGACTTGATCCAGCGTCTGTGGATCGTCGATTCCGTCGAACGTTTGGGGA
TCGATCGCCATTTTAAAAACGAAATTAAGTCAACCCTCGACTATGTTTACTCCTACTGGACGCA
GAAGGGCATAGGGTGTGGCATCGAAAGCGTAGTACCAGACTTAAACAGTACGGCACTGGGATTG
CGCACGCTCCGTCTTCATGGATATCCTGTAAGCGCTGAAGTCCTTAAACACTTCCAAAATCAAA
ATGGTCAGTTTGCCTGTAGCCCGTCAGAGACGGAAGGCGAAATGCGGTCCATTGTAAACTTATA
TCGGGCTTCCTTAATTGCATTTCCCGGCGAAAAAGTGATGGAAGAAGCCGAAATTTTTTCCACG
AAATACTTGAAGGAAGCACTGCAGAAAATTCCCGTAAGTAGCCTGAGCCGTGAAATCGGGGATG
TATTGGAACAAGACTGGCATACTAACTTGCCACGATTAGAAGCTCGAAATTACATTGATGTCTT
CGGTCAAGATACTAAAGATACGAAACTGTACATGAAAACCGAGAAACTTCTGGAATTAGCTAAA
CTTGAATTCAACATTTTTCAGTCACTCCAAAAAACGGAACTGGACTCCTTGTTGCGCTGGTGGA
AAGATAGTGGCTTTCATCATATCACCTTTTCCCGACATCTACATGTGGAATATTACACATTGGC
CTCGTGTATCGCCATTGAGCCCCAGCACTCTAGATTTCGCCTTGGCTTTGCCAAAGCGTGTCAT
GTGATAACCATCCTGGATGACATGTACGATGTTTTTGGCACCATCGATGAGTTAGAGCTTTTTA
CCGCACAGATTAAGCGCTGGGACCCGTCAGCTACCGATTGTTTGCCCAAATATATGAAACGCAT
GTATATGATCTTATACGATATGGTGAACGAAATGTCTCGTGAAGCCGAAACCGCCCAGGGAAGG
GATACCCTTAATTACGCCAGACAAGCCTGGGAAGATTTTATCGATTCCTATATGCAGGAAGCAA
AGTGGATCGCTACCGGGTACCTTCCCACGTTCGATGAGTACTTCGAGAACGGTAAGGTTTCCTC
CGGCCATCGTGTTGCCGCGTTGCAGCCCATCCTTACAATGGATATCCCCTTTCCCCATGACATA
TTGAAAGAAGTTGATTTTCCGTCCAAACTCAATGATCTAGCCTCTGCCATCTTGCGTCTACGCG
GCGATACGAGGTGTTATAAAGCCGACCGTGCTCGTGGTGAAGAGGCCTCCTGCATTTCCTGTTA
TATGAAAGACAACCCGGGCGCTACTGAGGAGGACGCTTTGAGCCATATTAACGCGGTGATATCC
GATGTCATTAAAGGATTAAACTGGGAACTACTCAATCCCAATAGTTCCGTGCCGATTTCGTCAA
AAAAGCACGTTTTTGACGTGTCGCGCGCTCTGCACTATGGATATAAGTATCGTGATGGGTATAG
CGTGTCAAATATTGAAACAAAGTCATTGGTCATGAGAACTCTCCTAGAATCAGTACCATTTTAG
AGATCT

SEQ ID 6. AAF61453.1 | beta-phellandrene synthase [*Abies grandis*]
Underlined are the NdeI and BglII restriction sites for cloning
at the 5' and 3'-end, respectively.

CATATGTCCTTGACCACAGCCGTGAGCGATGATGGGCTGCAGAGAAGAATTGGCGACTATCATT
CCAATTTGTGGGATGACGATTTTATACAATCCCTTTCGACACCGTATGGAGAACCTAGTTACCG
TGAACGCGCCGAAAAGCTGATTGGAGAAGTAAAAGAAATGTTTAATTCCATGCCCTCCGAGGAT
GGTGAAAGTATGAGTCCTCTCAACGACTTGATTGAACGTTTGTGGATGGTGGATTCCGTCGAGC
GCTTGGGAATTGACCGTCATTTTAAAAAGAAATTAAGAGCGCTTTGGACTATGTGTACAGCTA
TTGGAATGAGAAAGGCATTGGTTGCGGCCGAGATAGCGTTTTTCCAGATGTGAATAGTACTGCT
AGCGGATTTCGGACTTTGCGGCTACATGGCTATTCCGTATCTAGCGAGGTGTTAAAGGTATTCC
AAGATCAAAATGGTCAGTTCGCATTTTCCCCTAGTACCAAAGAGCGCGACATACGCACTGTCCT
AAACCTCTACCGGGCCTCATTCATCGCCTTTCCAGGTGAGAAAGTAATGGAAGAGGCTGAAATT
TTTAGTAGTCGCTATTTGAAAGAAGCTGTGCAAAAGATCCCCGTTAGTAGCCTCAGTCAAGAAA

```
TTGACTATACTTTGGAATATGGGTGGCATACCAATATGCCTCGGTTGGAAACTCGCAATTACCT

AGACGTGTTTGGCCACCCCACTTCACCGTGGTTAAAAAAGAAACGCACACAATATCTAGACAGT

GAGAAACTCCTGGAATTAGCTAAGCTAGAATTCAATATCTTTCATTCATTACAACAAAAGGAGT

TACAATATCTGTCCCGATGGTGGATTCACTCAGGCCTGCCGGAATTGACGTTTGGTCGACATCG

GCATGTCGAATACTACACCCTCTCTAGCTGTATTGCCACCGAGCCCAAGCATAGTGCTTTTCGC

CTCGGGTTCGCCAAGACTTGTCACCTAATTACCGTTTTGGATGATATCTACGATACGTTTGGAA

CGATGGATGAGATCGAATTGTTTAATGAAGCAGTTCGGCGGTGGAATCCTTCTGAGAAAGAACG

GCTCCCCGAATATATGAAGGAGATATATATGGCACTTTACGAAGCTCTGACCGACATGGCACGT

GAGGCCGAAAAAACTCAGGGCCGTGACACTCTGAACTACGCGCGTAAAGCTTGGGAAGTTTACC

TCGATTCATATACCCAGGAGGCGAAGTGGATCGCTTCCGGGTATTTGCCCACCTTCGAAGAGTA

CCTTGAAAATGCCAAAGTTAGTTCCGGTCACCGGCTGCGGCACTTACCCCGTTATTAACCCTC

GACGTCCCCTTGCCGGATGATGTGCTGAAAGGCATTGACTTTCCCTCCCGTTTTAACGACTTAG

CGTCTAGCTTCTTGCGGCTCCGGGGTGACACCCGCTGTTATAAAGCCGATCGCGATCGAGGAGA

GGAAGCCAGTTCAATCTCTTGTTATATGAAGGATAATCCGGGCCTAACCGAAGAAGATGCGCTC

AATCATATTAATGCGATGATTAACGACATAATTAAGGAATTAAACTGGGAATTGTTGAAACCAG

ATTCCAACATTCCGATGACAGCTCGCAAACACGCGTATGAAATTACGCGCGCTTTTCATCAACT

CTACAAATATCGCGATGGATTCAGCGTTGCCACTCAAGAAACCAAAAGCCTTGTTCGGCGTACC

GTATTAGAACCAGTGCCCTTATAG<u>AGATCT</u>
```

What is claimed is:

1. A method of obtaining a blend of monoterpene hydrocarbons from cyanobacteria in which β-myrcene is the predominant monoterpene, the method comprising:
   culturing a cyanobacteria strain that has been genetically modified to express a heterologous *Picea sitchensis* β-phellandrene synthase as a fusion protein with a cyanobacteria CpcB polypeptide that has at least 95% identity to a wild type cyanobacteria CpcB polypeptide, wherein the heterologous *Picea sitchensis* β-phellandrene synthase has at least 95% identity to SEQ ID NO: 8 and is encoded by a polynucleotide comprising a *Picea sitchensis* β-phellandrene synthase nucleic acid sequence that is codon-optimized for expression in cyanobacteria, and is fused to the 3' end of a leader nucleic acid sequence encoding the cyanobacteria CpcB polypeptide;
   isolating a blend of monoterpene hydrocarbons comprising β-myrcene, β-phellandrene, α-phellandrene, and β-pinene, produced in the cyanobacteria that has spontaneously diffused from the cyanobacteria intracellular space into the culture medium;
   analyzing the levels of monoterpenes present in the monoterpene blend; and
   determining that β-myrcene is the predominant monoterpene present in the blend of monoterpenes.

2. The method of claim 1, wherein the step of analyzing the blend of monoterpene hydrocarbons comprises performing gas chromatography.

3. The method of claim 1, wherein the *Picea sitchensis* β-phellandrene synthase comprises the amino acid sequence of SEQ ID NO: 8.

4. The method of claim 3, wherein the cyanobacteria CpcB polypeptide comprises a wild type *Synechocystis* cyanobacteria CpcB amino acid sequence.

5. The method of claim 1, wherein the *Picea sitchensis* β-phellandrene synthase nucleic acid sequence that is codon-optimized for expression in cyanobacteria has at least 95% identity to the *Picea sitchensis* β-phellandrene synthase coding region of SEQ ID NO: 5.

6. The method of claim 1, wherein the cyanobacteria CpcB polypeptide comprises a wild type *Synechocystis* cyanobacteria CpcB polypeptide amino acid sequence.

7. The method of claim 1, wherein the wild type CpcB polypeptide is *Synechocystis* CpcB.

8. The method of claim 1, wherein the cyanobacteria strain is from a genus selected from the group consisting of *Synechocystis, Synechococcus, Athrospira, Nostoc*, and *Anabaena*.

* * * * *